US012740924B2

(12) United States Patent
Miyata et al.

(10) Patent No.: US 12,740,924 B2
(45) Date of Patent: Sep. 22, 2026

(54) DENTAL PHOTOCURABLE COMPOSITION EXCELLENT IN STORAGE STABILITY

(71) Applicant: SHOFU INC., Kyoto (JP)

(72) Inventors: Shunsuke Miyata, Kyoto (JP); Kenzo Yamamoto, Kyoto (JP); Daisuke Hara, Kyoto (JP)

(73) Assignee: SHOFU INC., Kyoto (JP)

( * ) Notice: Subject to any disclaimer, the term of this patent is extended or adjusted under 35 U.S.C. 154(b) by 1045 days.

(21) Appl. No.: 17/692,598

(22) Filed: Mar. 11, 2022

(65) Prior Publication Data

US 2022/0387264 A1 Dec. 8, 2022

(30) Foreign Application Priority Data

Mar. 12, 2021 (JP) ................................ 2021-040033
Mar. 12, 2021 (JP) ................................ 2021-040037
Mar. 12, 2021 (JP) ................................ 2021-040039
Mar. 12, 2021 (JP) ................................ 2021-040040
Sep. 14, 2021 (JP) ................................ 2021-149804
Sep. 14, 2021 (JP) ................................ 2021-149805

(51) Int. Cl.

| | |
|---|---|
| ***A61K 6/896*** | (2020.01) |
| ***A61C 5/00*** | (2017.01) |
| ***A61K 6/17*** | (2020.01) |
| ***A61K 6/62*** | (2020.01) |
| ***A61K 6/71*** | (2020.01) |
| ***A61K 6/76*** | (2020.01) |
| ***A61K 6/77*** | (2020.01) |

(52) U.S. Cl.

CPC ................ *A61K 6/896* (2020.01); *A61C 5/00* (2013.01); *A61K 6/17* (2020.01); *A61K 6/62* (2020.01); *A61K 6/71* (2020.01); *A61K 6/76* (2020.01); *A61K 6/77* (2020.01)

(58) Field of Classification Search

CPC ........................................................ A61K 6/62
See application file for complete search history.

(56) References Cited

U.S. PATENT DOCUMENTS

| | | | | |
|---|---|---|---|---|
| 5,846,075 | A | 12/1998 | Suh et al. | |
| 6,620,861 | B1 * | 9/2003 | Nakatuka | A61K 6/889 523/201 |
| 7,084,182 | B2 | 8/2006 | Hara et al. | |
| 2005/0123762 | A1 | 6/2005 | Ori et al. | |
| 2007/0100020 | A1 | 5/2007 | Nakatsuka et al. | |
| 2008/0068862 | A1 | 3/2008 | Shimura | |
| 2009/0068123 | A1 | 3/2009 | Takei et al. | |
| 2010/0267856 | A1 | 10/2010 | Shinoda et al. | |
| 2010/0311858 | A1 | 12/2010 | Holmes et al. | |
| 2011/0288195 | A1 * | 11/2011 | Kajikawa | A61K 6/30 522/11 |
| 2015/0342838 | A1 * | 12/2015 | Hara | A61K 6/20 523/120 |
| 2017/0355857 | A1 | 12/2017 | Lee et al. | |
| 2018/0373145 | A1 | 12/2018 | Shiraishi | |
| 2019/0262238 | A1 * | 8/2019 | Hara | A61K 6/77 |
| 2019/0388355 | A1 | 12/2019 | Christensen et al. | |
| 2020/0069534 | A1 | 3/2020 | Furuhashi et al. | |
| 2021/0283022 | A1 | 9/2021 | Miyata et al. | |
| 2022/0002453 | A1 | 1/2022 | Hayakawa et al. | |

FOREIGN PATENT DOCUMENTS

| | | |
|---|---|---|
| EP | 1 101 484 | 5/2001 |
| EP | 2 163 234 | 3/2010 |
| EP | 2 280 032 | 2/2011 |
| EP | 2 394 628 | 12/2011 |
| EP | 3 398 975 | 11/2018 |

(Continued)

OTHER PUBLICATIONS

English machine translation of Fuchigama et al. (JP 2018-172534) (Year: 2018).*

(Continued)

*Primary Examiner* — Michael F Pepitone
(74) *Attorney, Agent, or Firm* — Wenderoth, Lind & Ponack, L.L.P.

(57) ABSTRACT

[Problem]

To provide a dental curable composition having good mechanical property and good storage stability before and after curing.

Solution

The dental curable composition of the present disclosure comprises (A) polymerizable monomer, (BC) polymerization initiator, (D) polymerization accelerator and (E) filler, wherein, the (BC) polymerization initiator comprises (B) photopolymerization initiator and/or (C) chemical polymerization initiator, the (B) photopolymerization initiator comprises (B1) photosensitizer and (B2) photoacid generator, the (C) chemical polymerization initiator comprises (C1) organic peroxide, the (E) filler comprises (E1) surface-treated basic filler, and the (E1) surface-treated basic filler is treated with (F1) surface treatment agent represented by the formula (1) and/or condensate thereof.

[Formula (1)]

[Chemical formula 1]

$$MX_n$$

(In the formula, M is a metal atom selected from Si, Ti, Zr, and Al, X is H, OH or a hydrolyzable group, and may be the same or different from each other. In the case that M is Si, Ti or Zr, n is 4. In the case that M is Al, n is 3.)

27 Claims, No Drawings

(56) References Cited

FOREIGN PATENT DOCUMENTS

| | | | | |
|---|---|---|---|---|
| EP | 3 782 598 | | | 2/2021 |
| JP | 2001-139843 | | | 5/2001 |
| JP | 2005-213231 | | | 8/2005 |
| JP | 2006-76973 | | | 3/2006 |
| JP | 2006-225350 | | | 8/2006 |
| JP | 4093974 | | | 3/2008 |
| JP | 4596786 | | | 10/2010 |
| JP | 4783151 | | | 7/2011 |
| JP | 5114498 | | | 10/2012 |
| JP | 5268478 | | | 5/2013 |
| JP | 5379563 | | | 10/2013 |
| JP | 5461415 | | | 1/2014 |
| JP | 5615720 | | | 9/2014 |
| JP | 2017-119803 | | | 7/2017 |
| JP | 2018172534 | A | * | 11/2018 |
| JP | 2020-500879 | | | 1/2020 |
| WO | 99/62460 | | | 12/1999 |
| WO | 2006/106838 | | | 10/2006 |
| WO | 2008/068862 | | | 6/2008 |
| WO | 2018/164074 | | | 9/2018 |

OTHER PUBLICATIONS

Extended European Search Report issued Jun. 25, 2021 in corresponding European Patent Application No. 21162475.4.

Extended European Search Report issued Sep. 7, 2021 in corresponding European Patent Application No. 21162481.2.

Extended European Search Report issued Sep. 9, 2021 in corresponding European Patent Application No. 21162479.6.

Extended European Search Report issued Sep. 7, 2021 in corresponding European Patent Application No. 21162490.3.

Extended European Search Report issued Sep. 7, 2021 in corresponding European Patent Application No. 21162495.2.

Extended European Search Report issued Aug. 29, 2022 in corresponding European Patent Application No. 22161514.9.

Extended European Search Report issued Aug. 29, 2022 in corresponding European Patent Application No. 22161538.8.

Extended European Search Report issued Aug. 29, 2022 in corresponding European Patent Application No. 22161548.7.

Markus Griesser et al., "Photoinitiators with β-Phenylogous Cleavage: an evaluation of reaction mechanisms and performance", Macromolecules, vol. 45, pp. 1737-1745, 2012.

* cited by examiner

DENTAL PHOTOCURABLE COMPOSITION EXCELLENT IN STORAGE STABILITY

CROSS-REFERENCE TO RELATED APPLICATIONS

This application is based on and claims the benefit of priorities from Japanese Patent Application Serial No. 2021-40033 (filed on Mar. 12, 2021), Japanese Patent Application Serial No. 2021-40037 (filed on Mar. 12, 2021), Japanese Patent Application Serial No. 2021-40039 (filed on Mar. 12, 2021), Japanese Patent Application Serial No. 2021-40040 (filed on Mar. 12, 2021), Application Serial No. 2021-149804 (filed on Sep. 14, 2021) and Application Serial No. 2021-149805 (filed on Sep. 14, 2021), the contents of which are hereby incorporated by reference in their entirety.

BACKGROUND OF THE INVENTION

Field of the Invention

The present disclosure relates to a dental curable composition.

Description of the Related Art

A dental curable composition has been used in the dental field, and applied to a dental adhesive material, a dental composite resin, a dental core build-up material, a dental resin cement, a dental coating material, a dental sealant material, a dental manicure material, a dental splinting material, a dental glass ionomer cement, a dental hard resin, a dental CAD-CAM restoration material, a dental 3D printer material and the like.

A dental composition containing sodium fluoride surface-treated with polysiloxane in order to realize sustained release of fluorine is proposed in International Publication WO2006/106838A, and a dental composition containing inorganic fine particles surface-treated with polysiloxane in order to achieve excellent abrasion resistance and excellent glossiness after polishing is proposed in Japanese Unexamined Patent Application Publication No. 2001-139843 A.

In addition, a dental composition containing a basic core material coated with an inorganic shell containing a metal oxide has been proposed as in Japanese Translation of PCT International Application Publication No. 2020-500879.

SUMMARY OF THE INVENTION

Technical Problem

The dental curable composition is required to have both better storage stability and better physical property than the conventional dental curable composition.

An object of the present disclosure is to provide a dental curable composition having good mechanical property and good storage stability in both before and after curing.

Solution to Problem

A dental curable composition of the present disclosure comprises (A) polymerizable monomer, (BC) polymerization initiator, (D) polymerization accelerator and (E) filler, wherein, the (BC) polymerization initiator comprises (B) photopolymerization initiator and/or (C) chemical polymerization initiator, the (B) photopolymerization initiator comprises (B1) photosensitizer and (B2) photoacid generator, the (C) chemical polymerization initiator comprises (C1) organic peroxide, the (E) filler comprises (E1) surface-treated basic filler, and the (E1) surface-treated basic filler is treated with (F1) surface treatment agent represented by the formula (1) and/or condensate thereof.

[Formula (1)]

[Chemical formula 1]

(In the formula, M is a metal atom selected from Si, Ti, Zr, and Al, X is H, OH or a hydrolyzable group, and may be the same or different from each other. In the case that M is Si, Ti or Zr, n is 4. In the case that M is Al, n is 3.)

Advantageous Effects of Invention

The dental curable composition of the present disclosure has high storage stability and good mechanical property.

DETAILED DESCRIPTION OF THE PREFERRED EMBODIMENTS

In the present disclosure, the (F1) surface treatment agent represented by the formula (1) and/or condensate thereof may be a partial condensate of 2 to 100 molecules of tetraalkoxysilane or a polysiloxane in which all or part of alkoxy groups of a partial condensate of 2 to 100 molecules of tetraalkoxysilane is substituted with OH group.

In the present disclosure, the (E1) surface-treated basic filler may be surface-treated by a wet method and heating under a heat treatment condition at a temperature of 130° C. or higher and 400° C. or lower for an hour or longer and by using the (F1) surface treatment agent represented by the formula (1) and/or condensate thereof.

In the present disclosure, the (E1) surface-treated basic filler may be surface-treated with a silane coupling agent having a polymerizable group and/or an acidic polymer in addition to the surface treatment with the (F1) surface treatment agent represented by the formula (1) and/or condensate thereof.

In the present disclosure, a dispersion of 1.0 g of the (E1) surface-treated basic filler in a mixed solution of 40 g of distilled water and 10 g of ethanol may have pH-value in a range from 7.5 to 10.0 after stirring for 1 hour.

In the present disclosure, the (E1) surface-treated basic filler may be one or more of a fluorosilicate glass, a fluoroaluminosilicate glass and a fluoroaluminoborosilicate glass which contain strontium ion and/or calcium ion.

In the present disclosure, a composition range of the (E1) surface-treated basic filler may satisfy $SiO_2$: 15 to 35% by mass, $Al_2O_3$: 15 to 30% by mass, SrO: 20 to 45% by mass, $P_2O_5$: 0 to 15% by mass, F: 5 to 15% by mass, $Na_2O$: 0 to 10% by mass, $B_2O_3$: 0 to 20% by mass and CaO: 0 to 10 by mass.

In the present disclosure, the dental curable composition may comprise an aryl iodonium salt as the (B2) photoacid generator, and the aryl iodonium salt may be a salt of an anion having an organic group and one or more atoms of P, B, Al, S and Ga, and an aryl iodonium cation.

In the present disclosure, the dental curable composition may comprise an aryl iodonium salt as the (B2) photoacid generator, and the aryl iodonium salt may be a salt of an anion having an organic group in which at least one H is substituted with F and one or more atoms of P, B, Al, S and Ga, and an aryl iodonium cation.

In the present disclosure, the (D) polymerization accelerator may contain aliphatic tertiary amine compound.

In the present disclosure, 1 to 30 parts by mass in 100 parts by mass of the (A) polymerizable monomer contained in the dental curable composition may be (A1) polymerizable monomer having an acidic group.

In the present disclosure, the dental curable composition may be one pack type dental curable composition containing the (B) photopolymerization initiator, and the dental curable composition may comprise, with respect to 100 parts by mass of the (A) polymerizable monomer contained in the dental curable composition, 0.02 to 1.0 parts by mass of the (B1) photosensitizer, 0.1 to 10 parts by mass of the (B2) photoacid generator, 0.2 to 10 parts by mass of the (D) polymerization accelerator, and 10 to 500 parts by mass of the (E1) surface-treated basic filler.

In the present disclosure, the dental curable composition may be two packs type dental curable composition containing the (B) photopolymerization initiator, the dental curable composition may consist of a first paste and a second paste, a mass ratio of the first paste and the second paste may be 1:0.8 to 1.2, and the dental curable composition may comprise, with respect to 200 parts by mass of total of the (A) polymerizable monomer contained in the first paste and the second paste, 0.04 to 2.0 parts by mass of the (B1) photosensitizer, 0.2 to 20 parts by mass of the (B2) photoacid generator, 0.4 to 20 parts by mass of the (D) polymerization accelerator, and 10 to 500 parts by mass of the (E1) surface-treated basic filler.

In the present disclosure, the dental curable composition may be two packs type dental curable composition containing the (C) chemical polymerization initiator, the dental curable composition may consist of a first paste and a second paste, a mass ratio of the first paste and the second paste may be 1:0.8 to 1.2, and the dental curable composition may comprise, with respect to 200 parts by mass of total of the (A) polymerizable monomer contained in the first paste and the second paste, 0.2 to 10 parts by mass of the (C1) organic peroxide, 0.4 to 20 parts by mass of the (D) polymerization accelerator, and 10 to 400 parts by mass of the (E1) surface-treated basic filler.

In the present disclosure, the dental curable composition may be two packs type dental curable composition containing the (C) chemical polymerization initiator, the dental curable composition may consist of a first paste and a second paste, a mass ratio of the first paste and the second paste may be 1:0.8 to 1.2, and the dental curable composition may comprise, with respect to 200 parts by mass of total of the (A) polymerizable monomer contained in the first paste and the second paste, 0.2 to 10 parts by mass of the (C1) organic peroxide, 0.4 to 20 parts by mass of the (D) polymerization accelerator, 10 to 400 parts by mass of the (E1) surface-treated basic filler, and 2 to 60 parts by mass in 200 parts by mass of total of the (A) polymerizable monomer may be (A1) polymerizable monomer having an acidic group.

In the present disclosure, pH-value after immersing a cured body of a dental curable composition having a diameter of 15 mm and a thickness of 1 mm in 5 mL of a lactic acid aqueous solution having pH-value of 4.0 for 24 hours may be 4.5 or more.

In the present disclosure, the dental curable composition may not substantially contain water.

Hereinafter, each component in the dental curable composition of the present disclosure is described in detail.

The dental curable composition of the present disclosure is applied as a dental adhesive material, a dental composite resin, a dental core build-up material, a dental resin cement, a dental coating material, a dental sealant material, a dental manicure material, a dental splinting material, a dental CAD-CAM restoration material, a dental 3D printer material and the like.

In a dental practice, in order to restore aesthetically and functionally a lost portion of a tooth by caries, breakages and the like, a direct method which performs restoration with a dental adhesive material and a composite resin and an indirect method which restores a prosthetic device consisting of ceramics or a dental hard resin with a dental resin cement have been performed as treatment. In addition, a dental adhesive material for adhering a dental composite resin and various dental materials and a natural tooth, a dental splinting material for fixing a mobile tooth, a dental coating material for protecting a vital tooth after forming, against a hyperesthesia, an external stimulation and secondary caries, a dental sealant material for preventing caries by filling deep grooves of a molar tooth, a dental manicure material for temporary recovering aesthetic property by masking discoloration of a tooth, and a dental core build-up material for forming an abutment tooth in the case of collapsing of a dental crown due to caries have been used. In recent years, new composite materials such as a dental CAD-CAM restoration material for preparing a prosthetic device by CAD/CAM processing and a dental 3D printer material for preparing a prosthetic device by 3D printer have been developed, and various dental materials have been used for treatment. The above-described materials are prepared into a uniform paste by mixing a resin matrix consisting of several kinds of polymerizable monomers, a filler such as an inorganic filler and an organic-inorganic composite filler, and a polymerization initiator, according to the application. As one example of some materials, a dental composite resin for filling is used by filling into a tooth in the form of uncured paste, imparting anatomical form of a natural tooth with a dental instrument such as an instrument, and curing by irradiating light with a light irradiator or the like. For the irradiation light from a light irradiator, a light source having an output of about 100 to 2000 $mW/cm^2$ in a wavelength range of about 360 to 500 nm is generally used. On the other hand, a dental resin cement is used for adhering a prosthetic device to a tooth cavity or an abutment tooth, and is cured by light irradiation after attaching the prosthetic device to the tooth cavity or the abutment tooth.

As the photopolymerization initiator used for such dental materials, a photosensitizer and a system in which a photosensitizer is combined with an appropriate photopolymerization accelerator has been widely used. As the photosensitizer, acylphosphine oxide compounds and α-diketone compounds are known, and in particular, α-diketone compounds have an ability to initiate polymerization in the wavelength range of visible light which has little effect on the human body. Furthermore, a tertiary amine compound is well known as a polymerization accelerator to be combined with a photosensitizer, and a combination of an α-diketone compound and a tertiary amine compound has high polymerization activity with respect to irradiation light, and thus has been used in a dental material field. The dental curable composition containing this photopolymerization initiator exhibits excellent mechanical properties such as hardness, flexural strength and compressive strength required for various materials.

However, when the combination of the α-diketone compound and the tertiary amine compound is used as a photopolymerization initiator, a problem that sensitivity to light is poor is caused. Therefore, a photopolymerization initiator containing a photoacid generator which is a specific aryliodonium salt, a sensitizer and an electron donor compound has been proposed. While the dental material containing a photoacid generator has high stability to ambient light, it is highly sensitive to irradiation light, therefore excellent curability is exhibited by irradiating the dental material containing a photoacid generator with light.

On the other hand, there is a case that a chemical polymerization initiator is used for eliminating the operation of light irradiation or for a dental material used for a part where light does not reach sufficiently. As a chemical polymerization initiator, a system in which an organic peroxide typified by benzoyl peroxide and a tertiary aromatic amine compound are combined is known. Usually, the organic peroxide and the tertiary aromatic amine compound react when these are in the same package and therefore are used by being divided into two or more agents. When used, it can be cured without light irradiation by mixing the two agents before applying to the applicable site, therefore it can be preferably used for materials suitable for part where light irradiation cannot be sufficiently performed. Further, the polymerization rate can be further increased by irradiating with light.

There is a case that a dental material contains an ion-releasing basic filler as well as a polymerization initiator and a polymerizable monomer. Examples of the basic filler include fluoroaluminosilicate and calcium silicate. By compounding a basic filler in the dental material, some effects for adjusting an environment in an oral cavity, such as neutralization of acidic component existing around the dental material and release of ions that can be expected to contribute to remineralization such as calcium can be expected. However, there is a tendency in the above described photoacid generator and organic peroxide that storage stability is decreased in the case of coexisting with a basic filler that is not treated or has insufficient surface treatment. Although there is a method of changing the property of the filler by crystallizing a basic filler by heat-treating with a high-temperature heat treatment for a long time, there is a tendency in this method that the acid neutralizing ability and the ion-releasing property are poor.

Further, there is a tendency in the case of containing an acidic compound such as a photoacid generator and an acidic group-containing polymerizable monomer in the composition that the physical property of the cured product deteriorates. Although the detailed principle is unknown, it is considered that the acid in the composition promotes hydrolysis.

In order to solve the above problems, it has found that the above problem can be solved by using a surface-treated basic filler treated with a specific surface treatment agent as the basic filler contained in the dental curable composition of the present disclosure and a photoacid generator and/or an organic peroxide as a polymerization initiator contained in the dental curable composition of the present disclosure to have completed the present disclosure.

(A) Polymerizable Monomer

As the (A) polymerizable monomer contained in the dental curable composition of the present disclosure, any polymerizable monomers can be used without limitation as long as it is known. In the polymerizable monomer or the compound having a polymerizable group described in the present disclosure, the polymerizable group preferably exhibits radical polymerizability, and specifically, from the viewpoint of easy radical polymerization, the polymerizable group is preferably (meth) acrylic group and/or (meth) acrylamide group. In the present specification, "(meth) acrylic" means acrylic and/or methacrylic, "(meth) acryloyl" means acryloyl and/or methacryloyl, "(meth) acrylate" means acrylate and/or methacrylate, and, "(meth) acrylamide" means acrylamide and/or methacrylamide. A polymerizable monomer having a substituent at the α-position of an acrylic group and/or an acrylamide group can also be preferably used. Specific examples include one having one radical polymerizable group, one having two radical polymerizable groups, one having three or more radical polymerizable groups, one having an acidic group, one having an alkoxysilyl group, and one having a sulfur atom.

Specific examples of a polymerizable monomer having one radical polymerizable group and not containing acidic group include 2-hydroxyethyl (meth) acrylate, 3-hydroxypropyl (meth) acrylate, 4-hydroxybutyl (meth) acrylate, 2-hydroxypropyl (meth) acrylate, 2-hydroxybutyl (meth) acrylate, 6-hydroxyhexyl (meth) acrylate, 10-hydroxydecyl (meth) acrylate, propylene glycol mono (meth) acrylate, glycerol mono (meth) acrylate, erythritol mono (meth) acrylate, N-methylol (meth) acrylamide, N-hydroxyethyl (meth) acrylamide, N,N-(dihydroxyethyl) (meth) acrylamide, methyl (meth) acrylate, ethyl (meth) acrylate, propyl (meth) acrylate, isopropyl (meth) acrylate, butyl (meth) acrylate, isobutyl (meth) acrylate, benzyl (meth) acrylate, lauryl (meth) acrylate, 2,3-dibromopropyl (meth) acrylate, 3-(meth) acryloyloxypropyl trimethoxysilane, 11-(meth) acryloyloxyundecyl trimethoxysilane, (meth) acrylamide and the like.

Specific Examples of the polymerizable monomer having two radical polymerizable groups and not containing acidic group include 2,2-bis ((meth) acryloyloxy phenyl) propane, 2,2-bis [4(3-(meth) acryloyloxy)-2-hydroxy propoxyphenyl]propane (generally called "Bis-GMA"), 2,2-bis (4-(meth) acryloyloxy phenyl) propane, 2,2-bis (4-(meth) acryloyloxy polyethoxyphenyl) propane, 2,2-bis (4-(meth) acryloyloxy diethoxyphenyl) propane, 2,2-bis (4-(meth) acryloyloxy tetraethoxyphenyl) propane, 2,2-bis (4-(meth)) acryloyloxy pentaethoxyphenyl) propane, 2,2-bis (4-(meth) acryloyloxy dipropoxyphenyl) propane, 2-(4-(meth) acryloyloxy diethoxyphenyl)-2-(4-(meth) acryloyloxy diethoxyphenyl) propane, 2-(4-(meth) acryloyloxy diethoxyphenyl)-

2-(4-(meth) acryloyloxy ditriethoxyphenyl) propane, 2-(4-(meth) acryloyloxy dipropoxyphenyl)-2-(4-(meth) acryloyloxy triethoxyphenyl) propane, 2,2-bis (4-(meth) acryloyloxy propoxyphenyl) propane, 2,2-bis (4-(meth) acryloyloxy isopropoxyphenyl) propane, 1,4-bis (2-(meth) acryloyloxyethyl) pyromellitate, glycerol di (meth) acrylate, 1-(acryloyloxy)-3-(methacryloyloxy)-2-propanol, ethyleneglycol di (meth) acrylate, diethyleneglycol di (meth) acrylate, triethylene glycol di (meth) acrylate, propylene glycol di (meth) acrylate, butylene glycol di (meth) acrylate, neopentyl glycol di (meth) acrylate, polyethylene glycol di (meth) acrylate, 1,3-butanediol di (meth) acrylate, 1,5-pentanediol di (meth) acrylate, 1,6-hexanediol di (meth) acrylate, 1,10-decanediol di (meth) acrylate, 1,2-bis (3-methacryloyloxy-2-hydroxypropoxy) ethane, 2,2,4-trimethyl hexamethylene bis (2-carbamoyloxy ethyl) dimethacrylate (generally called "UDMA"), 1,2-bis (3-methacryloyloxy-2-hydroxy propoxy) ethane and the like.

Specific Examples of the polymerizable monomer having three or more radical polymerizable groups and not containing acidic group include trimethylolpropane tri (meth) acrylate, trimethylolethane tri (meth) acrylate, trimethylolmethane tri (meth) acrylate, pentaerythritol tri (meth) acrylate, pentaerythritol tetra (meth) acrylate, dipentaerythritol penta (meth) acrylate, N,N-(2,2,4-trimethyl hexamethylene) bis [2-(aminocarboxy) propane-1,3-diol] tetra methacrylate, 1,7-diacryloyloxy-2,2,6,6-tetra acryloyloxymethyl-4-oxyheptane and the like.

(A1) Polymerizable Monomer Having an Acidic Group

The dental curable composition of the present disclosure may contain a (A1) polymerizable monomer having an acidic group. For the (A1) polymerizable monomer having an acidic group, any polymerizable monomer can be used without any limitation as long as it has one or more polymerizable group and at least one acidic group such as a phosphoric acid group, a pyrophosphoric acid group, a thiophosphoric acid group, a phosphonic acid group, a sulfonic acid group and a carboxylic acid group and the like. It is possible to impart adhesive property with respect to a tooth substance and a prosthetic device by containing a (A1) polymerizable monomer having an acidic group. Further, it can be expected to improve the stability of the cured product of the dental curable composition in the case of containing a basic filler in the dental curable composition.

Specific examples of a phosphoric acid group-containing polymerizable monomer include 2-(meth) acryloyloxyethyl dihydrogen phosphate, 3-(meth) acryloyloxypropyl dihydrogen phosphate, 4-(meth) acryloyloxybutyl dihydrogen phosphate, 5-(meth) acryloyloxypentyl dihydrogen phosphate, 6-(meth) acryloyloxyhexyl dihydrogen phosphate, 7-(meth) acryloyloxyheptyl dihydrogen phosphate, 8-(meth) acryloyloxyoctyl dihydrogen phosphate, 9-(meth) acryloyloxynonyl dihydrogen phosphate, 10-(meth) acryloyloxydecyl dihydrogen phosphate, 11-(meth) acryloyloxyundecyl dihydrogen phosphate, 12-(meth) acryloyloxydodecyl dihydrogen phosphate, 16-(meth) acryloyloxyhexadecyl dihydrogen phosphate, 20-(meth) acryloyloxyicosyl dihydrogen phosphate, bis [2-(meth) acryloyl oxyethyl]hydrogensphosphate, bis [4-(meth) acryloyl oxybutyl] hydrogen phosphate, bis [6-(meth) acryloyl oxyhexyl] hydrogen phosphate, bis [8-(meth) acryloyl oxyoctyl] hydrogen phosphate, bis [9-(meth) acryloyl oxynonyl] hydrogen phosphate, bis [10-(meth) acryloyl oxydecyl] hydrogen phosphate, 1,3-di (meth) acryloyl oxypropyl dihydrogenphosphate, 2-(meth) acryloyl oxyethylphenyl hydrogen phosphate, 2-(meth) acryloyloxyethyl-2-bromoethyl hydrogen phosphate and bis [2-(meth) acryloyloxy-(1-hyrdoxymethyl) ethyl] hydrogen phosphate; acyl chloride, alkali metal salt and ammonium salt thereof; and (meth) acrylamide compound in which the ester bond of these compounds is substituted with an amide bond, and the like.

Specific examples of a pyrophosphoric acid group-containing polymerizable monomer include bis [2-(meth) acryloyl oxyethyl] pyrophosphate, bis [4-(meth) acryloyl oxybutyl] pyrophosphate, bis [6-(meth) acryloyl oxyhexyl] pyrophosphate, bis [8-(meth) acryloyl oxyoctyl] pyrophosphate, bis [10-(meth) acryloyl oxydecyl] pyrophosphate; acyl chloride, alkali metal salt and ammonium salt thereof; and (meth) acrylamide compound in which the ester bond of these compounds is substituted with an amide bond, and the like.

Specific examples of a thiophosphate group-containing polymerizable monomer include 2-(meth) acryloyloxyethyl dihydrogen thiophosphate, 3-(meth) acryloyloxypropyl dihydrogen thiophosphate, 4-(meth) acryloyloxybutyl dihydrogen thiophosphate, 5-(meth) acryloyloxypentyl dihydrogen thiophosphate, 6-(meth) acryloyloxyhexyl dihydrogen thiophosphate, 7-(meth) acryloyloxyheptyl dihydrogen thiophosphate, 8-(meth) acryloyloxyoctyl dihydrogen thiophosphate, 9-(meth) acryloyloxynonyl dihydrogen thiophosphate, 10-(meth) acryloyloxydecyl dihydrogen thiophosphate, 11-(meth) acryloyloxyundecyl dihydrogen thiophosphate, 12-(meth) acryloyloxydodecyl dihydrogen thiophosphate, 16-(meth) acryloyloxyhexadecyl dihydrogen thiophosphate, 20-(meth) acryloyloxyicosyl dihydrogen thiophosphate; acyl chloride, alkali metal salt and ammonium salt thereof; and (meth) acrylamide compound in which the ester bond of these compounds is substituted with an amide bond, and the like. The polymerizable monomer having a thiophosphate group is also classified as a polymerizable monomer having a sulfur atom.

Specific examples of a phosphonic acid group-containing polymerizable monomer include 2-(meth) acryloyloxy ethylphenyl phosphonate, 5-(meth) acryloyloxy pentyl-3-phosphonopropionate, 6-(meth) acryloyloxy hexyl-3-phosphonopropionate, 10-(meth) acryloyloxy decyl-3-phosphonopropionate, 6-(meth) acryloyloxy hexyl-3-phosphonoacetate, 10-(meth) acryloyloxy decyl-3-phosphonoacetate; acyl chloride, alkali metal salt and ammonium salt thereof; and (meth)acrylamide compound in which the ester bond of these compounds is substituted with an amide bond, and the like.

Specific examples of a sulfonic acid group-containing polymerizable monomer include 2-(meth) acrylamide-2-methyl propanesulfonic acid and 2-sulfoethyl (meth) acrylate and the like.

The carboxylic acid group-containing polymerizable monomers are classified into a (meth) acrylic-based compound having one carboxyl group in the molecule and a (meth) acrylic-based compound having a plurality of carboxyl groups in the molecule. Examples of the (meth) acrylic-based compound having one carboxyl group in the molecule include (meth) acrylic acid, N-(meth) acryloyl glycine, N-(meth) acryloyl aspartic acid, 0-(meth) acryloyl tyrosine, N-(meth) acryloyl tyrosine, N-(meth) acryloyl phenylalanine, N-(meth) acryloyl-p-aminobenzoic acid, N-(meth) acryloyl-o-aminobenzoic acid, p-vinylbenzoic acid, 2-(meth) acryloyloxybenzoic acid, 3-(meth) acryloyloxybenzoic acid, 4-(meth) acryloyloxybenzoic acid, N-(meth) acryloyl-5-aminosalicylic acid, N-(meth) acryloyl-4-aminosalicylic acid, 2-(meth) acryloyloxyethyl hydrogen succinate, 2-(meth) acryloyloxyethyl hydrogen phthalate, 2-(meth) acryloyloxyethyl hydrogenmalate; acyl chloride thereof; and (meth)acrylamide compound in which the ester bond of these compounds is substituted with an amide bond, and the like. Examples of the (meth) acrylic-based compound having a plurality of carboxyl groups in the molecule include 6-(meth) acryloyl oxyhexane-1,1-dicarboxylic acid, 9-(meth) acryloyl oxynonane-1,1-dicarboxylic acid, 10-(meth) acryloyl oxydecane-1,1-dicarboxylic acid, 11-(meth) acryloyloxy undecane-1,1-dicarboxylic acid, 12-(meth) acryloyl oxydodecane-1,1-dicarboxylic acid, 13-(meth) acryloyloxy tridecane-1,1-dicarboxylic acid, 4-(meth) acryloyloxyethyl trimeritate, 4-(meth) acryloyloxybutyl trimeritate, 4-(meth) acryloyloxyhexyl trimeritate, 4-(meth) acryloyloxydecyl trimeritate, 2-(meth) acryloyl oxyethyl-3'-(meth) acryloyloxy-2'-(3,4-dicarboxy benzoyloxy) propylsuccinate; acid anhydrides and acid halides thereof; and (meth) acrylamide compound in which the ester bond of these compounds is substituted with an amide bond, and the like.

From the view point of imparting adhesive property, the compounding amount of the (A1) polymerizable monomer having an acidic group in the dental curable composition is preferably, with respect to 100 parts by mass of the total amount of the polymerizable monomer contained in the dental curable composition, 1 part by mass or more and 30 parts by mass or less, more preferably 3 parts by mass or more and 20 parts by mass or less. When the compounding amount is less than 1 part by mass, there is a case that sufficient adhesive property to tooth substance, metal or metal oxide is not exhibited. When the compounding amount is more than 30 parts by mass, there is a case that storage stability is lowered.

Specific examples of the polymerizable monomer having an alkoxysilyl group include a (meth) acrylic compound and a (meth) acrylamide compound having one alkoxysilyl group in the molecule and a (meth) acrylic compound and a (meth) acrylamide compound having a plurality of alkoxysilyl groups in the molecule. Specific examples include 2-(meth) acryloxyethyl trimethoxysilane, 3-(meth) acryloxypropyl trimethoxysilane, 3-(meth) acryloxypropyl triethoxysilane, 3-(meth) acryloxypropyl methyldimethoxysilane, 4-(meth) acryloxybutyl trimethoxysilane, 5-(meth) acryloxypentyl trimethoxysilane, 6-(meth) acryloxyhexyl trimethoxysilane, 7-(meth) acryloxyheptyl trimethoxysilane, 8-(meth) acryloxyoctyl trimethoxysilane, 9-(meth) acryloxynonyl trimethoxysilane, 10-(meth) acryloxydecyl trimethoxysilane, 11-(meth) acryloxyundecyl trimethoxysilane. Furthermore, specific examples having a urethane group or an ether group include 3,3-dimethoxy-8,37-dioxo-2,9,36-trioxa-7,38-diaza-3-silatetracontan-40-yl (meth) acrylate, 2-((3,3-dimethoxy-8-oxo-2,9,18-trioxa-7-aza-3-silanonadecane-19-oyl) amino)-2-methylpropane-1,3-diyl di (meth) acrylate, 3,3-dimethoxy-8,19-dioxo-2,9,18-trioxa-7,20-diaza-3-siladocosane-22-yl (meth) acrylate, 3,3-dimethoxy-8,22-dioxo-2,9,12,15,18,21-hexaoxa-7,23-diaza-3-silapentacosane-25-yl (meth) acrylate, 3,3-dimethoxy-8,22-dioxo-2,9,12,15,18,21,26-heptaoxa-7,23-diaza-3-silaoctacosane-28-yl (meth) acrylate, 3,3-dimethoxy-8,19-dioxo-2,9,12,15,18-pentaoxa-7,20-diaza-3-siladocosane-22-yl (meth) acrylate, 3,3-dimethoxy-8,19-dioxo-2,9,12,15,18,23-hexaoxa-7,20-diaza-3-silapentacosane-25-yl (meth) acrylate, 2-((3,3-dimethoxy-8-oxo-2,9,12,15,18-pentaoxa-7-aza-3-silanonadecane-19-oyl) amino)-2-methylpropan-1,3-diyldi (meth) acrylate, 4,4-diethoxy-17-oxo-3,16,21-trioxa-18-aza-4-silatricosane-23-yl (meth) acrylate, 4,4-diethoxy-17-oxo-3,16,21,24-tetraoxa-18-aza-4-silahexacosane-26-yl (meth) acrylate, 4,4-diethoxy-13-oxo-3,12,17-trioxa-14-aza-4-silanonadecane-19-yl (meth) acrylate, 4,4-diethoxy-17-oxo-3,16-dioxa-18-aza-4-silaicosane-20-yl (meth) acrylate and 2-methyl-2-((11-(triethoxysilyl) undecyloxy) carbonylamino) propan-1,3-diyldi (meth) acrylate.

The dental curable composition of the present disclosure may contain a polymerizable monomer having a sulfur atom as the (A) polymerizable monomer in order to impart adhesive property with respect to a noble metal. As the polymerizable monomer having a sulfur atom, any known compound can be used without any limitation as long as it is a polymerizable monomer having one or more sulfur atoms and a polymerizable group. Specifically, it refers to a compound having a partial structure such as —SH, —S—S—, >C═S, >C—S—C<, >P═S, or a compound prepared by tautomerism. Specific examples include 10-methacryloxy decyl-6,8-dithiooctanate, 6-methacryloxy hexyl-6,8-dithiooctanate, 6-methacryloxy hexyl-2-thiouracil-5-carboxylate, 2-(11-methacryloxy undecylthio)-5-mercapto-1,3,4-thiadiazole, 10-(meth) acryloxy decyl dihydrogenthiophosphate.

An oligomer or a prepolymer having at least one polymerizable group in its molecule may be used other than such a polymerizable monomer, without any limitation. There is no problem even if a substituent such as a fluoro group is contained in the same molecule. The polymerizable monomers described above can be used not only singly but also in combinations of a plurality thereof.

The dental curable composition of the present disclosure may contain a silane coupling agent as the (A) polymerizable monomer in order to impart adhesive property with respect to glass ceramics. Any known silane coupling agent can be used without any limitation, but 3-methacryloxypropyl trimethoxysilane, 8-methacryloxyoctyl trimethoxysilane, and 11-methacryloxyundecyl trimethoxysilane are preferable. From the viewpoint of imparting adhesive property, the compounding amount is, with respect to 100 parts by mass of the total amount of the polymerizable monomer contained in the composition, preferably 1 part by mass or more, more preferably 5 parts by mass or more and less than 20 parts by mass. Since the purpose of the silane coupling agent as a polymerizable monomer is to impart adhesive property with respect to glass ceramics or a resin material containing a filler consisting of glass ceramics, the silane coupling agent is compounded separately from the surface treatment agent of the filler.

The dental curable composition of the present disclosure may contain a polymerizable monomer having a sulfur atom as the (A) polymerizable monomer in order to impart adhesive property with respect to a noble metal. From the view point of imparting adhesive property, the compounding amount of the polymerizable monomer having a sulfur atom is, with respect to 100 parts by mass of the total amount of the polymerizable monomer contained in the dental curable composition, 0.01 parts by mass or more, preferably 0.1 parts by mass or more and less than 10 parts by mass.

(BC) Polymerization Initiator

The (BC) polymerization initiator used in the dental curable composition of the present disclosure includes (B) photopolymerization initiator and/or (C) chemical polymerization initiator. The (B) photopolymerization initiator is a polymerization initiator that can initiate polymerization by irradiating with light using a light irradiator or the like. The (C) chemical polymerization initiator is a polymerization initiator that can initiate polymerization by mixing an oxidizing agent and a reducing agent that are divided into two or more agents. The (B) photopolymerization initiator and the (C) chemical polymerization initiator are used in combination with (D) polymerization accelerator to remarkably enhance curability.

(B) Photopolymerization Initiator

The dental curable composition of the present disclosure contains the (B) photopolymerization initiator containing (B1) photosensitizer and (B2) photoacid generator in the case of not containing (C1) organic peroxide. Further, even when the (C1) organic peroxide is contained, it is possible to contain the (B) photopolymerization initiator containing the (B1) photosensitizer and the (B2) photoacid generator. The (B) photopolymerization initiator contained in the dental curable composition of the present disclosure is not particularly limited, and any known photopolymerization initiator commonly used in the dental field may be used without any limitation.

(B1) Photosensitizer

Specific examples of the (B1) photosensitizer which can be used in the present disclosure include α-diketones such as benzil, camphorquinone, camphorquinone carboxylic acid, camphorquinone sulfonic acid, α-naphthyl, acetonaphthene, p,p'-dimethoxybenzyl, p,p'-dichlorobenzylacetyl, pentanedion, 1,2-phenanthrenequinone, 1,4-phenanthrenequinone, 3,4-phenanthrenequinone, 9,10-phenanthrenequinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphine oxides such as bis (2,6-dimethoxy benzoyl) phenylphosphine oxide, bis (2,6-dimethoxy benzoyl) (2,4,4-trimethyl pentyl) phosphine oxide, bis (2,6-dimethoxy benzoyl)-n-butylphosphine oxide, bis (2,6-dimethoxy benzoyl)-(2-methylprop-1-yl) phosphine oxide, bis (2,6-dimethoxy benzoyl)-(1-methylprop-1-yl) phosphine oxide, bis (2,6-dimethoxy benzoyl)-t-butyl phosphine oxide, bis (2,6-dimethoxy benzoyl) cyclohexyl phosphine oxide, bis (2,6-dimethoxy benzoyl) octyl phosphine oxide, bis (2-methoxy benzoyl) (2-methylprop-1-yl) phosphine oxide, bis (2-methoxy benzoyl) (1-methylprop-1-yl) phosphine oxide, bis (2,6-diethoxy benzoyl) (2-methylprop-1-yl) phosphine oxide, bis (2,6-diethoxy benzoyl) (1-methylprop-1-yl) phosphine oxide, bis (2,6-dibutoxy benzoyl) (2-methylprop-1-yl) phosphine oxide, bis (2,4-dimethoxy benzoyl) (2-methylprop-1-yl) phosphine oxide, bis (2,4,6-trimethyl benzoyl) phenyl phosphine oxide, 2,4,6-trimethyl benzoyl diphenyl phosphine oxide, bis (2,4,6-trimethyl benzoyl) (2,4-dipentoxy phenyl) phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, 2,6-dimethoxy benzoyl benzyl butyl phosphine oxide, 2,6-dimethoxy benzoyl benzyl octyl phosphine oxide, bis (2,4,6-trimethyl benzoyl) isobutyl phosphine oxide and 2,6-dimethoxy benzoyl-2,4,6-trimethyl benzoyl-n-butyl phosphine oxide; acylgermanium compounds such as bisbenzoyl diethylgermanium, bisbenzoyl dimethylgermanium, bisbenzoyl dibutylgermanium, bis (4-methoxybenzoyl) dimethylgermanium and bis (4-methoxybenzoyl) diethylgermanium; α-aminoacetophenones such as 2-benzyl-dimethylamino-1-(4-morpholinophenyl)-butanone-1, and 2-benzyl-diethylamino-1-(4-morpholinophenyl)-propanone-1; ketals such as benzyl dimethyl ketal, benzyl diethyl ketal and benzyl (2-methoxyethyl ketal); and titanocenes such as bis (cyclopentadienyl)-bis [2,6-difluoro-3-(1-pyrrolyl) phenyl]-titanium, bis (cyclopentadienyl)-bis (pentanefluorophenyl)-titanium and bis (cyclopentadienyl)-bis (2,3,5,6-tetrafluoro-4-disiloxyphenyl)-titanium.

The photosensitizer (131) may be appropriately selected according to the wavelength, the intensity and the irradiation time of light used for polymerization, and the type and the compounding amount of other components to be combined. In addition, the photosensitizer may be used not only singly but also in combinations of two or more. Among them, α-diketone compounds having a maximum absorption wavelength in the visible light region are preferably used, and camphorquinone compounds such as camphorquinone, camphorquinone carboxylic acid and camphorquinone sulfonic acid are more preferable. Camphorquinone is particularly preferred because it is easily available.

Usually, the compounding amount of the (131) photosensitizer with respect to 100 parts by mass of the total amount of the (A) polymerizable monomer contained in the dental curable composition is preferably 0.02 to 1.0 parts by mass, more preferably 0.05 to 0.5 parts by mass. When the compounding amount of the photosensitizer is less than 0.02 parts by mass, there is a case that the polymerization activity with respect to the irradiation light is poor and the curing becomes insufficient. When the compounding amount is more than 1.0 parts by mass, there is a case that although sufficient curability is exhibited, the sensitivity to light is shortened, and yellowness is increased. The dental curable composition of the present disclosure may contain only the α-diketone compound as the (B1) photosensitizer.

(B2) Photoacid Generator

As the (B2) photoacid generator used in the dental curable composition of the present disclosure, known compounds can be used without limitation. Specific examples include triazine compounds, iodonium salt compounds, sulfonium salt compounds, and sulfonic acid ester compounds. Among these, triazine compounds and iodonium salt-based compounds are preferable because of having high polymerizability in the case of using in combination with a sensitizer. Iodonium salt-based compounds are more preferable. Iodonium-based salt compounds are susceptible to sensitization by photosensitizers that have absorption in the visible light region.

Specific examples of the triazine compound include 2,4,6-tris (trichloro methyl)-s-triazine, 2,4,6-tris (tribromo methyl)-s-triazine, 2-methyl-4,6-bis (trichloro methyl)-s-triazine, 2-methyl-4,6-bis (tribromo methyl)-s-triazine, 2-phenyl-4,6-bis (trichloro methyl)-s-triazine, 2-(p-methoxy phenyl)-4,6-bis (trichloro methyl)-s-triazine, 2-(p-methyl thiophenyl)-4,6-bis (trichloro methyl)-s-triazine, 2-(p-chloro phenyl)-4,6-bis (trichloro methyl)-s-triazine, 2-(2,4-dichloro phenyl)-4,6-bis (trichloro methyl)-s-triazine, 2-(p-bromo phenyl)-4,6-bis (trichloro methyl)-s-triazine, 2-(p-tolyl)-4,6-bis (trichloro methyl)-s-triazine, 2-n-propyl-4,6-bis (trichloro methyl)-s-triazine, 2-(α,α,β-trichloro ethyl)-4,6-bis (trichloro methyl)-s-triazine, 2-styryl-4,6-bis (trichloro methyl)-s-triazine, 2-[2-(p-methoxy phenyl) ethenyl]-4,6-bis (trichloro methyl)-s-triazine, 2-[2-(o-methoxy phenyl) ethenyl]-4,6-bis (trichloro methyl)-s-triazine, 2-[2-(p-butoxy phenyl) ethenyl]-4,6-bis (trichloro methyl)-s-triazine, 2-[2-(3,4-dimethoxy phenyl) ethenyl]-4,6-bis (trichloro methyl)-s-triazine, 2-[2-(3,4,5-trimethoxy phenyl) ethenyl]-4,6-bis (trichloro methyl)-s-triazine, 2-(1-naphthyl)-4,6-bis (trichloro methyl)-s-triazine, 2-(4-biphenylyl)-4,6-bis (trichloro methyl)-s-triazine, 2-[2-{N,N-bis(2-hydroxy ethyl) amino} ethoxy]-4,6-bis (trichloro methyl)-s-triazine, 2-[2-{N-hydroxy ethyl-N-ethylamino} ethoxy]-4,6-bis (trichloro methyl)-s-triazine, 2-[2-{N-hydroxy ethyl-N-methylamino} ethoxy]-4,6-bis (trichloro methyl)-s-triazine, 2-[2-{N,N-diallyl amino} ethoxy]-4,6-bis (trichloro methyl)-s-triazine and the like. Among them, 2,4,6-tris (trichloro methyl)-s-triazine is preferable.

Any iodonium salt-based compound can be used as long as it is known. For the specific examples, the structural formula of the iodonium salt-based compound can be represented by the following formula (2).

[Formula (2)]

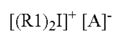

(In the formula, $[(R1)_2I]^+$ is a cation part, $[A]^-$ is an anion part, R1 shown in the formula (2) represents an organic group bonded to I, and R1s may be the same or different. R1 represents, for example, an aryl group having 6 to 30 carbon atoms, a heterocyclic group having 4 to 30 carbon atoms, an alkyl group having 1 to 30 carbon atoms, an alkenyl group having 2 to 30 carbon atoms, or an alkynyl group having 2 to 30 carbon atoms, which may have at least one substituted group selected from the group consisting of groups such as alkyl, hydroxy, alkoxy, alkylcarbonyl, arylcarbonyl, alkoxycarbonyl, aryloxycarbonyl, arylthiocarbonyl, acyloxy, arylthio, alkylthio, aryl, heterocycle, aryloxy, alkylsulfinyl, arylsulfinyl, alkylsulfonyl, arylsulfonyl, alkyleneoxy, amino, cyano, nitro groups and halogens.)

In the above, examples of the aryl group having 6 to 30 carbon atoms include a monocyclic aryl group such as a phenyl group and a condensed polycyclic aryl group such as a naphthyl, anthrasenyl, phenanthrenyl, pyrenyl, chrysenyl, naphthacenyl, benzanthrasenyl, anthraquinolyl, fluorenyl, naphthoquinone and anthraquinone.

Examples of the heterocyclic group having 4 to 30 carbon atoms include cyclic groups containing 1 to 3 heteroatoms such as oxygen, nitrogen, and sulfur, which may be the same or different. Specific examples include a monocyclic heterocyclic group such as thienyl, furanyl, pyranyl, pyrrolyl, oxazolyl, thiazolyl, pyridyl, pyrimidyl and pyrazinyl, and a condensed polycyclic heterocyclic group such as indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl and dibenzofuran.

Specific examples of alkyl groups having 1 to 30 carbon atoms include a linear alkyl group such as methyl, ethyl, propyl, butyl, hexadecyl and octadecyl, a branched alkyl group such as isopropyl, isobutyl, sec-butyl, tert-butyl, isopentyl, neopentyl, tert-pentyl, isohexyl and a cycloalkyl groups such as cyclopropyl, cyclobutyl, cyclopentyl and cyclohexyl.

In addition, specific examples of the alkenyl group having 2 to 30 carbon atoms include a linear chain or branched group such as vinyl, allyl, 1-propenyl, isopropenyl, 1-butenyl, 2-butenyl, 3-butenyl and 1-methyl-1-propenyl.

Further, specific examples of the alkynyl group having 2 to 30 carbon atoms include a linear chain or branched group such as ethynyl, 1-propynyl, 2-propynyl, 1-butynyl, 2-butynyl, 3-butynyl, 1-methyl-1-propynyl and 1-methyl-2-propynyl.

The above-described aryl group having 6 to 30 carbon atoms, heterocyclic group having 4 to 30 carbon atoms, alkyl group having 1 to 30 carbon atoms, alkenyl group having 2 to 30 carbon atoms and alkynyl group having 2 to 30 carbon atoms may have at least one substituted group. Specific examples of the substituted group include a linear alkyl group having 1 to 18 carbon atoms such as methyl, ethyl, propyl, butyl and octadecyl; a branched alkyl group having 1 to 18 carbon atoms such as isopropyl, isobutyl, sec-butyl and tert-butyl; a cycloalkyl group having 3 to 18 carbon atoms such as cyclopropyl, cyclobutyl, cyclopentyl and cyclohexyl; a hydroxy group; a linear chain or branched alkoxy group having 1 to 18 carbon atoms such as methoxy, ethoxy, propoxy, isopropoxy, butoxy, isobutoxy, sec-butoxy, tert-butoxy and dodecyloxy; a linear chain or branched alkylcarbonyl group having 2 to 18 carbon atoms such as acetyl, propionyl, butanoyl, 2-methylpropionyl, heptanoyl, 2-methylbutanoyl, 3-methylbutanoyl and octanoyl; an arylcarbonyl group having 7 to 11 carbon atoms such as benzoyl and naphthoyl; a linear chain or branched alkoxycarbonyl group having 2 to 19 carbon atoms such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl; an aryloxycarbonyl group having 7 to 11 carbon atoms such as phenoxycarbonyl and naphthoxycarbonyl; an arylthiocarbonyl group having 7 to 11 carbon atoms such as phenylthiocarbonyl and naphthoxythiocarbonyl; a linear chain or branched acyloxy group having 2 to 19 carbon atoms such as acetoxy, ethylcarbonyloxy, propylcarbonyloxy, isobutylcarbonyloxy, sec-butylcarbonyloxy, tert-butylcarbonyloxy and octadecylcarbonyloxy; an arylthio group having 6 to 20 carbon atoms such as phenylthio, biphenylthio, methylphenylthio, chlorophenylthio, bromophenylthio, fluorophenylthio, hydroxyphenylthio, methoxyphenylthio, naphthylthio, 4-[4-(phenylthio) benzoyl]phenylthio, 4-[4-(phenylthio) phenoxy] phenylthio, 4-[4-(phenylthio) phenyl] phenylthio, 4-(phenylthio) phenylthio, 4-benzoyl phenylthio, 4-benzoyl-chlorophenylthio, 4-benzoyl-methylthio phenylthio, 4-(methylthiobenzoyl) phenylthio and 4-(p-tert-butylbenzoyl) phenylthio; a linear chain or branched alkylthio group having 1 to 18 carbon atoms such as methylthio, ethylthio, propylthio, tert-butylthio, neopentylthio and dodecylthio; an aryl group having 6 to 10 carbon atoms such as phenyl, tolyl, dimethylphenyl and naphthyl; a heterocycle group having 4 to 20 carbon atoms such as thienyl, furanyl, pyranyl, xanthenyl, chromanyl, isochromanyl, xanthonyl, thioxanthonyl and dibenzofuranyl; an aryloxy group having 6 to 10 carbon atoms such as phenoxy and naphthyloxy; a linear chain or branched alkylsulfinyl group having 1 to 18 carbon atoms such as methylsulfinyl, ethylsulfinyl, propylsulfinyl, tert-pentylsulfinyl and octylsulfinyl; an arylsulfinyl group having 6 to 10 carbon atoms such as phenylsulfinyl, tolylsulfinyl and naphthylsulfinyl; a linear chain or branched alkylsulfonyl group having 1 to 18 carbon atoms such as methylsulfonyl, ethylsulfonyl, propylsulfonyl, isopropylsulfonyl, butylsulfonyl and octylsulfonyl; an arylsulfonyl group having 6 to 10 carbon atoms such as phenylsulfonyl, tolylsulfonyl (tosyl), naphthylsulfonyl; an alkyleneoxy groups; a cyano groups; a nitro groups; and halogens such as fluorine, chlorine, bromine and iodine.

Among the iodonium salt-based compounds, the aryl iodonium salt is preferable because of having high stability. Further, it is preferable that the aryl group has a substituent in order to improve the solubility to the photopolymerization composition. Specifically, a linear alkyl group such as methyl, propyl, octyl, decyl, undecyl, dodecyl and tridecyl, a branched alkyl group such as isopropyl, isobutyl, sec-butyl, tert-butyl, isopentyl, neopentyl, tert-pentyl and isohexyl, a functional group in which one or more of H of these is substituted with F, a perfluoroalkyl group and halogen is suitable as the substituent.

The structure of an anion portion of the iodonium salt-based compound is not particularly limited, and examples include those having atoms such as halogen, P, S, B, Al and Ga. From the viewpoint of safety, anions having As or Sb can be used, but they are not preferable in dental applications. Further, the anion preferably has an organic group such as an alkyl group and/or an alkoxy group and/or an aryl group, and further, most preferably has an organic group such as an alkyl group and/or an alkoxy group and/or an aryl group, in which at least one H is substituted with F. Since the iodonium salt-based compound having such an anion has high solubility in the dental curable composition, it is expected to preventing precipitation during low-temperature storage or long-term storage and to shorten the time for preparing due to dissolving in the composition in a short time. Further, an iodonium salt-based compound of an anion having an organic group such as an alkyl group and/or an alkoxy group and/or an aryl group, in which at least one H is substituted with F can be expected to have higher solubility. When the photoacid generator is precipitated, there is a case that it may cause a decrease in color stability after irradiation and a decrease in flexural strength, and therefore it is not preferable. As the anion having an organic group such as an alkyl group and/or an alkoxy group and/or an aryl group, in which at least one H is substituted with F, an anion having any atom can be used. However, from the viewpoint of versatility and safety, those having one or more of P, S, B, Al and Ga are preferable.

Examples of the anion having no alkyl group and/or alkoxy group and/or aryl group include halogens such as chloride and bromide, perhalonic acids such as perchloric acid, aromatic sulfonic acids such as p-toluenesulfonate, camphorsulfonnic acids, nitrates, acetates, chloroacetates, carboxylates, phenolates, tetrafluoroborates, hexafluorophosphates, hexafluoroantimonates, hexafluoroarsenates and the like. Among these, p-toluenesulfonate, camphorsulfonic acid and carboxylate are preferably used.

Since the anionic part of $[A]^-$ of the iodonium salt-based compound of the formula (2) improves the solubility to the dental curable composition, it is preferable that the anion has an organic group such as alkyl group and/or alkoxy group and/or aryl group, in which at least one H is substituted with F. Specifically, the number of carbon atoms of the alkyl group in the anion part of $[A]^-$ of the iodonium salt-based compound of the formula (2) is 1 to 8, and preferably 1 to 4. Specific examples include a linear alkyl group such as methyl, ethyl, propyl, butyl, pentyl and octyl, a branched alkyl group such as isopropyl, isobutyl, sec-butyl and tert-butyl, and a cycloalkyl group such as cyclopropyl, cyclobutyl, cyclopentyl and cyclohexyl. The ratio (F/H) of the number of hydrogen atoms to fluorine atoms in the alkyl group is 4 or more, and the ratio (F/H) of the number of hydrogen atoms to fluorine atoms in the alkyl group is preferably 9 or more. More preferably, all hydrogen atoms of the hydrocarbon are substituted with fluorine. An iodonium salt consisting of an anion having an alkyl group having a different ratio of a hydrogen atom and a fluorine atom may be compounded in the dental curable composition.

Further, specific examples of the alkyl group include a linear chain or branched perfluoroalkyl group such as $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$ and $(CF_3)_3C$.

The number of carbon atoms of the alkyl group in the anion part of $[A]^-$ of the iodonium salt-based compound of the formula (2) is 1 to 8, and preferably 1 to 4. Specific examples include a linear alkoxy group such as methoxy, ethoxy, propoxy, butoxy, pentoxy and octoxy, and a branched alkoxy group such as isopropoxy, isobutoxy, sec-butoxy and tert-butoxy. The ratio (F/H) of the number of hydrogen atoms to fluorine atoms in the alkyl group is 4 or more, and the ratio (F/H) of the number of hydrogen atoms to fluorine atoms in the alkyl group is preferably 9 or more. More preferably, all hydrogen atoms of the hydrocarbon are substituted with fluorine. An iodonium salt consisting of an anion having an alkoxy group having a different ratio of a hydrogen atom and a fluorine atom may be compounded in the dental curable composition.

Further, specific examples of the alkoxy group include a linear or branched perfluoroalkoxy group such as $CF_3O$, $CF_3CF_2O$, $CF_3CF_2CF_2O$, $(CF_3)_2CFO$, $CF_3CF_2CF_2CF_2O$, $(CF_3)_2CFCF_2O$, $CF_3CF_2(CF_3)CFO$, $CF_3CF_2CF_2CF_2CF_{20}$ and $CF_3CF_2CF_2CF_2CF_2CF_2CF_2CF_2O$.

The phenyl group in the anion part of $[A]^-$ of the iodonium salt compound of the formula (2) may be a phenyl group, in which at least one H is substituted with fluorine atom, an alkyl group and/or an alkoxy group substituted with fluorine atom. The alkyl group and/or alkoxy group substituted with fluorine atom are preferably those described above. Specific examples of particularly preferable phenyl group include perfluorophenyl group such as pentafluorophenyl group ($C_6F_5$), trifluorophenyl group ($C_6H_2F_3$), tetrafluorophenyl group ($C_6HF_4$), trifluoromethylphenyl group ($CF_3C_6H_4$), bis (trifluoromethyl) phenyl group ($(CF_3)_2C_6H_3$), pentafluoroethyl phenyl group ($CF_3CF_2C_6H_4$), bis (pentafluoroethyl) phenyl group ($(CF_3)_2C_6H_3$), trifluoromethyl fluorophenyl group ($CF_3C_6H_3F$), bistrifluoromethyl fluorophenyl group ($(CF_3)_2C_6H_2F$), pentafluoroethyl fluorophenyl group ($CF_3CF_2C_6H_3F$), bispentafluoroethyl fluorophenyl group $(CF_3CF_2)_2C_6H_2F$ and the like. An iodonium salt consisting of an anion having a phenyl group having a different ratio of a hydrogen atom and a fluorine atom may be compounded in the dental curable composition.

As specific examples of the anion portion of $[A]^-$ of the iodonium salt compound of the formula (2), examples of the anion having P include $[(CF_3CF_2)_3PF_3]^-$, $[(CF_3CF_2CF_2)_3PF_3]^-$, $[((CF_3)_2CF)_2PF_4]^-$, $[((CF_3)_2CF)_3PF_3]^-$, $[((CF_3)_2CF)_4PF_2]^-$, $[((CF_3)_2CFCF_2)_2PF_4]^-$, $[((CF_3)_2CFCF_2)_3PF_3]^-$ and the like. Examples of the anion having S include $[(CF_3SO_2)_3C]^-$, $[(CF_3CF_2SO_2)_3C]^-$, $[(CF_3CF_2CF_2SO_2)_3C]^-$, $[(CF_3CF_2CF_2CF_2SO_2)_3C]^-$, $[CF_3CF_2CF_2CF_2SO_3]^-$, $[CF_3CF_2CF_2SO_3]^-$, $[(CF_3CF_2SO_2)_3C]^-$, $[(SO_2CF_3)_3N]^-$, $[(SO_2CF_2CF_3)_2N]^-$, $[((CF_3)C_6H_4)SO_3]^-$, $[SO_3(CF_2CF_2CF_2CF_2)SO_3]^{2-}$ and the like. Examples of the anion having B include $[B(C_6F_5)_4]^-$, $[(C_6H_5)B((CF_3)_2C_6H_3)_3]^-$, $[(C_6H_5)B(C_6F_5)_3]^-$ and the like. Examples of an anion having Ga include $[((CF_3)_4Ga)]^-$, $[Ga(C_6F_5)_4]^-$ and the like. Examples of anions having Al include $[((CF_3)_3CO)_4Al]^-$, $[((CF_3CF_2)_3CO)_4Al]^-$.

The compounding amount of the (B2) photoacid generator in the dental curable composition of the present disclosure is preferably 0.1 to 10 parts by mass or more, more preferably 0.2 to 5 parts by mass or more, with respect to 100 parts by mass of the total amount of the (A) polymerizable monomer. When the compounding amount of the photoacid generator is less than 0.1 parts by mass, there is a case that expected polymerization promoting ability is not exhibited and the curing becomes insufficient. When the compounding amount is more than 10 parts by mass, although sufficient curability is exhibited, there is a case that the sensitivity to light is lowered to shorten working time, and discoloration such as browning of the cured body increases.

The photoacid generator that can be used in the dental curable composition of the present disclosure is not limited to the photoacid generator described in the specific example, and two or more types can be used in combination.

The dental curable composition of the present disclosure may comprise only an aryl iodonium salt which is a salt of an anion having an organic group and one or more atoms of P, B, Al, S, and Ga, and an aryl iodonium cation as the (B2) photoacid generator. The dental curable composition of the present disclosure may comprise only an aryl iodonium salt which is a salt of an anion having an organic group in which at least one H may be substituted with F and one or more atoms of P, B, Al, S, and Ga, and an aryl iodonium cation as the (B2) photoacid generator.

(C) Chemical Polymerization Initiator

The dental curable composition of the present disclosure contains a (C1) organic peroxide as the (C) chemical polymerization initiator in the case of not containing a (B1) photosensitizer and a (B2) photoacid generator which are the (B) photopolymerization initiator. Further, even when the (B1) photosensitizer and the (B2) photoacid generator which are the (B) photopolymerization initiator are contained, it is possible to contain the ($C_1$) organic peroxide as the (C) chemical polymerization initiator. The (C) chemical polymerization initiator is not particularly limited, and any known compound commonly used in the dental field may be used without any limitation.

<(C1) Organic peroxide>

Specific examples of an (C1) organic peroxide as the (C) chemical polymerization initiator used in the dental curable composition of the present disclosure include diacyl peroxides, peroxy esters, dialkyl peroxides, peroxy ketals, ketone peroxides, peroxy dicarbonates, and hydro peroxides. Specific examples of diacyl peroxides include acetyl peroxide, isobutyryl peroxide, benzoyl peroxide, decanoyyl peroxide, 3,5,5-trimethylhexanoyl peroxide, 2,4-dichlorobenzoyl peroxide, and lauroyl peroxide and the like. Specific examples of peroxyesters include α-cumylperoxy neodecanoate, t-butylperoxy neodecanoate, t-butylperoxy pivalate, 2,2,4-trimethylpentyl peroxy-2-ethyl hexanoate, t-amylperoxy-2-ethylhexanoate, t-butylperoxy-2-ethylhexanoate, di-t-butylperoxy isophthalate, di-t-butylperoxy hexahydro terephthalate, t-butylperoxy-3,3,5-trimethyl hexanoate, t-butylperoxy acetate, t-butylperoxy benzoate and t-butylperoxy maleric acid. Specific examples of dialkyl peroxides include di-t-butyl peroxide, dicumyl peroxide, t-butylcumyl peroxide, 2,5-dimethyl-2,5-di (t-butylperoxy) hexane, 1,3-bis (t-butylperoxy isopropyl) benzene, 2,5-dimethyl-2,5-di (t-butylperoxy)-3-hexyne and the like. Specific examples of peroxyketals include 1,1-di (t-butylperoxy) cyclohexane, 2,2-di (t-butylperoxy) butane, and n-butyl-4,4-(t-butylperoxy) parerate, 1,1-di (t-amylperoxy) cyclohexane and the like. Specific examples of ketone peroxides include methyl ethyl ketone peroxide, methyl isobutyl ketone peroxide, methyl cyclohexanone peroxide, cyclohexanone peroxide and the like. Specific examples of peroxydicarbonates include di-3-methoxyperoxy dicarbonate, di-2-ethylhexylperoxy dicarbonate, bis (4-t-butylcyclohexyl) peroxy dicarbonate, diisopropylperoxy dicarbonate, di-n-propylperoxy dicarbonate, di-2-ethoxyethylperoxy dicarbonate, diallylperoxy dicarbonate and the like. Specific examples of hydroperoxides include 2,5-dimethyl hexane-2,5-dihydroperoxide, diisopropylbenzene hydroperoxide, cumene hydroperoxide, t-butyl hydroperoxide and 1,1,3,3-tetramethyl butylhydroperoxide.

In the dental curable composition of the present disclosure, the exemplified organic peroxides may be used alone or in combination of two or more. Among these organic peroxides, diacyl peroxides, peroxyesters and hydroperoxides are preferable from the viewpoint of curability, for example, benzoyl peroxide, cumene hydroperoxide, 1,1,3,3-tetramethylbutyl hydroperoxide and t-butylperoxy-3,3,5-trimethyl hexanoate are preferable. The compounding amount of the organic peroxide as a chemical polymerization initiator is preferably set to 0.1 to 5 parts by mass, more preferably set to 0.3 to 3 parts by mass with respect to 100 parts by mass of the total amount of the (A) polymerizable monomer from the viewpoint of improving the curability. When the compounding amount of the organic peroxide is more than 5 parts by mass, it may be difficult to ensure sufficient operation time. On the other hand, when the compounding amount of the organic peroxide is less than 0.1 parts by mass, there is a case in which mechanical strength is insufficient.

(D) Polymerization Accelerator

The (D) polymerization accelerator which is used for the dental curable composition of the present disclosure is not particularly limited as long as it has polymerization promoting ability, and any known photopolymerization accelerator commonly used in the dental field may be used without any limitation. As the (D) polymerization accelerator, a primary to tertiary amine compound such as an aromatic amine compound, an aliphatic amine compound, a phosphine compound, an organometallic compound, a transition metal compound of the group 4 in the periodic table, a thiourea derivative, a sulfinic acid and a salt thereof, a borate compound, a sulfer-containing reductive inorganic compound, a nitrogen-containing reductive inorganic compound, a barbituric acid derivative, a triazine compound, a halogen compound and the like are used as a photopolymerization accelerator and/or a chemical polymerization accelerator. Although each compound can be used as an accelerator for photopolymerization and chemical polymerization, an amine compound, a phosphine compound, a sulfinic acid and a salt thereof, and an organometallic compound can be classified as a compound particularly used as a photopolymerization accelerator, and an aromatic amine compound, a phosphine compound, an organometallic compound, a transition metal compound of the group 4 in the periodic table, a thiourea derivative, a sulfinic acid and a salt thereof, a borate compound, a sulfur-containing reductive inorganic compound, a nitrogen-containing reductive inorganic compound, a barbituric acid derivative, a triazine compound and a halogen compound can be classified as a compound particularly used as a chemical polymerization accelerator.

Aromatic amine compound refers to a compound in which one or more H of ammonia ($NH_3$) is replaced with an aromatic ring. Aromatic amine compound in which one H of $NH_3$ is substituted with an aromatic ring is classified into an aromatic primary amine compound, aromatic amine compound in which one H of $NH_3$ is substituted with an aromatic ring and one H of remaining two H is substituted with an aromatic ring or an alkyl group is classified into an aromatic secondary amine compound, and aromatic amine compound in which one H of $NH_3$ is substituted with an aromatic ring and remaining two H are substituted with an aromatic ring or an alkyl group is classified into an aromatic tertiary amine compound.

Specific examples of the aromatic primary amine compound include aniline. Specific examples of the aromatic secondary amine compound include N-protected amino acid (ester) such as N-phenyl benzylamine, N-benzyl-p-anisidine, N-benzyl-o-phenetidine, N-phenylglycine ethyl and N-phenylglycine. Specific examples of the aromatic tertiary amine compound include N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylamino benzaldehyde, p-dimethylamino acetophenone, p-dimethylamino benzoic acid, p-dimethylamino benzoic acid ethyl ester, p-dimethylamino benzoic acid isoamyl estel, p-dimethylamino benzoic acid 2-butoxyethyl, p-dimethylamino benzoic acid 2-ethylhexyl, p-dimethylamino benzoic acid amino ester, N,N-dimethyl anthranic acid methyl ester, N,N-dihydroxyethyl aniline, N,N-diisopropanol aniline, p-N,N-dihydroxyethyl-toluidine, p-N,N-dihydroxypropyl-toluidine, p-dimethylamino phenyl alcohol, p-dimethylamino styrene, N,N-dimethyl-3,5-xylidine, 4-dimethylamino pyridine, N,N-dimethyl-α-naphthylamine, N,N-dimethyl-8-naphthylamine and the like. Among them, p-dimethylaminobenzoic acid ethyl ester is preferable.

The phosphine compound refers to a compound which is trisubstituted on P atom with organic groups, and the aromatic phosphine compound refers to a compound which is substituted on P atom with a phenyl group which may have one or more substituents. Specific examples of the phosphine compound include trimethylphosphine, tributylphosphine, trihexylphosphine, tri-n-octylphosphine, tricyclohexylphosphine, tri (2-thienyl) phosphine, diphenylpropyl phosphine, di-tert-butyl (3-methyl-2-butenyl) phosphine, methyldiphenyl phosphine, triphenyl phosphine, 2-(diphenylphosphino) styrene, 3-(diphenylphosphino) styrene, 4-(diphenylphosphino) styrene, allyldiphenyl phosphine, 2-(diphenylphosphino) benzaldehyde, 3-(diphenylphosphino) benzaldehyde, 4-(diphenylphosphino) benzaldehyde, 2-(phenylphosphine) benzoic acid, 3-(phenylphosphino) benzoic acid, 4-(phenylphosphino) benzoic acid, tris (2-methoxyphenyl) phosphine, tris (3-methoxyphenyl) phosphine, tris (4-methoxyphenyl) phosphine, 2-(diphenylphosphino) biphenyl, tris (4-fluorophenyl) phosphine, tri (o-trill) phosphine, tri (m-trill) phosphine, tri (p-trill) phosphine, 2-(dimethylamino) phenyldiphenyl phosphine, 3-(dimethylamino) phenyldiphenyl phosphine, 4-(dimethylamino) phenyldiphenyl phosphine, 2,2'-bis (diphenylphosphino) biphenyl, bis [2-(diphenylphosphino) phenyl] ether and the like. Among them, triphenylphosphine, 4-(phenylphosphino) benzoic acid, tri (o-tolyl) phosphine, tri (m-tolyl) phosphine and tri (p-tolyl) phosphine are preferable.

Aliphatic amine compounds refer to compounds in which one or more H of ammonia ($NH_3$) are substituted with alkyl group. As for the alkyl group, $CH_3$— and —$CH_2$— are classified as a primary alkyl group, the one in which one H of —$CH_2$— is substituted with a substituent is classified as a secondary alkyl group, and the one in which two H of —$CH_2$— are substituted with substituents is classified as a tertiary alkyl group. Aliphatic amine in which one H of $NH_3$ is substituted with an alkyl group is classified into an aliphatic primary amine compound, aliphatic amine compound in which two H of $NH_3$ are substituted with an alkyl group is classified into an aliphatic secondary amine compound, and aliphatic amine compound in which three H of $NH_3$ are substituted with an alkyl group is classified into an aliphatic tertiary amine compound.

Specific examples of the aliphatic primary amine compound include amino acid or amino acid ester such as benzhydrylamine, triphenylmethylamine and glycine. Specific examples of the aliphatic secondary amine compound include dibenzylamine, N-benzyl-1-phenylethylamine, bis (1-phenylethyl) amine, bis (4-cyanobenzyl) amine, N-benzyl protected amino acid and N-benzyl protected amino acid ester. Specific examples of the aliphatic tertiary amine compound include tributylamine, tripropylamine, triethylamine, N,N-dimethyl hexylamine, N,N-dimethyl dodecylamine, N,N-dimethyl stearylamine, N-[3-(dimethylamino) propyl] acrylamide, N,N-dimethyl formamide dimethylacetal, N,N-dimethylacetamide dimethylacetal, N,N-dimethylformamide diethylacetal, N,N-dimethylformamide dipropylacetal, N,N-dimethylformamide di-tert-butylacetal, 1-(2-hydroxyethyl) ethyleneimine, N,N-dimethyl ethanolamine, N,N-dimethyl isopropanolamine, N,N-diisopropyl ethanolamine, N-methyl diethanolamine, N-ethyl diethanolamine, N-ethyl diethanolamine, N-butyl diethanolamine, N-lauryl diethanolamine, N-stearyl diethanolamine, triethanolamine, triisopropanolamine, tribenzylamine, dibenzylglycine ethylester, N'-(2-hydroxyethyl)-N,N,N'-trimethylethylene diamine, 2-(dimethylamino)-2-methyl-1-propanol, N,N-dimethyl-2,3-dihydroxy propylamine, N,N-diethylethanolamine, 1-methyl-3-pyrrolidinol, 1-(2-hydroxyethyl) pyrrolidine, 1-isopropyl-3-pyrrolidinol, 1-piperidin ethanol, 2-[2-(dimethylamino) ethoxy] ethanol, N,N-dimethylglycine, N,N-dimethylglycine methyl, N,N-diethylglycine methyl, N,N-dimethylglycine ethyl, N,N-diethylglycine sodium, 2-(dimethylamino) ethylacetate, N-methylimimino diacetic acid, N,N-dimethylamino ethylacrylate, N,N-diethylamino ethylmethacrylate, N,N-diisopropylamino ethylmethacrylate, N,N-dibutylamino ethylmethacrylate, N,N-dibenzylamino ethylmethacrylate, 3-dimethylamino propionitrile, tris (2-cyanoethyl) amine, N,N-dimethyl allylamine, N,N-diethyl allylamine and triallylamine.

Specific examples of the above organic metal compound include an organic metal compound containing scandium (Sc), titanium (Ti), vanadium (V), manganese (Mn), iron (Fe), cobalt (Co), nickel (Ni), copper (Cu), tin (Sn), zinc (Zn) an/or zirconia (Zr), and an organic metal compound containing tin (Sn), vanadium (V) and/or copper (Cu) is preferable. Specific examples of the organic metal compound containing tin (Sn) include dibutyl-tin-diacetate, dibutyl-tin-dimaleate, dioctyl-tin-dimaleate, dioctyl-tin-dilaurate, dibutyl-tin-dilaurate, dioctyl-tin-diversate, dioctyl-tin-S,S'-bis-isooctyl mercapto acetate, tetramethyl-1,3-diacetoxy distanoxane and the like. Specific examples of the organic metal compound containing vanadyl (V) include acetylacetone vanadium, divanadium tetraoxide, vanadyl acetylacetonate, vanadyl stearate oxide, vanadyl oxalate, vanadyl sulphate, oxobis (1-phenyl-1,3-butandionate) vanadium, bis (maltlate) oxovanadium, vanadium pentoxide and sodium metavanadate. Specific examples of the organic metal compound containing copper (Cu) include copper acetylacetone, copper naphthenate, copper octylate, copper stearate and copper acetate.

Among these, a trivalent or tetravalent vanadium compound and a divalent copper compound are preferable. Among them, because of having higher polymerization accelerating ability, a trivalent or tetravalent vanadium compound is more preferable, and a tetravalent vanadium compound is most preferable. A plurality of kinds of these transition metal compounds in the period 4 in the periodic table may be used in combination, if necessary. The compounding amount of transition metal compound is preferably 0.0001 to 1 parts by mass with respect to 100 parts by mass of the total amount of the (A) polymerizable monomer. When the compounding amount is less than 0.0001 parts by mass, there is a case where the polymerization accelerating effect is insufficient, and when the compounding amount exceeds 1 part by mass, there is a case where it causes discoloration or gelation of the dental curable composition and the storage stability is lowered.

Specific examples of the thiourea derivatives include dimethylthiourea, diethylthiourea, tetramethylthiourea, (2-pyridyl) thiourea, N-methylthiourea, ethylenethiourea, N-allylthiourea, N-allyl-N'-(2-hydroxyethyl) thiourea, N-benzylthiourea, 1,3-dicyclohexyl thiourea, N,N'-diphenylthiourea, 1,3-di (p-tolyl) thiourea, 1-methyl-3-phenylthiourea, N-acetylthiourea, N-benzoylthiourea, diphenylthiourea, dicyclohexylthiourea and the like. Among these, (2-pyridyl) thiourea, N-acetylthiourea and N-benzoylthiourea are preferable. A plurality of kinds of these thiourea derivatives can be used in combination, if necessary. The compounding amount of the thiourea derivative is preferably 0.1 to 5 parts by mass with respect to 100 parts by mass of the total amount of the (A) polymerizable monomers. When the compounding amount is less than 0.1 parts by mass, there is a case where the ability as a polymerization accelerator is insufficient, and when the compounding amount exceeds 5 parts by mass, the storage stability may be lowered.

Examples of sulfinic acid and its salt include p-toluene sulfinic acid, sodium p-toluene sulfinate, potassium p-toluene sulfinate, lithium p-toluene sulfinate, calcium p-toluene sulfinate, benzenesulfinic acid, sodium benzene sulfinate, potassium benzene sulfinate, lithium benzenesulfinate, calcium benzenesulfinate, 2,4,6-trimethyl benzenesulfinic acid, sodium 2,4,6-trimethyl benzenesulfinate, potassium 2,4,6-trimethyl benzenesulfinate, lithium 2,4,6-trimethyl benzenesulfinate, calcium 2,4,6-trimethyl benzenesulfinate, 2,4,6-triethyl benzenesulfinic acid, sodium 2,4,6-triethyl benzenesulfinate, potassium 2,4,6-triethyl benzenesulfinate, lithium 2,4,6-triethyl benzenesulfinate, calcium 2,4,6-triethyl benzenesulfinate, 2,4,6-triisopropyl benzenesulfinic acid, sodium 2,4,6-triisopropyl benzenesulfinate, potassium 2,4,6-triisopropyl benzenesulfinate, lithium 2,4,6-triisopropyl benzenesulfinate, calcium 2,4,6-triisopropyl benzenesulfinate and the like. Among them, sodium benzenesulfinate, sodium p-toluenesulfinate, and sodium 2,4,6-triisopropyl benzenesulfinate are particularly preferable.

As the borate compound, specific examples of the borate compound having one aryl group in one molecule include trialkylphenylboron, trialkyl (p-chlorophenyl) boron, trialkyl (p-fluorophenyl) boron, trialkyl (3,5-bistrifluoro methyl) phenyl boron, trialkyl [3,5-bis (1,1,1,3,3,3-hexafluoro-2-methoxy-2-propyl) phenyl] boron, trialkyl (p-nitrophenyl) boron, trialkyl (m-nitrophenyl) boron, trialkyl (p-butylphenyl) boron, trialkyl (m-butylphenyl) boron, trialkyl (p-butyloxyphenyl) boron, trialkyl (m-butyloxyphenyl) boron, trialkyl (p-octyloxyphenyl) boron and trialkyl (m-octyloxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having two aryl groups in one molecule include dialkyl diphenylboron, dialkyl di (p-chlorophenyl) boron, dialkyl di (p-fluorophenyl) boron, dialkyl di (3,5-bistrifluoro methyl) phenyl boron, dialkyl di [3,5-bis (1,1,1,3,3,3-hexafluoro-2-methoxy-2-propyl) phenyl] boron, dialkyl di (p-nitrophenyl) boron, dialkyl di (m-nitrophenyl) boron, dialkyl di (p-butylphenyl) boron, dialkyl di (m-butylphenyl) boron, dialkyl di (p-butyl oxyphenyl) boron, dialkyl di (m-butyl oxyphenyl) boron, dialkyl di (p-octyl oxyphenyl) boron and dialkyl di (m-octyl oxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having three aryl groups in one molecule include monoalkyl triphenylboron, monoalkyl tri (p-chlorophenyl) boron, monoalkyl tri (p-fluorophenyl) boron, monoalkyl tri (3,5-bistrifluoro methyl) phenyl boron, monoalkyl tri [3,5-bis (1,1,1,3,3,3-hexafluoro-2-methoxy-2-propyl) phenyl] boron, monoalkyl tri (p-nitrophenyl) boron, monoalkyl tri (m-nitrophenyl) boron, monoalkyl tri (p-butylphenyl) boron, monoalkyl tri (m-butylphenyl) boron, monoalkyl tri (p-butyl oxyphenyl) boron, monoalkyl tri (m-butyl oxyphenyl) boron, monoalkyl tri (p-octyl oxyphenyl) boron and monoalkyl tri (m-octyl oxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having four aryl groups in one molecule include tetraphenylboron, tetra kis (p-chlorophenyl) boron, tetra kis (p-fluorophenyl) boron, tetra kis (3,5-bistrifluoro methyl) phenyl boron, tetra kis [3,5-bis (1,1,1,3,3,3-hexafluoro-2-methoxy-2-propyl) phenyl] boron, tetra kis (p-nitrophenyl) boron, tetra kis (m-nitrophenyl) boron, tetra kis (p-butylphenyl) boron, tetra kis (m-butylphenyl) boron, tetra kis (p-butyl oxyphenyl) boron, tetra kis (m-butyl oxyphenyl) boron, tetra kis (p-octyl oxyphenyl) boron, tetra kis (m-octyl oxyphenyl) boron, (p-fluorophenyl) triphenylboron, (3,5-bis trifluoromethyl) phenyl triphenylboron, (p-nitrophenyl) triphenylboron, (m-butyl oxyphenyl) triphenylboron, (p-butyl oxyphenyl) triphenylboron, (m-octyl oxyphenyl) triphenylboron and (p-octyl oxyphenyl) triphenylboron, and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like).

Among these aryl borate compounds, it is more preferable to use a borate compound having 3 or 4 aryl groups in one molecule from the viewpoint of storage stability. Further, these aryl borate compounds can be used alone or as a mixture of two or more.

Examples of sulfur-containing reductive inorganic compound include sulfites, bisulfites, pyrosulfites, thiosulfates, thionates and dithionite. Specific examples include sodium sulfite, potassium sulfite, calcium sulfite, ammonium sulfite, sodium bisulfite, potassium bisulfite, 3-mercaptopropyl trimethoxysilane, 2-mercaptobenzoxazole, decanethiol, thiobenzoic acid and the like.

Examples of nitrogen-containing reductive inorganic compound include nitrites, and specific examples include sodium nitrite, potassium nitrite, calcium nitrite, ammonium nitrite and the like.

Specific examples of barbituric acid derivative include salts (alkali metals or alkaline earth metals are preferred) of barbituric acid, 1,3-dimethyl barbituric acid, 1,3-diphenyl barbituric acid, 1,5-dimethyl barbituric acid, 5-butyl barbituric acid, 5-ethyl barbituric acid, 5-isopropyl barbituric acid, 5-cyclohexyl barbituric acid, 1,3,5-trimethyl barbituric acid, 1,3-dimethyl-5-ethyl barbituric acid, 1,3-dimethyl-n-butyl barbituric acid, 1,3-dimethyl-5-isobutyl barbituric acid, 1,3-dimethyl barbituric acid, 1,3-dimethyl-5-cyclopentyl barbituric acid, 1,3-dimethyl-5-cyclohexyl barbituric acid 1,3-dimethyl-5-phenyl barbituric acid, 1-cyclohexyl-1-ethyl barbituric acid, 1-benzyl-5-phenyl barbituric acid, 5-methyl barbituric acid, 5-propyl barbituric acid, 1,5-diethyl barbituric acid, 1-ethyl-5-methyl barbituric acid, 1-ethyl-5-isobutyl barbituric acid, 1,3-diethyl-5-butyl barbituric acid, 1-cyclohexyl-5-methyl barbituric acid, 1-cyclohexyl-5-ethyl barbituric acid, 1-cyclohexyl-5-octyl barbituric acid, 1-cyclohexyl-5-hexyl barbituric acid, 5-butyl-1-cyclohexyl barbituric acid, 1-benzyl-5-phenyl barbituric acid and thiobarbituric acids. Specifically, the salts of these barbituric acids include sodium 5-butyl barbiturate, sodium 1,3,5-trimethyl barbiturate, sodium 1-cyclohexyl-5-ethyl barbiturate and the like.

Specific examples of the halogen compound include dilauryl dimethyl ammonium chloride, lauryl dimethyl benzyl ammonium chloride, benzyl trimethyl ammonium chloride, tetramethyl ammonium chloride, benzyl dimethyl acetyl ammonium chloride, dilauryl dimethyl ammonium bromide and the like.

The compounding amount of the (D) polymerization accelerator is preferably 0.2 to 10 parts by mass, more preferably 0.5 to 5 parts by mass, with respect to 100 parts by mass of the total amount of the (A) polymerizable monomer contained in the dental curable composition. When the compounding amount is less than 0.2 parts by mass, there is a case where the mechanical strength is insufficient. When the compounding amount is more than 10 parts by mass, although it has sufficient curability, the sensitivity to light is shortened, and discoloration such as browning of the cured body may increase, and therefore it is not preferable.

There is no problem even if these (B1) photosensitizers, (B2) photoacid generators, (C1) organic peroxides and (D) polymerization accelerators are subjected to a secondary treatment such as finely pulverization, adsorption on a carrier and encapsulation in a microcapsule, if necessary. Furthermore, these photo polymerization initiators may be used not only singly but also in combinations of two or more, regardless of the polymerization manner or the polymerization method.

(E) Filler

As the (E) filler used in the present disclosure, a known filler commonly used can be used without any limitation.

The type of the (E) filler is not limited as long as it is a known filler, and a filler suitable for the application can be compounded, and it is preferable that a filler such as an inorganic filler, an organic filler, an organic-inorganic composite filler and an ion sustained release glass is compounded. In the dental curable composition of the present disclosure, the filler described in the specific example may be used alone, or two or more kinds of fillers may be used in combination.

As the above described inorganic filler, the chemical composition is not particularly limited, but specific examples include silicon dioxide, alumina, titania, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass and the like. Particularly, barium fluoroaluminosilicate glass, strontium fluoroaluminosilicate glass, fluoroaluminosilicate glass and the like, which are used in dental glass ionomer cement, resin reinforced glass ionomer cement and resin cement and the like, can also be suitably used. The fluoroaluminosilicate glass as used herein has a basic structure of silicon oxide and aluminum oxide and contains an alkali metal for introducing non-crosslinked oxygen. The fluoroaluminosilicate glass further has an alkaline earth metal including strontium and fluorine as modified/coordinated ions. The fluoroaluminosilicate glass may be also a composition in which a lanthanoid series element is incorporated into the skeleton in order to impart further radiopacity. This lanthanoid series element also participates in the composition as a modified/coordinated ion.

As the inorganic filler, an inorganic fine particle having an average primary particle diameter of 0.1 to 50 nm can be contained. Specific examples include alumina fine particle and silica fine particle. When such inorganic fine particle is mixed, it can be expected to improve mechanical property and exhibit rheological property. Further, it is preferably hydrophobized with a silane coupling agent or the like. The primary particle diameter indicates the diameter of one particle (primary particle) constituting the powder. In the present disclosure, the average particle diameter may be, for example, an average particle diameter calculated based on a volume-based grain size distribution measured by a laser diffraction type particle size distribution measuring device or the like, and may be measured by, for example, a laser diffraction type grain size measuring apparatus (Microtrac MT3300EXII: NIKKISO Co., Ltd.). In addition, the primary particle diameter can be measured by dynamic light scattering particle size measurement and can be measured by using electron micrographs for the case that primary particles are strongly aggregated to form secondary particles.

Specific examples of the organic filler include polymers such as polymethyl methacrylate, polyethyl methacrylate, methyl methacrylate-ethyl methacrylate copolymer, ethyl methacrylate-butyl methacrylate copolymer, methyl methacrylate-trimethylolpropane methacrylate copolymer, polyvinylchloride, polystyrene, chlorinated polyethylene, nylon, polysulfone, polyethersulfone and polycarbonate.

Specific examples of the organic/inorganic composite filler include one obtained by covering the surface of a filler with a polymerizable monomer by polymerization, one obtained by mixing a filler and a polymerization monomer and polymerizing the monomer and thereafter grinding the resultant to a proper particle size, one obtained by dispersing a filler in a polymerizable monomer in advance for emulsion polymerization or suspension polymerization, one obtained by spray-drying a polymerizable monomer and a solvent which are dispersed with a filler in advance and polymerizing, and one obtained by spray-drying a solvent which is dispersed with a filler in advance, impregnating a polymerizable monomer and polymerizing, but are not limited thereto at all.

(E1) Surface-Treated Basic Filler

As the (E1) surface-treated basic filler that can be used for the present disclosure, a known filler commonly used in a dental composite material can be used. The (E1) surface-treated basic filler of the present disclosure refers a filler in which a dispersion of 1.0 g of the filler in a mixed solution of 40 g of distilled water and 10 g of ethanol has pH-value of 7.5 or more, preferably in the range from 7.5 to 10.0, more preferably in the range from 7.7 to 9.0, furthermore preferably in the range from 8.0 to 9.0, after stirring for 1 hour.

In the dental curable composition of the present disclosure, improvement of storage stability is expected by containing the (E1) surface-treated basic filler. There was a problem with storage stability in the case of coexisting a compound used as a polymerization initiator and a basic filler for a long period of time. By treating the surface with a surface treatment agent in advance, the (E1) surface-treated basic filler used in the present disclosure can improve storage stability in coexisting with the polymerization initiator. Among the polymerization initiators, particularly high storage stability is exhibited in the case of coexisting with compound such as a photoacid generator and an organic peroxide. Further, since the (E1) surface-treated basic filler has an appropriate basicity, it is expected to neutralize the acid derived from, for example, a photoacid generator or a polymerizable monomer having an acidic group after long-term storage. Therefore, it is considered that good storage stability can be expected by suppressing the hydrolysis of the composition. Good storage stability can be expected in both pre-curing form and post-curing form. Furthermore, when the surrounding of the cured product of the dental curable composition is under acidic condition, it can be expected to exhibit an acid-neutralizing ability capable of neutralizing acid. Since demineralization of tooth substance composed of enamel or dentin proceeds under an acidic condition, an effect of suppressing demineralization is expected by neutralization of acid.

Types of basic filler include an inorganic filler, an organic filler, an organic-inorganic composite filler and the like, and these fillers can be used not only singly but also in combinations of a plurality thereof regardless of the types of the fillers.

The filler that can be used as a basic filler is not particularly limited, but is preferably a compound selected from the group consisting of an oxide, a hydroxide, a fluoride, a carbonate, a silicate which contain a metal element of Group 2 to 13 in the periodic table and a mixture thereof, a polyvalent metal alkoxide, a polyvalent metal hydride, and an alkyl polyvalent metal. The valence of the polyvalent metal compound is not particularly limited and may be divalent or higher.

Specific examples of the basic filler include alumina, calcia and magnesia as oxides, calcium hydroxide, magnesium hydroxide and strontium hydroxide as hydroxides, magnesium fluoride, calcium fluoride, barium fluoride, strontium fluoride, aluminum fluoride, titanium fluoride, lanthanum fluoride, zirconium fluoride and zinc fluoride as fluorides, magnesium carbonate, strontium carbonate, calcium carbonate, barium carbonate, aluminum carbonate, lanthanum carbonate, yttrium carbonate, zirconium carbonate and zinc carbonate as carbonates, calcium silicate, aluminum silicate, fluoroaluminosilicate glass, fluoroaluminoborosilicate glass and other silicate glasses as silicates. Among them, fluoroalumino silicate glass containing strontium and/or calcium ion and fluoroalumino borosilicate glass containing strontium and/or calcium ion are preferable. From the viewpoint of the storage stability, the composition range of the filler is preferably 15 to 35% by mass of $SiO_2$, 15 to 30% by mass of $Al_2O_3$, 20 to 45% by mass of SrO, 0 to 15% by mass of $P_2O_5$, 5 to 15% by mass of F, 0 to 10% by mass of $Na_2O$, 0 to 20% by mass of B203, and 0 to 10% by mass of CaO. Particularly preferable filler has the total content of $Al_2O_3$ and SrO within a range from 40 to 60% by mass in the above composition range. When the total content of $Al_2O_3$ and SrO is less than 40% by mass, there is a case that the high basicity condition cannot be maintained and the color tone stability is lowered. When the total content of $Al_2O_3$ and SrO is more than 60% by mass, there is a case that the basicity of the filler is excessive.

The organic group in the polyvalent metal alkoxide is not particularly limited, and examples thereof include methyl, ethyl, propyl, isopropyl, butyl, isobutyl, pentyl, hexyl, cyclohexyl, heptyl, 2-ethylhexyl, octyl and the like, and an alkyl group having 4 or less carbon atoms is preferable. The alkyl group in the alkyl polyvalent metal is not particularly limited, and examples thereof include an alkyl group having 1 to 20 carbon atoms. It should be noted that these may be used alone or in combination of two or more.

Specific examples of the compound of the multivalent metal alkoxide include magnesium diethoxide, calcium diisopropoxide, barium diisopropoxide, aluminum triethoxide, aluminum triisopropoxide, gallium triethoxide, scandium triisopropoxide, lanthanum triisopropoxide, ytterbium triisopropoxide, yttrium tetraisopropoxide, cerium tetraisopropoxide, samarium tetraisopropoxide, titanium tetramethoxide, titanium tetraethoxide, titanium tetraisopropoxide, titanium tetrabutoxide, zirconium tetraisopropoxide, hafnium tetraisopropoxide, tantalum (V) ethoxide, chromium (III) isopropoxide, molybdenum (V) ethoxide, tungsten (VI) isopropoxide, iron(III) ethoxide, copper (II) ethoxide, zinc (II) ethoxide.

Specific examples of the compound of the polyvalent metal hydride include calcium hydride, aluminum hydride, zirconium hydride and the like, and specific examples of compound of the alkyl polyvalent metal include, for example, diethylmagnesium and trimethylaluminum.

The shape of the basic filler is not particularly limited, and an amorphous or a spherical shape can be used. The average particle diameter of the basic filler is preferably 0.01 μm to 50 μm, more preferably 0.1 μm to 30 μm, still more preferably 0.5 μm to 20 μm, and more preferably 0.5 μm to 10 μm.

The basic filler having an average particle diameter of 0.01 μm to 50 μm can be obtained by wet pulverizing an inorganic particle as a raw material of the basic filler. No special method is required in such wet pulverization and method commonly used in industry can be adopted and used. For example, the raw material of an inorganic particle can be pulverized by using a container driving medium mill such as a ball mill and a vibration mill, a grinding medium stirring mill such as an attritor, a sand grinder, aniler mill and tower mill. As the medium, water or a mixed solvent of water and a water-soluble organic solvent can be used. Examples of water-soluble organic solvent include alcohols, ketones such as acetone, and ethers. When these water-soluble organic solvents are used, there is a case that the cohesive force of the solidified product after drying is weakened, pulverization becomes easy. The condition of wet pulverization varies depending on the size and hardness of the raw material inorganic particles, the charged amount, the added amount of water or aqueous medium, the type of pulverizer and the like, but the condition containing the pulverization operation time can be selected depending on the required average particle diameter of the inorganic fine particle, appropriately.

The compounding amount of the (E) filler in the dental curable composition is preferably 10 to 1000 parts by mass with respect to 100 parts by mass of the total amount of the (A) polymerizable monomer, and in the case that formability and the like are taken into consideration, the compounding amount is preferably less than 400 parts by mass. When the compounding amount of the filler is less than 10 parts by mass, there is a case that the effect of improving the mechanical strength and of exhibiting the thixotropy by compounding the filler becomes poor. When the compounding amount is more than 1000 parts by mass, the paste property of the composition becomes hard and there is a case that it is difficult to handle. However, depending on the type of the filler and the surface treatment condition of the filler, there is a case where 1000 parts by mass or more is contained. For example, it refers to the case where the filler has a high specific gravity, the amount of the surface treatment agent to the filler is large, and the case where a surface treatment agent having a good affinity with the polymerizable monomer is used. The composition of the present disclosure exhibits an effect regardless of the compounding amount of the filler. In addition, in the case of a dental curable composition packaged in a plurality, that is two or more agents, since a mixing operation is required, 10 to 400 parts by mass with respect to 100 parts by mass of the total amount of the (A) polymerizable monomer is preferable.

The compounding amount of the (E1) surface-treated basic filler in the dental curable composition of the present disclosure is preferably 10 to 500 parts by mass with respect to 100 parts by mass of the total amount of the (A) polymerizable monomer, and more preferably 20 to 500 parts by mass. When the compounding amount is less than 10 parts by mass, there is a case that the effect of improving storage stability is not exhibited. When the compounding amount is more than 500 parts by mass, the paste property of the composition becomes hard and there is a case that it is difficult to handle. In the case of a dental curable composition packaged in a plurality, that is two or more agents, since a mixing operation is required, 10 to 500 parts by mass with respect to 200 parts by mass of the total amount of the (A) polymerizable monomer is preferable, and 10 to 400 parts by mass is more preferable.

(F) Surface Treatment Agent

The (E) filler can be treated with (F) Surface treatment agent represented by a surfactant, a polymer and a silane coupling material in order to improve the affinity to the polymerizable monomer, the dispersability in the polymerizable monomer and the mechanical strength and water resistance of the cured product. The surface treatment agent and the surface treatment method are not particularly limited, and known methods can be adopted without limitation.

As a silane coupling material used for surface treatment of the filler, methyltrimethoxysilane, methyltriethoxysilane, methyltrichlorosilane, dimethyldichlorosilane, trimethylchlorosilane, vinyltrichlorosilane, vinyltriethoxysilane, vinyltris (2-methoxyethoxy) silane, 3-methacryloyloxypropyl trimethoxysilane, 3-chloropropyl trimethoxysilane, 3-glycidoxypropyl trimethoxysilane, 3-(meth) acryloxypropyl trimethoxysilane, 8-(meth) acryloxyoctyl trimethoxysilane, 11-(meth) acryloxiundecyl trimethoxysilane, 4,4-diethoxy-17-oxo-3,16-dioxa-18-aza-4-cilaicosan-20-yl (meth) acrylate, 2-methyl-2-((((11-(triethoxysilyl) undecyl) oxy) carbonyl) amino) propane-1,3-diyldi (meth) acrylate, 4,4-diethoxy-17-oxo-3,16,21-trioxa-18-aza-4-silatricosan-23-yl (meth) acrylate and hexamethyldisilazane and the like are preferable. In addition to the silane coupling material, surface treatment of the filler can be performed by a method using a titanate coupling material or an aluminate coupling material.

The silane coupling material used for the surface treatment of the filler and the silane coupling material as the (A) polymerizable monomer are used separately. Since the silane coupling material having a polymerizable group used for surface treatment of the filler reacts with the filler, it cannot be expected to exhibit adhesive property to glass ceramic and the like. Therefore, when a silane coupling material is compounded as the (A) polymerizable monomer for imparting adhesive property to glass ceramic and the like, it is compounded separately from the surface treatment agent.

The acidic polymer that can be used for surface treatment of the filler is a copolymer or homopolymer of a polymerizable monomer having, as an acidic group, an acidic group such as a phosphoric acid residue, a pyrophosphoric acid residue, a thiophosphoric acid residue, a carboxylic acid residue or a sulfonic acid residue. Specific examples of these polymerizable monomers having an acidic group include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, 4-(meta) acryloyloxy ethoxycarbonyl phthalic acid, 4-(meta) acryloyloxy ethoxycarbonyl phthalic anhydride, 5-(meta) acryloylamino pentylcarboxylic acid, 11-(meth) acryloyloxy-1,1-undecane dicarboxylic acid, 2-(meta) acryloyloxyethyl dihydrogen phosphate, 10-(meta) acryloyloxydecyl dihydrogen phosphate, 20-(meta) acryloyloxyeicosil dihydrogen phosphate, 1,3-di (meth) acryloyloxypropyl-2-dihydrogen phosphate, 2-(meta) acryloyloxyethyl phenyl phosphate, 2-(meta) acryloyloxyethyl-2'-bromoethyl phosphate, (meta) acryloyloxyethyl phenylphosphonate, [2-(meth) acryloyloxyethyl] pyrophosphate, 2-(meta) acryloyloxyethyl dihydrogen dithiophosphosphate and 10-(meta) acryloyloxydecyl dihydrogen thiophosphate.

The treatment amount of the surface treatment agent with respect to the filler is preferably 0.1 to 40 parts by mass, more preferably 1 to 30 parts by mass with respect to 100 parts by mass of the filler before treatment. When the amount is less than 0.1 parts by mass, there is a case that improvement in mechanical property and paste property expected of surface treatment agent are not remarkable. When the amount is more than 40 parts by mass, the amount of the surface treatment agent relative to the filler is too large, and therefore there is a case that deterioration of mechanical property occurs.

(F1) Surface Treatment Agent Represented by the Formula (1) and/or Condensate Thereof The above described (E1) surface-treated basic filler is surface-treated with (F1) surface treatment agent represented by the formula (1) and/or condensate thereof.

That is, the dental curable composition of the present disclosure contains the (E1) surface-treated basic filler surface-treated with the (F1) surface treatment agent represented by the formula (1) and/or condensate thereof.

[Formula (1)]

[Chemical Formula 2]

(In the formula, M is a metal atom selected from Si, Ti, Zr, and Al, X is H, OH or a hydrolyzable group, and may be the same or different from each other. In the case that M is Si, Ti or Zr, n is 4. In the case that M is Al, n is 3.)

The hydrolyzable group in the (F1) surface treatment agent represented by the formula (1) and/or condensate thereof refers to an alkoxy group or a halogen group, and specific examples include methoxy group, ethoxy group, isopropoxy group, n-butoxy group, t-butoxy group, and chloro group. From the viewpoint of handling, alkoxy group is preferable, and methoxy group and ethoxy group are more preferable. By using the (E1) surface-treated basic filler surface-treated with the (F1) surface treatment agent represented by the formula (1) and/or condensate thereof, storage stability in the case of being used in a dental curable composition is improved.

It is preferable to heat the (F1) surface treatment agent represented by the formula (1) and/or condensate thereof to 130° C. or higher during the surface treatment process for the filler. An improvement in storage stability can be expected by heating to high temperature of 130° C. or higher. It is considered that the reason is that the reaction between the basic filler and the surface treatment agent progresses easily. On the other hand, when the temperature is less than 130° C., there is a case that the improvement of the storage stability is not sufficient. Even when the temperature is less than 100° C., it can be expected to improve the storage stability in the case of compounding in a dental curable composition by exposing to the temperature for a long time of several days. However, a long period of time is required for preparation and therefore it is not preferable.

It is preferable that the (F1) surface treatment agent represented by the formula (1) and/or condensate thereof is calcined at 400° C. or less during the surface treatment of the filler. When the temperature exceeds 400° C., there is a case that the acid-neutralizing ability is not sufficiently exhibited in the case of immersing the cured product of the dental curable composition in an acidic aqueous solution. When the oral cavity environment is under acidic condition for a long period of time, demineralization of tooth substance progresses. In particular, it is remarkable in the restoration part of the tooth, and secondary caries and the like may occur in such a case. The acid-neutralizing ability of the dental curable composition refers to the ability to increase pH-value of the surrounding of the curable dental composition when pH-value of the surrounding is under acidic condition. For specific example of the method for measuring the acid neutralization ability, pH-value is measured for a cured product of the dental curable composition having a diameter of 15 mm and a thickness of 1 mm after immersing for 24 hours in 5 mL of an aqueous lactic acid solution which has pH-value of 4.0, and the acid-neutralizing ability of the dental curable composition refers pH-value of 4.5 or more, more preferably 5.0 or more in result of measurement result. Suppression of tooth demineralization can be expected by using a dental curable composition having an acid-neutralizing ability.

The (F1) surface treatment agent represented by the formula (1) and/or condensate thereof does not have a polymerizable group. When a polymerizable group is contained, it causes stain of the filler or impurity that adversely affect the property of the dental curable composition in the case of exposing long-term to high temperature of 130° C. or higher, and therefore there is a case that good storage stability is not exhibited. This tendency is remarkable in those having a polymerizable group among organic groups. Moreover, when a plurality of organic groups having steric hindrance such as polymerizable group are contained, there is a case that the surface of the filler is not uniformly surface-treated. On the other hand, a hydrolyzable group containing an organic group is removed as a volatile component before remaining on the surface of the filler, or can be washed as a free component, and therefore cause no problem.

Among the (F1) surface treatment agent represented by the formula (1) and/or condensate thereof used for preparing the (E1) surface-treated basic filler in the present disclosure, specific examples of those corresponding to formula (1) include tetramethoxysilane, tetraethoxysilane, tetrapropoxysilane, tetrabutoxysilane, tetrakis (2-ethylhexyloxy) silane, tetraphenoxysilane, tetrachlorosilane, silicon hydroxide (silicon oxide hydrate), zirconium tetra-n-butoxide, zirconium tetra-t-butoxide, zirconium tetrapropoxide, tetraethyl orthotitanate, tetraisopropyl orthotitanate, dichlorotitanium diisopropoxide, tetrabutyl orthotitanate, tetraisobutyl orthotitanate, tetrakis (2-ethylhexyl) orthotitanate, aluminum ethoxide, aluminum isopropoxide, aluminium-sec-butoxide and aluminum-tert-butoxide, and tetramethoxysilane and tetraethoxysilane are preferable.

Among the (F1) surface treatment agent represented by the formula (1) and/or condensate thereof, examples include a partial condensate obtained by partially hydrolyzing and condensing tetramethoxysilane or tetraethoxysilane. Specific examples include a partial condensate of tetramethoxysilane, tetraethoxysilane, tetrapropoxysilane, tetrabutoxysilane, tetrakis (2-ethylhexyloxy) silane, trimethoxychlorosilane, triethoxychlorosilane, triisopropoxychlorosilane, trimethoxyhydroxysilane, diethoxydichlorosilane, tetraphenoxysilane, tetrachlorosilane, silicon hydroxide (silicon oxide hydrate), zirconium tetra-n-butoxide, zirconium tetra-t-butoxide, zirconium tetrapropoxide, tetraethyl orthotitanate, tetraisopropyl orthotitanate, dichlorotitanium diisopropoxide, tetrabutyl orthotitanate, tetraisobutyl orthotitanate, tetrakis (2-ethylhexyl) orthotitanate, aluminum ethoxide, aluminum isopropoxide, aluminium-sec-butoxide and aluminum-tert-butoxide. These compounds can be condensed singly or in combination. The partial condensate refers to a state in which any of one or more of a hydrolyzable group, an OH group, or H, which are bondable, is sufficiently present because not all the bonds in the surface treatment agent form covalent bonds and partial condensation reaction occurs in forming a condensate by hydrolysis and/or dehydration condensation of the surface treatment agent represented by formula (1). Furthermore, all or part of the functional groups that bind to the metal atom in the condensate may be OH groups. When the condensate does not have hydrolyzable group, the generation of volatile substances can be reduced.

Further, in film forming, these coupling agents may be added with an organosilane compound having no polymerizable group which is used in combination with the (F1) surface treatment agent represented by the formula (1) and/or condensate thereof. Specific examples of an organosilane compound include methyltrimethoxysilane, ethyltrimethoxysilane, methoxytripropylsilane, propyltriethoxysilane and methyltrichlorosilane. Methyltrimethoxysilane and ethyltrimethoxysilane are particularly preferable. Such a compound can be used singly or in combination. However, since an organic group is present in the film of the coupling agent condensate, there is a possibility in these compound that strain occurs during the formation of the film of the coupling agent condensate to cause problem in mechanical strength. In addition, during the formation of the film of the coupling agent condensate, an alkoxide compound, a halide, a hydrated oxide, a nitrate and a carbonate of other metal may be added and used in combination with the (F1) surface treatment agent represented by the formula (1) and/or condensate thereof.

By surface-treating the basic filler with the above compound, a film in which the coupling material is condensed is formed on the surface of the basic filler. The surface treatment method is performed as follows, for example. The basic filler is finely pulverized or crushed to a desired average particle diameter, and then the (F1) surface treatment agent represented by the formula (1) and/or condensate thereof is mixed in the aqueous dispersion of the obtained basic filler. The mixture is hydrolyzed or partially hydrolyzed, and then condensed or dispersed in the system. In the above film forming method, hydrolysis and condensation of the coupling agent and film formation on the surface of the basic filler are simultaneously performed in the same system. However, it is possible to efficiently form a film on the surface of the basic filler by a film forming method in which hydrolysis and condensation of the coupling agent are performed in different system to prepare a low-condensate coupling agent, the low-condensate coupling agent is mixed with an aqueous dispersion of the basic filler obtained in the wet grinding step or the wet dispersion step. A film forming method in which a commercially available low-condensate coupling agent is used and mixed without a low-condensate formation process is more preferable. For the reason why this method is preferable, it is considered that when a monomeric coupling agent is used, because a large amount of water is present in the film forming step, condensation occurs three-dimensionally to proceed self-condensation predominantly and therefore the uniform film cannot be formed on the surface of the basic filler.

On the other hand, when a low-condensate coupling agent is used, it is considered that a film is uniformly formed on the surface of the basic filler in unit having a main chain of a certain length. The shape of this low-condensate coupling agent is not particularly limited, but linear shape is more prefer than three-dimensional shape. For the degree of polymerization, because the longer the length, the poorer the condensation reactivity and the poorer the formation of the coupling agent condensate film on the surface of the basic filler, preferable degree of polymerization is in the range of 2 to 100, that is, partial condensate of 2 to 100 molecules of the coupling agent is preferable. Specifically, the (F1) surface treatment agent represented by the formula (1) and/or condensate thereof is preferably a partial condensation of 2 to 100 molecules of tetraalkoxysilane or a polysiloxane in which all or part of the alkoxy groups of a partial condensate of 2 to 100 molecules of tetraalkoxysilane are substituted with OH groups. A partial condensate of 2 to 10 molecules is more preferable, and the molecular weight thereof is in the range of 500 to 1000. In addition, in the case of preparing a linear low-condensate coupling agent in another system, it is necessary to use a small amount of water so that the hydrolysis and condensation of the coupling agent can partially proceed. In this case, it is possible by using acid, alkali or other catalyst used in sol-gel process. As a result, the system is in a state in which the basic filler having an average particle diameter of 0.01 to 10 μm is finely dispersed without association in the aqueous medium in which the coupling agent condensate is dispersed.

The hydrolysis or partial hydrolysis of the coupling agent in the above aqueous dispersion is performed with stirring at a relatively low speed, the temperature is in the range from room temperature to 100° C., more preferably in the range from room temperature to 50° C., and the stirring time is usually in the range from several minutes to several ten hours, more preferably in the range from 30 minutes to 4 hours. No special method is required in such stirring, and facilities commonly used in general industries can be adopted and used. Examples include a stirring machine that can stir a slurry, such as a universal mixing and stirring machine or a planetary mixer and the like. Any stirring temperature can be adopted without problem as long as the temperature is a temperature equal to or lower than the boiling point of the aqueous medium. The stirring time must be regulated until gel formation, because the speed of gelation by condensation is affected by the type and amount of the coupling agent or low-condensed coupling agent to be added, the type, the particle diameter and the proportion in the aqueous dispersion of the inorganic fine particle, and the type of the aqueous medium and the proportion thereof in the aqueous dispersion. The stirring speed is required to be low because too high a stirring speed causes a gel structure to be broken and inhibits formation of a uniform film. The term "gel" as used herein means a creamy state or a jelly-like state swelling caused by growing condensation and absorbing an aqueous medium, and the term "gelation rate" refers to the speed at which these states appear. For the purpose of increasing the gelation rate, addition of a sol-gel catalyst such as an acid and an alkali, an organometal compound, a metal alkoxide, or a metal chelate compound is a preferred embodiment in terms of increasing the gelation rate. Examples of specific catalyst include an inorganic acid such as hydrochloric acid, acetic acid, nitric acid, formic acid, sulfuric acid and phosphoric acid, an organic acid such as paratoluenesulfonic acid, benzoic acid, phthalic acid and maleic acid, and a basic catalyst such as potassium hydroxide, sodium hydroxide and ammonia. Moreover, the acid or alkali used as a catalyst not only regulates the gelation rate, but also greatly contributes to charging the surface of the inorganic fine particles as a pH adjuster, thereby forming a uniform film. However, since the acid and base affect the material of the inorganic fine particle, it is necessary to select their use as appropriate. In addition, in the case of adding alcohol in this step, there is a significant effect of reducing the agglomeration of the inorganic fine particle in the drying step and further improving the pulverization property. The alcohol is preferably an alcohol whose carbon number is 2 to 10. In the case where an alcohol whose carbon number exceeds 10 is added, a long time is required to dry and remove the solvent due to high boiling point. Specific alcohols include ethyl alcohol, n-propyl alcohol, isopropyl alcohol, n-butyl alcohol, t-butyl alcohol, iso-butyl alcohol, n-pentyl alcohol, iso-amyl alcohol, n-hexyl alcohol, n-heptyl alcohol, n-octyl alcohol and n-dodecyl alcohol, and an alcohol having 2 to 4 carbon atoms, such as ethyl alcohol, n-propyl alcohol or iso-propyl alcohol is suitably used. The amount of the above alcohol to be added is 5 to 100 mass %, preferably 5 to 20 mass % based on water. This addition amount is the addition amount including the amount of alcohol contained in the wet pulverization process or the wet dispersion process. The addition amount exceeding 100 mass % causes problems such as complicating the drying step. The content of the basic filler is in the range from 25 to 100 mass %, preferably in the range from 30 to 75 mass % based on 100 mass % of the aqueous medium. When the content is more than 100 mass %, the gelation speed by condensation is high to hardly form a uniform film, and when the content is less than 25 mass %, the basic filler may be settled and/or phase separation in the aqueous dispersant may be caused during stirring. The amount of the coupling agent to be added depends on the particle diameter of the basic filler, and is in the range from 0.1 to 10 mass %, preferably 0.1 to 4 mass %, based on basic filler in terms of $SiO_2$. When the amount to be added is less than 0.1 mass %, no effect by formation of a film is exerted to make deagglomeration to primary particles impossible, resulting in agglomerates and when the amount is more than 10 mass %, a cured product after drying is too hard to be deagglomerated.

The system in a gel state is dried, and an aqueous medium is removed to solidify the gel. Drying consists of two steps of maturing and firing, wherein the former aims at growth of its gel structure and removal of the aqueous medium, and the latter aims at strengthening of gel structure. Since drying does not provide distortion to gel structure and removes the aqueous medium, its standing is necessary and drying is preferably performed by using an equipment of a box type hot air dryer and the like. The maturing temperature is in the range from room temperature to 100° C., and more preferably from 40 to 80° C. When the maturing temperature is less than this range, there is a risk that removal of the aqueous medium becomes insufficient, and when the maturing temperature exceeds this range conversely, there is a risk that an aqueous medium volatilizes rapidly and a defect occurs in the gel structure or a polysiloxane coating layer exfoliates from the basic filler surface. There is no problem as long as the maturing time is sufficient to remove the aqueous medium since maturing time depends on the capability of a drier and the like. On the one hand, the firing step is divided into two steps of temperature rising and temperature holding, the former temperature rising step is better to gradually rise the temperature to a target temperature for a long time and there is a possibility that a rapid temperature rising causes a strain in the gel structure since the heat conduction of a gel dispersion is poor. The latter holding stage is for firing at a constant temperature. The firing time is within a range of 1 hour to 100 hours, preferably 2 hours to 75 hours, more preferably 5 hours to 50 hours. The longer this time is, the more effective it is. However, the effect is not recognized after a certain period of time. The firing temperature is within a range of 100 to 500° C., preferably 100 to 450° C., more preferably 130 to 400° C. This temperature must be selected appropriately so as not to affect the raw material of the basic filler and to the extent that the porous gel structure is not made non-porous. The aqueous medium is removed from the gel by drying as described above to obtain a constricted solidified material. Although the solidified material is in a state of an aggregate of the basic filler, it is not merely an aggregate of the basic filler, and a coating formed by condensation intervenes between the boundary surfaces of each fine particle. Therefore, when this solidified material is deagglomerated into a material corresponding to the basic filler before forming the coating as the next process, a surface coated inorganic fine particle, that is, the inorganic filler of the present disclosure is obtained. The "deagglomerated into a material corresponding to the basic filler before forming the coating" herein means to deagglomerating into a basic filler, and a different point from the original inorganic filler is that each inorganic fine particle is coated with a coupling agent condensate. In addition, as long as there is no problem, a secondary aggregate may be included. Deagglomerating of the solidified material is easily possible by applying shearing force or an impact force. The deagglomerating method may be performed, for example, by using a Henschel mixer, a crossing rotary mixer, a super mixer and the like.

It is preferable that after a surface treatment with the (F1) surface treatment agent represented by the formula (1) and/or condensate thereof, the basic filler is surface-treated with a silane coupling agent having a polymerizable group and/or an acidic polymer. By surface-treating with a silane coupling agent having a polymerizable group, it is possible to copolymerize with a polymerizable monomer, therefore improvement in mechanical strength can be expected. Further, by surface-treating with an acidic polymer, the amount of ion release is increased, therefore the acid neutralizing ability is improved.

The effect of improving the affinity to the polymerizable monomer, the dispersibality to the polymerizable monomer and the mechanical strength and water resistance of the cured product is exhibited by treating the (E1) surface-treated basic filler with a silane coupling agent having a polymerizable group. A silane coupling agent having a polymerizable group forms a silanol bond with a silanol group on the surface of the filler. However, because the basic filler of the present disclosure is surface treated with the (F1) surface treatment agent represented by the formula (1) and/or condensate thereof, the coupling agent condensate film is formed on the surface of the filler. In particular, when the (F1) surface treatment agent represented by the formula (1) and/or condensate thereof is a silane coupling agent, a large number of silanol groups which are reaction sites of the silane coupling agent having a polymerizable group are introduced. Therefore, since it is possible to react more silane coupling agent having a polymerizable group with the surface of the filler, the wettability of the basic filler to the polymerizable monomer is improved, it becomes possible to compounding more (E1) surface-treated basic filler in the dental curable composition, the mechanical strength of the dental curable composition is improved.

The surface treatment method for the silane coupling agent having a polymerizable group is not particularly limited, and known methods can be adopted without limitation. The treatment amount of the surface treatment agent in the basic filler is preferably 0.01 to 30 mass by weight, more preferably 0.5 to 20 mass by weight based on 100 mass by weight of the filler before treatment from the viewpoint of not reducing the basicity.

When the basic filler contains an acid-reactive element, it is possible to cause a cement reaction the acid-reactive element contained in the basic filler with the acidic polymer to form a cement reaction phase on the surface of the basic filler by surface treating with an acidic polymer. Although a coating layer of the coupling agent condensate exists on the surface of the basic filler, since this coupling agent condensate coating layer has a porous gel structure, the acidic polymer permeates the coupling agent condensate coating and reaches the surface of the basic filler while diffusing. The acidic polymer that reaches the filler surface causes an acid-base reaction to form a cement layer. It is expected by this cement layer to increase the amount of ion released from the basic filler, improve the acid neutralization ability associated with it, and incorporation of ion in the case that the amount of ion around the basic filler is large.

More preferable examples of the acid-reactive element include a metal element belonging to Group I, Group II, and Group III of the Periodic Table, and particularly preferable examples include sodium, potassium, calcium, strontium, lanthanum, aluminum and the like. Specific examples of these basic fillers include aluminum silicate, aluminum oxide, various glasses (including a glass by melting method, a glass produced by a vapor phase reaction, synthetic glass by sol-gel method and the like), strontium fluoride, calcium carbonate, kaolin, mica, aluminum sulfate, calcium sulfate, barium sulfate, calcium phosphate, calcium hydroxide, strontium hydroxide, zeolite, hydroxyapatite, and aluminum nitride. Glasses are particularly preferable. Glasses are preferable because hardness is lower than silica compounds, light transmission is excellent, it is possible to contain an element that blocks X-ray and fluorine and therefore it is possible to impart the function required for a dental composition. Most preferable examples include alumina silicate glass, borosilicate, alumina borate and boroalumina silicate glass which contain heavy metal such as strontium, barium and lanthanum and fluorine.

When the acid-base reaction is too fast, the formation of the cement phase is non-uniform. Therefore, among the acidic polymers that can be used for surface treatment, a homopolymer and copolymer of an $\alpha,\beta$-unsaturated carboxylic acid are preferable because acid-base reaction of with acid-reactive element relatively slowly progresses. An acrylic acid polymer, an acrylic acid-maleic acid copolymer and an acrylic acid-itaconic acid copolymer are more preferable.

When the basic filler of the present disclosure contains fluorine, the dental curable composition can impart fluorine sustained release property. As the basic filler containing fluorine, for example, sodium fluoride, strontium fluoride, lanthanum fluoride, ytterbium fluoride, yttrium fluoride, and calcium-containing fluoroalumina silicate are used. Further, in order for the inorganic filler of the present disclosure to have radiopaque property, the core basic filler must contain a heavy metal. In this case, the basic filler may be, for example, strontium fluoride, lanthanum fluoride, ytterbium fluoride, yttrium fluoride, lanthanum-containing fluoroalumina silicate, and strontium-containing fluoroalumina silicate are used.

The acidic polymer used for the surface treatment of the basic filler may include a polymerizable monomer not having an acidic group within a range that does not interfere with the formation of the cement reaction phase with the basic filler, in addition to the polymerizable monomer having an acidic group.

The method for reacting the basic filler with the acidic polymer can be conducted by use of any equipment commonly used in the art as long as the equipment is a dry fluid type stirring machine, and examples include a Henschel mixer, a super mixer and a high-speed mixer. The reaction of the acidic polymer with the basic filler containing the acid-reactive element coated with the coupling agent condensate can be made by simply contacting the basic filler with the acidic polymer solution, such as by impregnation. As an example, a basic filler coated with a condensate of a coupling agent is caused to dry flow and in the flow state, the acid polymer solution is dispersed from above and sufficiently stirred. The method of dispersing the acidic polymer solution here is not particularly limited, and a dropping or spraying system that can allow for uniform dispersing is more preferable. The reaction is preferably conducted around room temperature, and a higher temperature makes a reaction of an acid-reactive element and the acidic polymer faster, resulting in ununiformed formation of a cement phase.

It is preferable to remove the water content in the cement reaction phase by performing a heat treatment after the reaction. If water content remains in the cement reaction phase, it is disadvantageous in terms of strength, but since the basic filler of the present disclosure is covered and strengthened by the coupling agent condensate film, the decrease in mechanical strength is suppressed. The heat treatment method after the acid polymer treatment is not particularly limited, and can be performed by a known general method. As the equipment used for the heat treatment, a box-type hot air dryer or the like, a rotary heat treatment device capable of uniform heating and the like are preferable. The heat treatment temperature is in the range of room temperature to 200° C., more preferably in the range of 40 to 150° C. When the temperature is lower than this range, the removal of the aqueous medium is insufficient, and when the temperature is higher than this range, there is a risk that the organic layer of the acidic polymer is decomposed or discolored. Since the heat treatment period depends on the capacity of the dryer and the like, there is no problem as long as the aqueous medium can be sufficiently removed. After the heat treatment, the heat-treated product can be easily crushed by applying a shearing force or an impact force, and the crushing method can be performed by the equipment used for the above reaction.

A solvent employed for preparing the acid polymer solution used in the reaction may be solvent for dissolving the acid polymer. Examples of the solvent include water, ethanol, and acetone. Of these, water is particularly preferable. When water is used, an acid group of the acid polymer dissociates and reacts uniformly with the surface of the basic filler as the core. On the other hand, in the case of other solvent, the reaction with the surface of the basic filler as the core is insufficient, and there are residual unreacted acidic groups. Therefore, when this basic filler is compounded into the dental curable composition, it causes deterioration of the material due to inhibition of polymerization of the polymerizable monomer and water absorption of the cured product.

The weight average molecular weight of the polymer dissolved in the acidic polymer solution is preferably in the range of 2000 to 50000, and more preferably in the range of 5000 to 40000. When the acidic polymer has the weight average molecular weight less than 2000, there is a case that the strength of the cement reaction phase is easily lowered to reduce material strength. When the acidic polymer has the weight average molecular weight more than 50000, there is a tendency that the viscosity of the acidic polymer solution increase, the coupling agent condensate coating (porous) is difficult to diffuse, a residual unreacted acidic group remains and an adverse effect is exhibited. The acid polymer concentration in 100 parts by mass of the acid polymer solution is preferably in the range of 3 to 25 parts by mass, and more preferably in the range of 8 to 20 parts by mass. When the concentration of the acidic polymer is less than 3 parts by mass, the strength of the cement phase described above is weakened, and the fluidity of the surface-treated basic filler is deteriorated due to the influence of water, and a uniform cement reaction phase is not formed. When the concentration of the acidic polymer is more than 25 parts by mass, there is a problem that the coupling agent condensate coating (porous) is difficult to diffuse, the acid-base reaction by contacting with the basic filler as the core is rapid, therefore curing initiates during the reaction to cause aggregation. The amount of the acidic polymer solution to be added to the surface treated basic filler is preferably in the range from 6 to 40 parts by mass, more preferably 10 to 30 parts by mass. Converting this addition amount, an optimal amount of the acid polymer with respect to the coupling agent condensate coated basic filler is in the range of 1 to 7 parts by mass, and an optimal amount of water is in the range of 10 to 25 parts by mass.

This reaction is affected by the surface area of the basic filler as the core. The smaller the surface area, the slower the acid-base reaction, and the larger the surface area, the faster the reaction. In other words, the particle size distribution is important, and there is a possibility in the case of a basic filler having a monodisperse particle size distribution that a cement reaction phase is formed at the same time, and rather, it is considered that the sequential reaction occurs in the case that the molecular weight distribution of the acidic polymer is more polydispersity, and the cement reaction phase can be formed more efficiently and uniformly. In addition, because the outermost coupling agent condensate film exists, a period of time required for arriving of an acidic polymer at the surface of the coupling agent condensate film to diffuse through the porous and arrive the surface of the basic filler as the core is controlled, it is possible to form a uniform cement reaction phase. When the coupling agent condensate film is not present, a reaction initiates as soon as the acidic polymer contacts with the surface of the basic filler to cause bridging between particles, but this is also prevented.

The compounding amount of the (E1) surface-treated basic filler in the paste, with respect to 100 parts by mass of the (A) polymerizable monomer, is preferably 10 to 400 parts by mass, more preferably 50 to 400 parts by mass, still more preferably 100 to 400 parts by mass. When the compounding amount of the basic filler is less than 10 parts by mass, there is a case that the improvement in storage stability is not exhibited, and when the compounding amount is more than 400 parts by mass, there is a case that the paste property of the composition is hard and it is difficult to handle. However, for example, when the filler is surface-treated with a large amount of a surface treatment agent, good paste property is obtained even when the compounding amount is 400 parts by mass or more.

As the basic filler, a basic filler satisfying the above definition may be used alone, or two or more kinds of basic fillers may be used in combination. Moreover, a non-basic filler may be compounded in the dental curable composition of the present disclosure.

In the present disclosure, the non-basic filler refers to the case that a dispersion has pH-value of less than 7.5 according to the above definition of a preferable basic filler, and the non-basic filler is an inorganic filler, an organic filler, an organic-inorganic composite fillers, etc., but they can be used not only alone but also in combination of two or more regardless of the type of filler. Examples thereof include silica-based inorganic compounds such as silica and silica-zirconia, and trifluoroytterbium.

The non-basic filler can be treated with a surface treatment agent represented by a silane coupling material in order to improve the affinity to the polymerizable monomer, the dispersability in the polymerizable monomer, and the mechanical strength and water resistance of the cured product in the same manner as the basic filler.

The shape of the non-basic filler is not particularly limited, and amorphous and spherical fillers can be used. The average particle diameter of the non-basic filler is preferably within a range from 0.01 μm to 50 μm.

The dental curable composition of the present disclosure may not substantially comprise water. When water is included, there is a case that deterioration of storage stability and strength occur. "Substantially comprise water" means that water is intentionally compounded to the dental curable composition, excluding cases that water is contained as impurities or by-products in the raw material, or that water is unintentionally contained during preparing process. The dental curable composition of the present disclosure can contain water for the purpose of dissolving raw material, but even in such a case, it is not preferable to contain water in the dental curable composition. On the other hand, when water can be removed from the final composition by heating, pressure reduction or the like during the preparing process, it can be expected that the strength of the dental curable composition is not be affected. In the present disclosure, "not substantially comprise water" means that the amount of water contained in 100 parts by mass of the dental curable composition is less than 1 part by mass, preferably less than 0.1 part by mass.

Other Component

Further, the dental curable composition of the present disclosure may contain a component other than above described (A) to (E) components within a range not to impair the effect of the present disclosure. For example, an excipient typified by fumed silica, benzophenone-based and benzotriazole-based ultraviolet absorbers, polymerization inhibitors such as hydroquinone, hydroquinone monomethyl ether and 2,5-ditershally butyl-4-methylphenol, chain transfer materials such as α-alkylstyrene compound, mercaptan compound such as n-butyl mercaptan and n-octyl mercaptan, and terpenoid compound such as limonene, myrsen, α-terpinene, 8-terpinene, y-terpinene, terpinoren, 8-pinene and α-pinene, metal supplementary material such as aminocarboxylic acid chelating agent and phosphonic acid chelating agent, discoloration inhibitors, antibacterial materials, coloring pigments, water and solvent that can be mixed with water in any ratio, and other additives conventionally known in the art may be added as necessary and as desired.

A preparing method of the dental curable composition of the present disclosure is not particularly limited. Examples of a general preparing method of a dental composition include a method which comprises preparing a matrix by mixing (A) polymerizable monomer, and (BC) polymerization initiator in advance, kneading the matrix and (E) filler, and removing air bubbles under vacuum to prepare a uniform paste. In the present disclosure, it can be prepared by the above-described method without any problem.

The dental curable composition of the present disclosure is applied as a dental adhesive material, a dental composite resin, a dental core build-up material, a dental resin cement, a dental coating material, a dental sealant material, a dental manicure material, a dental splinting material, a dental hard resin, a dental CAD-CAM restoration material, a dental 3D printer material and the like.

One Pack Type Dental Composition

When the dental curable composition of the present disclosure is used for one pack type photocurable composition, particularly as dental materials, it is preferable to use for a dental adhesive material, a dental composite resin, a dental core build-up material, a dental resin cement, a dental coating material, a dental sealant material, a dental manicure material, a dental splinting material, a dental CAD-CAM restoration material and a dental 3D printer material, it is particularly preferable to use for a dental adhesive material, a dental composite resin, a dental core build-up material, a dental resin cement, a dental coating material, a dental sealant material, a dental manicure material and a dental splinting material. In the case of a one pack type dental curable composition, it can be expected that there are few technical errors and the risk of contamination with air bubbles is reduced.

Two Packs Type Dental Composition

When the dental curable composition of the present disclosure is used for two packs type a dental composition, particularly as dental materials, it is preferable to use for a dental adhesive material, a dental composite resin, a dental core build-up material, a dental resin cement, a dental coating material, a dental sealant material, a dental manicure material, a dental splinting material, a dental CAD-CAM restoration material and a dental 3D printer material, it is particularly preferable to use for a dental composite resin, a dental core build-up material and a dental resin cement. The two packs type dental curable composition is used by kneading the two packs including a first paste and a second paste immediately before use. The kneading is performed by mixing the first paste and the second paste in a volume ratio of 0.8 to 1.2:1.0 or a mass ratio of 0.8 to 1.2:1.0, preferably an equal volume ratio. The kneading method may be a known method such as manual kneading using a spatula, or automatic kneading via a dedicated shaking device or a static mixer. Since the components can be separated into two packs, compounds that cannot be compounded in the same paste can be compounded separately, therefore the storage stability is excellent.

EXAMPLES

Hereinafter, examples of the present disclosure are specifically described. However, the present disclosure is not intended to be limited to these Examples.

The materials used in Examples and Comparative examples and their abbreviations are listed below.

(A) Polymerizable Monomer

Polymerizable Monomer not Corresponding to the (A1) Polymerizable Monomer Having an Acidic Group Bis-GMA: 2,2-bis [4-(3-methacryloyloxy-2-hydroxy-propoxy) phenyl] propane
2.6E: 2,2-bis (4-(meth) acryloyloxy polyethoxyphenyl) propane in which the average addition mole number of ethoxy groups is 2.6
UDMA: N,N-(2,2,4-trimethyl hexamethylene) bis [2-(aminocarboxy) ethanol]methacrylate
TEGDMA: triethyleneglycol dimethacrylate
GDMA: glycerin dimethacrylate
HEMA: 2-hydroxyethyl methacrylate
NPG: neopentyl glycol dimethacrylate
MOTMS: 8-methacryloxyoctyl trimethoxysilane
MPTMS: 3-methacryloxypropyl trimethoxysilane
MDDT: 10-methacryloxydecyl-6,8-ditioctanate (A1) Polymerizable Monomer Having an Acidic Group MDP: 10-methacryloyloxydecyl dihydrogen phosphate
MHPA: 6-methacryloxyhexyl phosphonoacetate
MET: 4-methacryloyloxyethyl trimellitate
META: 4-methacryloyloxyethyl trimellitate anhydride
AET: 4-acryloyloxyethyl trimellitate (B) Photo Polymerization Initiator (B1) Photosensitizer CQ: camphorquinone
MAPO: diphenyl (2,4,6-trimethylbenzoyl) phosphine oxide
BAPO: phenyl bis (2,4,6-trimethylbenzoyl) phosphine oxide (B2) Photoacid Generator Salt of an Anion Having an Organic Group in which at Least One H is Substituted with F and One or More Atoms of P, B, Al, S, and Ga, and an Aryl Iodonium Cation B2-1: bis (4-tert-butylphenyl) iodonium nonafluorobutane sulfonate

[Chemical formula 3]

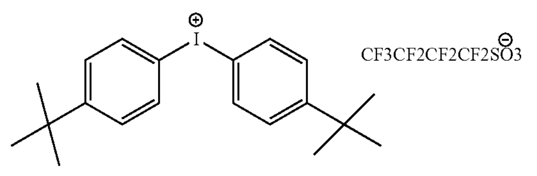

B2-2: bis (4-tert-butylphenyl) iodonium tris (pentafluoropropyl) trifluorophosphate

[Chemical formula 4]

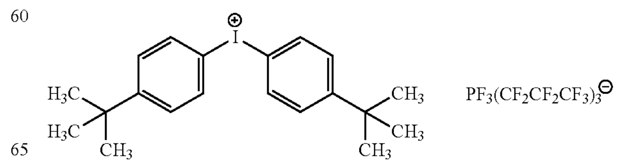

B2-3: p-cumenyl (p-tolyl) iodonium tris (pentafluoroethyl) trifluorophosphate

[Chemical formula 5]

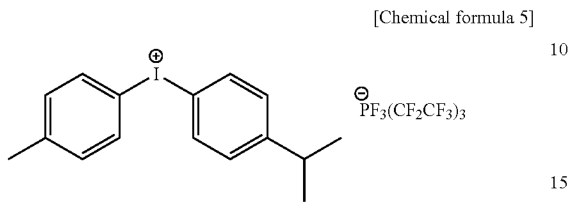

B2-4: bis (4-n-dodecylphenyl) iodonium tetrakis (pentafluorophenyl) borate

[Chemical formula 6]

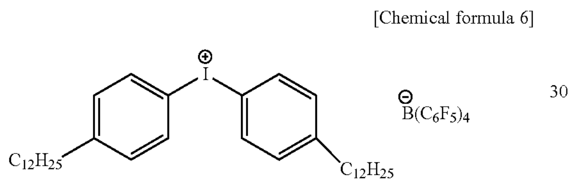

B2-5: bis [(4-tert-butyl) phenyl] iodonium tetra (nonafluoro-tert-butoxy) aluminate

[Chemical formula 7]

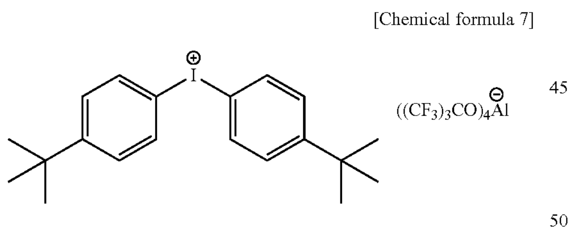

B2-6: bis [4-isopropyl phenyl] iodonium tetra (pentafluorophenyl) gallate

[Chemical formula 8]

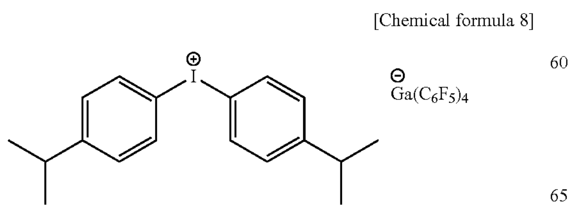

B2-7: 4-cumenyl (4-tolyl) iodonium tetrakis (pentafluorophenyl) borate

[Chemical formula 9]

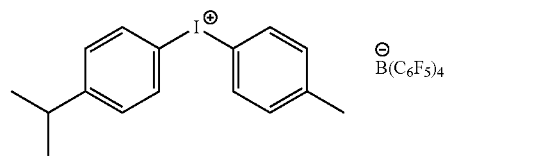

Salt of an Anion Having an Organic Group and One or More Atoms of P, B, Al, S, and Ga, and an Aryl Iodonium Cation B2-11: bis (4-tert-butylphenyl) iodonium-p-toluenesulfonate

[Chemical formula 10]

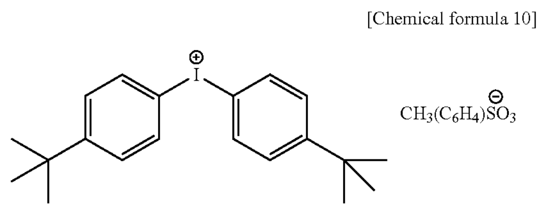 [SMILES: CC(C)(C)c1ccc([I+]c2ccc(C(C)(C)C)cc2)cc1 ; "CH3(C6H4)SO3"]

Photoacid Generator Other than Salt of an Anion Having an Organic Group and One or More Atoms of P, B, Al, S, and Ga, and an Aryl Iodonium Cation B2-12: bis (4-tert-butylphenyl) iodonium hexafluorophosphate

[Chemical formula 11]

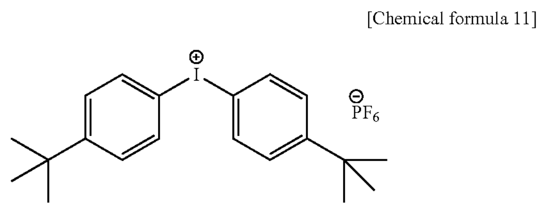

B2-13: 2,4,6-tris (trichloromethyl)-1,3,5-triazine

[Chemical formula 12]

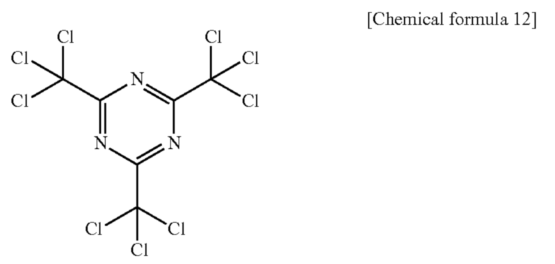 [SMILES: ClC(Cl)(Cl)c1nc(C(Cl)(Cl)Cl)nc(C(Cl)(Cl)Cl)n1]

B2-14: diphenyliodonium-2-carboxylate monohydrate

[Chemical formula 13]

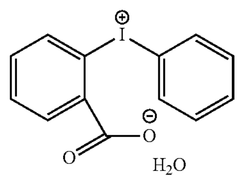

(C) Chemical Polymerization Initiator (C1) Organic Peroxide

CHP: cumene hydroperoxide
TMBH: 1,1,3,3-tetramethylbutyl hydroperoxide
TPE: 1,1,3,3-tetramethylbutyl peroxy-2-ethylhexanoate
BPO: benzoyl peroxide (D) Polymerization Accelerator Aliphatic Tertiary Amine Compound MDEOA: methyl diethanolamine
TEA: triethanolamine
TIPA: triisopropanolamine
DMAEMA: N,N-dimethylamino ethylmethacrylate
DIAEMA: N,N-diisopropylaminoethyl methacrylate
TBA: tribenzylamine
DBGE: N,N-dibenzyl glycine ethyl
DBAE: N,N-dibenzylamino ethanol
DBMA: dibenzylmethylamine Aromatic Tertiary Amine Compound DMBE: N,N-dimethylaminobenzoate ethyl
DEPT: N,N-di(2-hydroxyethyl)-p-toluidine
DHPT: N,N-di(2-hydroxypropyl)-p-toluidine Organic Metal Compound SnL: dioctyl-tin-dilaurate
CAA: acetylacetone copper
VOA: vanadyl acetylacetonate Other Polymerization Accelerator BTU: N-benzoyl thiourea
PTU: (2-pyridyl) thiourea
PTSA: sodium p-toluene sulfinate
TMBA: trimethyl barbituric acid
KPS: potassium peroxodisulfate UV Absorber BT: 2-(2-hydroxy-5-methylphenyl) benzotriazole Polymerization Inhibitor BHT: 2,6-di-t-butyl-4-methylphenol
MeHQ: p-methoxyphenol Fluorescent Agent FA: 2,5-dihydroxyterephthalate diethyl (E) Filler The preparing method of each filler used for preparing the dental curable composition is shown below.

Raw material glasses (G1 to G7) shown in Table 1 were used for the preparation of fillers. For pH-value of raw material glass, a dispersion of 1.0 g of the filler in a mixed solution of 40 g of distilled water 40 g and 10 g of ethanol after stirring for 1 hour was measured.

TABLE 1

| | | G1 | G2 | G3 | G4 | G5 | G6 | G7 |
|---|---|---|---|---|---|---|---|---|
| Composition (w/w %) | SiO2 | 32.2 | 27.3 | 23.7 | 24.2 | 50.0 | 60.6 | 23.8 |
| | Al2O3 | 19.3 | 24.2 | 19.4 | 22.6 | 23.2 | 10.9 | 11.1 |
| | SrO | 26.9 | 32.8 | 40.3 | 30.6 | 5.4 | 7.2 | 24.2 |
| | P2O5 | | 5.0 | 2.8 | | 9.5 | 5.8 | 2.0 |
| | F | 8.7 | 7.5 | 6.2 | 8.9 | 10.9 | 10.1 | 0.5 |
| | Na2O | 4.0 | 0.3 | | 2.6 | 1.0 | 5.1 | |
| | B2O3 | 8.9 | 2.9 | 1.8 | 11.1 | | | |
| | CaO | | | 5.8 | | | | 37.5 |
| | Others | | | | | | 0.3 | 0.9 |
| | Total | 100.0 | 100.0 | 100.0 | 100.0 | 100.0 | 100.0 | 100.0 |
| Average particle diameter | μm | 2.8 | 0.8 | 0.4 | 10 | 3.3 | 1.1 | 4.9 |
| pH | | 7.7 | 8.9 | 8.7 | 8 | 7.3 | 6.6 | 10.8 |
| Class | | | Basic | | | Non-Basic | | High Basic |

Preparation of Filler E1

Polysiloxane Treatment

Firstly, 1.5 g of a low condensate of silane compound "MKC SILICATE MS56S" ($SiO_2$ content: 56.0% by mass, degree of polymerization: 2 to 100, manufactured by Mitsubishi Chemical Corporation) was added to 100.0 g of the raw material glass G1, and stirred-mixed for 90 minutes. After mixing for a predetermined time, the resulting treated slurry was aged in a hot air dryer at 50° C. for 40 hours, then heated to 150° C. and held for 6 hours, then cooled to obtain a heat treated product. The obtained heat-treated product was placed in a Henschel mixer and pulverized at 1800 rpm for 5 minutes. After pulverization, a polysiloxane-treated product having good fluidity was obtained.

Silane Treatment

A silane coupling treatment solution prepared by stirring 100.0 g of water, 80.0 g of ethanol, 0.003 g of phosphoric acid, and 5.0 g of 3-methacryloyloxypropyl trimethoxysilane as a silane coupling agent at room temperature for 2 hours was added to 100.0 g of the polysiloxane treated product and stirred for 30 minutes. Thereafter, a heat treatment was performed at 100° C. for 15 hours to obtain filler E1.

Preparation of Filler E2

Silane Treatment

A silane coupling treatment solution prepared by stirring 100.0 g of water, 80.0 g of ethanol, 0.003 g of phosphoric acid, and 9.0 g of 3-methacryloyloxypropyl trimethoxysilane as a silane coupling agent at room temperature for 2 hours was added to 100.0 g of filler E5 described below and stirred for 30 minutes. Thereafter, a heat treatment was performed at 100° C. for 15 hours to obtain filler E2.

Preparation of Filler E3

Acidic Polymer Treatment

Firstly, 100.0 g of filler E5 described below was put into a Henschel mixer, and 12.0 g of a polyacrylic acid aqueous solution (polymer concentration: 13% by mass, weight average molecular weight: 20,000, manufactured by Nacalai Co., Ltd.) was sprayed from above while stirring. After spraying, the powder taken out from the mixer was heated in a hot air dryer at 100° C. for 3 hours to obtain a polysiloxane-polyacrylic acid-treated product.

Silane Treatment

A silane coupling treatment solution prepared by stirring 100.0 g of water, 80.0 g of ethanol, 0.003 g of phosphoric acid, and 9.0 g of 3-methacryloyloxypropyl trimethoxysilane as a silane coupling agent at room temperature for 2 hours was added to 100.0 g of the polysiloxane-polyacrylic acid-treated product and stirred for 30 minutes. Thereafter, a heat treatment was performed at 100° C. for 15 hours to obtain filler E3.

Preparation of Filler E4

Acidic Polymer Treatment

After obtaining a polysiloxane-treated product by the same procedure as for the filler E1, 100 g of the polysiloxane-treated product was put into a Henschel mixer, and 23.0 g of a polyacrylic acid aqueous solution (polymer concentration: 13% by mass, weight average molecular weight: 20,000, manufactured by Nacalai Co., Ltd.) was sprayed from above while stirring. After spraying, the powder taken out from the mixer was heated in a hot air dryer at 100° C. for 3 hours to obtain file E4 which is a polysiloxane-polyacrylic acid-treated product.

Preparation of Filler E5

Polysiloxane Treatment

Firstly, 3.5 g of a low condensate of silane compound "MKC SILICATE MS56S" ($SiO_2$ content: 56.0% by mass, degree of polymerization: 2 to 100, manufactured by Mitsubishi Chemical Corporation) was added to 100.0 g of the raw material glass G2, and stirred-mixed for 90 minutes. After mixing for a predetermined time, the resulting treated slurry was aged in a hot air dryer at 50° C. for 40 hours, then heated to 150° C. and held for 6 hours, then cooled to obtain a heat treated product. The obtained heat-treated product was placed in a Henschel mixer and pulverized at 1800 rpm for 5 minutes. After pulverization, filler E5 which was a polysiloxane-treated product having good fluidity was obtained.

Preparation of Filler E6

Polysiloxane Treatment

Firstly, 4.5 g of a low condensate of silane compound "MKC SILICATE MS56S" ($SiO_2$ content: 56.0% by mass, degree of polymerization: 2 to 100, manufactured by Mitsubishi Chemical Corporation) was added to 100.0 g of the raw material glass G3, and stirred-mixed for 90 minutes. After mixing for a predetermined time, the resulting treated slurry was aged in a hot air dryer at 50° C. for 40 hours, then heated to 150° C. and held for 6 hours, then cooled to obtain a heat treated product. The obtained heat-treated product was placed in a Henschel mixer and pulverized at 1800 rpm for 5 minutes. After pulverization, a polysiloxane-treated product having good fluidity was obtained.

Acidic Polymer Treatment

Then, 100.0 g of the polysiloxane-treated product was put into a Henschel mixer, and 16.0 g of a polyacrylic acid aqueous solution (polymer concentration: 13% by mass, weight average molecular weight: 20,000, manufactured by Nacalai Co., Ltd.) was sprayed from above while stirring. After spraying, the powder taken out from the mixer was heated in a hot air dryer at 100° C. for 3 hours to obtain a polysiloxane-polyacrylic acid-treated product.

Silane Treatment

A silane coupling treatment solution prepared by stirring 100.0 g of water, 80.0 g of ethanol, 0.003 g of phosphoric acid, and 12.0 g of 3-methacryloyloxypropyl trimethoxysilane as a silane coupling agent at room temperature for 2 hours was added to 100.0 g of the polysiloxane-polyacrylic acid-treated product and stirred for 30 minutes. Thereafter, a heat treatment was performed at 100° C. for 15 hours to obtain filler E6.

Preparation of Filler E7

Polysiloxane Treatment

Firstly, 1.0 g of a low condensate of silane compound "MKC SILICATE MS56S" (SiO2 content: 56.0% by mass, degree of polymerization: 2 to 100, manufactured by Mitsubishi Chemical Corporation) was added to 100.0 g of the raw material glass G7, and stirred-mixed for 90 minutes. After mixing for a predetermined time, the resulting treated slurry was aged in a hot air dryer at 50° C. for 40 hours, then heated to 150° C. and held for 6 hours, then cooled to obtain a heat treated product. The obtained heat-treated product was placed in a Henschel mixer and crushed at 1800 rpm for 5 minutes. After pulverization, a polysiloxane-treated product having good fluidity was obtained.

Silane Treatment

A silane coupling treatment solution prepared by stirring 100.0 g of water, 80.0 g of ethanol, 0.003 g of phosphoric acid, and 3.0 g of 3-methacryloyloxypropyl trimethoxysilane as a silane coupling agent at room temperature for 2 hours was added to 100.0 g of the polysiloxane treated product and stirred for 30 minutes. Thereafter, a heat treatment was performed at 100° C. for 15 hours to obtain filler E7.

Preparation of Filler E8

Filler E8 was by prepared under the same conditions as for filler E2 other than the heat treatment conditions in the polysiloxane treatment were changed to conditions in which aging is in a hot air dryer at 50° C. for 40 hours, heating is to 450° C. and holding is 6 hours.

Preparation of Filler E9

Polysiloxane Treatment

Firstly, 0.5 g of a low condensate of silane compound "MKC SILICATE MS56S" ($SiO2$ content: 56.0% by mass, degree of polymerization: 2 to 100, manufactured by Mitsubishi Chemical Corporation) was added to 100.0 g of the raw material glass G4, and stirred-mixed for 90 minutes. After mixing for a predetermined time, the resulting treated slurry was aged in a hot air dryer at 50° C. for 40 hours, then heated to 150° C. and held for 6 hours, then cooled to obtain a heat treated product. The obtained heat-treated product was placed in a Henschel mixer and crushed at 1800 rpm for 5 minutes. After pulverization, a polysiloxane-treated product having good fluidity was obtained.

Silane Treatment

A silane coupling treatment solution prepared by stirring 100.0 g of water, 80.0 g of ethanol, 0.003 g of phosphoric acid, and 1.5 g of 3-methacryloyloxypropyl trimethoxysilane as a silane coupling agent at room temperature for 2 hours was added to 100.0 g of the polysiloxane treated product and stirred for 30 minutes. Thereafter, a heat treatment was performed at 100° C. for 15 hours to obtain filler E9.

Preparation of Filler E11

Filler E11 was prepared under the same conditions as for filler E1 other than the silane coupling agent used in the silane treatment was changed to 7.0 g of 8-methacryloyloxyoctyl trimethoxysilane.

Preparation of Filler E12

Silane Treatment

After obtaining a polysiloxane-treated material by the same procedure as for the filler E6, a silane coupling treatment solution prepared by stirring 100.0 g of water, 80.0 g of ethanol, 0.003 g of phosphoric acid, and 15.0 g of 8-methacryloyloxy octyltrimethoxysilane as a silane coupling agent at room temperature for 2 hours was added to 100.0 g of the above polysiloxane-treated product and stirred for 30 minutes. Thereafter, a heat treatment was performed at 100° C. for 15 hours to obtain filler E12.

Preparation of Filler E13

Filler E13 was prepared under the same conditions as for filler E2 other than the silane coupling agent used in the silane treatment was changed to 12.0 g of SC1.

SC1: 4,4-diethoxy-17-oxo-3,16-dioxa-18-aza-4-silaicosan-20-yl methacrylate

[Chemical formula 14]

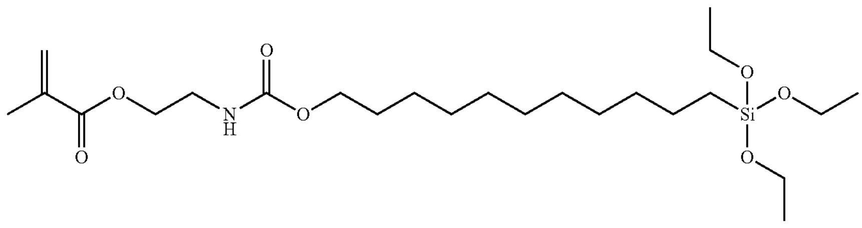

Preparation of Filler E10

Filler E10 was prepared under the same conditions as for filler E1 other than the heat treatment conditions in the polysiloxane treatment were changed to conditions in which aging is in a hot air dryer at 50° C. for 40 hours, heating is to 400° C. and holding is 6 hours.

Preparation of Filler E14

Filler E14 was prepared under the same conditions as for filler E2 other than the silane coupling agent used in the silane treatment was changed to 12.0 g of SC2.

SC2: 4,4-diethoxy-17-oxo-3,16,21-trioxa-18-aza-4-silatricosan-23-yl methacrylate

[Chemical formula 15]

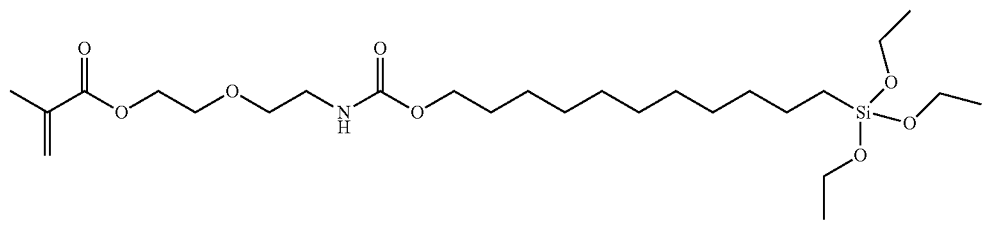

Preparation of Filler E15

Filler E15 was prepared under the same conditions as for filler E6 other than the silane coupling agent used in the silane treatment was changed to 15.0 g of 8-methacryloyloxyoctyl trimethoxysilane.

Preparation of Filler E16

Filler E16 was prepared under the same conditions as for filler E2 other than the heat treatment conditions in the polysiloxane treatment were changed to conditions in which aging is in a hot air dryer at 50° C. for 40 hours, heating is to 100° C. and holding is 6 hours.

Preparation of Filler EC1

Filler EC1 was prepared under the same conditions as for filler E1 other than the raw glass was changed from G1 to G5.

Preparation of Filler EC2

Silane Treatment

A silane coupling treatment solution prepared by stirring 100.0 g of water, 80.0 g of ethanol, 0.003 g of phosphoric acid, and 5.0 g of 3-methacryloyloxypropyl trimethoxysilane as a silane coupling agent at room temperature for 2 hours was added to 100.0 g of the raw material glass G5 and stirred for 30 minutes. Thereafter, a heat treatment was performed at 100° C. for 15 hours to obtain filler EC2.

Preparation of Filler EC3

Silane Treatment

A silane coupling treatment solution prepared by stirring 100.0 g of water, 80.0 g of ethanol, 0.003 g of phosphoric acid, and 8.0 g of 3-methacryloyloxypropyl trimethoxysilane as a silane coupling agent at room temperature for 2 hours was added to 100.0 g of filler EC9 described below and stirred for 30 minutes. Thereafter, a heat treatment was performed at 100° C. for 15 hours to obtain filler EC3.

Preparation of Filler EC4

Raw material glass G1 not treated at all was used as filler EC4.

Preparation of Filler EC5

Raw material glass G2 not treated at all was used as filler EC5.

Preparation of Filler EC6

Polysiloxane Treatment

Firstly, 3.0 g of a low condensate of silane compound "MKC SILICATE MS56S" ($SiO2$ content: 56.0% by mass, degree of polymerization: 2 to 100, manufactured by Mitsubishi Chemical Corporation) was added to 100.0 g of the raw material glass G6, and stirred-mixed for 90 minutes. After mixing for a predetermined time, the resulting treated slurry was aged in a hot air dryer at 50° C. for 40 hours, then heated to 150° C. and held for 6 hours, then cooled to obtain a heat treated product. The obtained heat-treated product was placed in a Henschel mixer and crushed at 1800 rpm for 5 minutes. After pulverization, a polysiloxane-treated product having good fluidity was obtained.

Acidic Polymer Treatment

Then, 100 g of the polysiloxane-treated product was put into a Henschel mixer, and 10.0 g of a polyacrylic acid aqueous solution (polymer concentration: 13% by mass, weight average molecular weight: 20,000, manufactured by Nacalai Co., Ltd.) was sprayed from above while stirring. After spraying, the powder taken out from the mixer was heated in a hot air dryer at 100° C. for 3 hours to obtain a polysiloxane-polyacrylic acid-treated product.

Silane Treatment

A silane coupling treatment solution prepared by stirring 100.0 g of water, 80.0 g of ethanol, 0.003 g of phosphoric acid, and 8.0 g of 3-methacryloyloxypropyl trimethoxysilane as a silane coupling agent at room temperature for 2 hours was added to 100.0 g of the polysiloxane-polyacrylic acid-treated product and stirred for 30 minutes. Thereafter, a heat treatment was performed at 100° C. for 15 hours to obtain filler ECC.

Preparation of Filler EC7

Silane Treatment

A silane coupling treatment solution prepared by stirring 100.0 g of water, 80.0 g of ethanol, 0.003 g of phosphoric acid, and 9.0 g of 3-methacryloyloxypropyl trimethoxysilane as a silane coupling agent at room temperature for 2 hours was added to 100.0 g of the raw material glass G2 and stirred for 30 minutes. Thereafter, a heat treatment was performed at 100° C. for 15 hours to obtain filler EC7.

Preparation of Filler EC8

Acidic Polymer Treatment

Firstly, 100.0 g of filler G2 was put into a Henschel mixer, and 12.0 g of a polyacrylic acid aqueous solution (polymer concentration: 13% by mass, weight average molecular weight: 20,000, manufactured by Nacalai Co., Ltd.) was sprayed from above while stirring. After spraying, the powder taken out from the mixer was heated in a hot air dryer at 100° C. for 3 hours to obtain a polyacrylic acid-treated product.

Silane Treatment

A silane coupling treatment solution prepared by stirring 100.0 g of water, 80.0 g of ethanol, 0.003 g of phosphoric acid, and 9.0 g of 3-methacryloyloxypropyl trimethoxysilane as a silane coupling agent at room temperature for 2 hours was added to 100.0 g of the polyacrylic acid-treated product and stirred for 30 minutes. Thereafter, a heat treatment was performed at 100° C. for 15 hours to obtain filler EC8.

Preparation of Filler EC9

Polysiloxane Treatment

Firstly, 3.0 g of a low condensate of silane compound "MKC SILICATE MS56S" ($SiO2$ content: 56.0% by mass, degree of polymerization: 2 to 100, manufactured by Mitsubishi Chemical Corporation) was added to 100.0 g of the raw material glass G6, and stirred-mixed for 90 minutes. After mixing for a predetermined time, the resulting treated slurry was aged in a hot air dryer at 50° C. for 40 hours, then heated to 150° C. and held for 6 hours, then cooled to obtain a heat treated product. The obtained heat-treated product was placed in a Henschel mixer and crushed at 1800 rpm for 5 minutes. After pulverization, filler EC9 which was a polysiloxane-treated material having good fluidity was obtained.

Preparation of Filler EC10

Silane Treatment

A silane coupling treatment solution prepared by stirring 100.0 g of water, 80.0 g of ethanol, 0.003 g of phosphoric acid, and 3.0 g of 3-methacryloyloxypropyl trimethoxysilane as a silane coupling agent at room temperature for 2 hours was added to 100.0 g of the raw material glass G7 and stirred for 30 minutes. Thereafter, a heat treatment was performed at 100° C. for 15 hours to obtain filler EC10.

pH Measurement

In order to determine the acid-base level of the surface treated filler, pH value was measured. For pH measurement, the pH value of the dispersion prepared by adding 1.0 g of filler to a mixed solution of 40 g of distilled water and 10 g of ethanol and stirring the mixture for 1 hour was measured. Filler having pH value of 7.5 to 10.0 was classified as the basic filler. Filler having pH value more than 10.0 was classified as the non-basic fillers. Also, having pH value less than 7.5 was classified as the non-basic fillers. Table 2 shows the classification results.

TABLE 2

| | |
|---|---|
| E1 | Basic filler |
| E2 | Basic filler |
| E3 | Basic filler |
| E4 | Basic filler |
| E5 | Basic filler |
| E6 | Basic filler |
| E7 | High Basic filler |
| E8 | Basic filler |
| E9 | Basic filler |
| E10 | Basic filler |
| E11 | Basic filler |
| E12 | Basic filler |
| E13 | Basic filler |
| E14 | Basic filler |
| E15 | Basic filler |
| E16 | Basic filler |
| EC1 | Basic filler |
| EC2 | Basic filler |
| EC3 | Non Basic filler |
| EC4 | Basic filler |
| EC5 | Basic filler |
| EC6 | Non Basic filler |
| EC7 | Basic filler |
| EC8 | Basic filler |
| EC9 | Non Basic filler |
| EC10 | High Basic filler |

Preparing Method of One Pack Type Dental Curable Composition

All components shown in Tables 3 to 4 other than the filler (E) were put into a wide mouthed plastic container and mixed by using a mix rotor VMRC-5 under the condition of 100 rpm for 48 hours to prepare a matrix. Then, the matrix and the filler (E) were put into a kneader, stirred uniformly, and then defoamed under vacuum to prepare a dental curable composition of each of Examples A1 to A49 and Comparative Examples CA1 to CA17.

TABLE 3

| | | (E) Filler | | (B) Photopolymerization initiator | |
|---|---|---|---|---|---|
| | (A) Polymerizable monomer | (E1) Surface-treated basic filler | Filler other than (E1) | (B1) Photo sensitizer | (B2) Photoacid generator |
| Example A1 | Bis-GMA/TEGDMA = 60/40 | E1(250) | | CQ(0.3) | B2-1(0.4) |
| Example A2 | Bis-GMA/TEGDMA = 60/40 | E2(250) | | CQ(0.2) | B2-2(0.5) |
| Example A3 | Bis-GMA/TEGDMA = 60/40 | E3(250) | | CQ(0.3) | B2-1(0.5) |
| Example A4 | Bis-GMA/TEGDMA = 60/40 | E4(250) | | CQ(0.2) | B2-3(0.3) |
| Example A5 | Bis-GMA/TEGDMA = 60/40 | E5(250) | | CQ(0.2) | B2-4(1) |
| Example A6 | 2.6E/TEGDMA = 70/30 | E6(250) | | CQ(0.1) | B2-1(2.5) |
| Example A7 | Bis-GMA/TEGDMA = 60/40 | E7(250) | | CQ(0.2) | B2-1(1) |
| Example A8 | Bis-GMA/TEGDMA = 60/40 | E1(150) | EC1(100) | CQ(0.2) | B2-3(1.5) |
| Example A9 | 2.6E/UDMA/TEGDMA = 50/30/20 | E2(50) | EC1(200) | CQ(0.3) | B2-1(1) |
| Example A10 | Bis-GMA/TEGDMA = 60/40 | E3(50) | EC1(100) | CQ(0.2) | B2-2(1) |
| Example A11 | Bis-GMA/TEGDMA = 60/40 | E4(150) | | CQ(0.2) | B2-5(1) |
| Example A12 | Bis-GMA/TEGDMA = 60/40 | E1(50) | | CQ(0.2) | B2-6(0.3) |
| Example A13 | Bis-GMA/TEGDMA = 60/40 | E1(20) | | CQ(0.2) | B2-2(1) |
| Example A14 | Bis-GMA/TEGDMA = 60/40 | E2(10) | | CQ(0.15) | B2-6(1) |
| Example A15 | Bis-GMA/TEGDMA = 60/40 | E7(10) | | CQ(0.1) | B2-1(1.5) |
| Example A16 | Bis-GMA/TEGDMA = 60/40 | E2(5) | EC1(45) | CQ(0.1) | B2-2(1.5) |
| Example A17 | 2.6E/UDMA/TEGDMA = 50/30/20 | E1(600) | | CQ(0.1) | B2-2(2.5) |
| Example A18 | 2.6E/UDMA/TEGDMA = 50/30/20 | E1(200) | EC3(400) | CQ(0.3) | B2-1(0.5) |
| Example A19 | Bis-GMA/TEGDMA = 60/40 | E1(250) | | CQ(0.01) | B2-1(3) |
| Example A20 | Bis-GMA/TEGDMA = 60/40 | E2(250) | | CQ(1.2) | B2-1(0.05) |
| Example A21 | Bis-GMA/TEGDMA = 60/40 | E1(250) | | CQ(0.2) | B2-1(11) |
| Example A22 | Bis-GMA/TEGDMA = 60/40 | E3(200) | | CQ(0.1) | B2-2(0.5) |
| Example A23 | Bis-GMA/TEGDMA = 60/40 | E2(250) | | CQ(0.3) | B2-1(1.5) |
| Example A24 | Bis-GMA/TEGDMA = 60/40 | E3(200) | | CQ(0.3) | B2-2(1) |

TABLE 3-continued

| | (A) Polymerizable monomer | (E) Filler: (E1) Surface-treated basic filler | (E) Filler: Filler other than (E1) | (B) Photopolymerization initiator: (B1) Photo sensitizer | (B) Photopolymerization initiator: (B2) Photoacid generator |
|---|---|---|---|---|---|
| Example A25 | Bis-GMA/TEGDMA = 60/40 | E3(250) | | CQ(0.3) | B2-2(0.2) |
| Example A26 | Bis-GMA/TEGDMA = 60/40 | E4(250) | | CQ(0.2) | B2-6(1) |
| Example A27 | Bis-GMA/TEGDMA = 60/40 | E3(250) | | CQ(0.3) | B2-6(1.5) |
| Example A28 | 2.6E/UDMA/TEGDMA = 50/30/20 | E4(250) | | BAPO(0.4) | B2-4(1) |
| Example A29 | Bis-GMA/TEGDMA = 60/40 | E3(250) | | CQ(0.3), MAPO(0.4) | B2-4(1) |
| Example A30 | Bis-GMA/TEGDMA = 60/40 | E3(250) | | CQ(0.3) | B2-11(0.8) |
| Example A31 | Bis-GMA/TEGDMA = 60/40 | E4(250) | | CQ(0.2) | B2-12(0.8) |
| Example A32 | Bis-GMA/TEGDMA = 60/40 | E3(250) | | CQ(0.3) | B2-13(0.5) |
| Example A33 | Bis-GMA/TEGDMA = 60/40 | E4(250) | | CQ(0.2) | B2-14(0.5) |
| Example A34 | Bis-GMA/UDMA/NPG = 40/20/40 | E3(250) | | CQ(0.08) | B2-1(0.3) |
| Example A35 | Bis-GMA/TEGDMA = 60/40 | E3(250) | | CQ(0.3) | B2-1(0.4), B2-14(0.3) |
| Example A36 | Bis-GMA/TEGDMA = 60/40 | E4(10) | EC3(200) | CQ(0.2) | B2-2(0.3) |
| Example A37 | Bis-GMA/TEGDMA = 60/40 | E8(250) | | CQ(0.1) | B2-4(3) |
| Example A38 | Bis-GMA/TEGDMA = 60/40 | E9(250 ) | | CQ(0.2) | B2-1(0.2) |
| Example A39 | Bis-GMA/TEGDMA = 60/40 | E10(250) | | CQ(0.1) | B2-4(3) |
| Example A40 | Bis-GMA/TEGDMA = 60/40 | E11(400) | | CQ(0.3) | B2-1(2) |
| Example A41 | Bis-GMA/TEGDMA = 60/40 | E12(400) | | CQ(0.3) | B2-1(0.5) |
| Example A42 | Bis-GMA/TEGDMA = 60/40 | E13(500) | | CQ(0.2) | B2-1(1) |
| Example A43 | 2.6E/UDMA/TEGDMA = 50/30/20 | E14(500) | | CQ(0.1) | B2-1(1.3) |
| Example A44 | 2.6E/UDMA/TEGDMA = 50/30/20 | E15(350) | | CQ(0.1) | B2-4(3) |
| Example A45 | MDP/UDMA/TEGDMA = 5/65/30 | E3(25) | EC1(250) | CQ(0.3) | B2-2(1.5) |
| Example A46 | MHPA/Bis-GMA/TEGDMA = 3/57/40 | E8(200) | EC1(50) | CQ(0.1) | B2-4(3) |
| Example A47 | UDMA/TEGDMA = 75/25 | E11(400) | | CQ(0.3) | B2-1(1) |
| Example A48 | UDMA/TEGDMA = 75/25 | E11(400) | | CQ(0.12) | B2-1(1) |
| Example A49 | Bis-GMA/TEGDMA = 60/40 | E16(250) | | CQ(0.1) | B2-4(3) |
| Comparative Example 1 | Bis-GMA/TEGDMA = 60/40 | E1(250) | | — | B2-1(5) |
| Comparative Example 2 | Bis-GMA/TEGDMA = 60/40 | E2(250) | | CQ(0.1) | — |
| Comparative Example 3 | Bis-GMA/TEGDMA = 60/40 | | EC3(250) | CQ(0.1) | B2-2(1) |
| Comparative Example 4 | 2.6E/UDMA/TEGDMA = 50/30/20 | | EC2(200) | CQ(0.3) | B2-1(1.5) |
| Comparative Example 5 | Bis-GMA/TEGDMA = 60/40 | | EC1(150) | CQ(0.1) | B2-2(3) |
| Comparative Example 6 | Bis-GMA/TEGDMA = 60/40 | | EC4(150) | CQ(0.3) | B2-1(1.5) |
| Comparative Example 7 | 2.6E/UDMA/TEGDMA = 50/30/20 | | EC5(150) | CQ(0.2) | B2-2(0.4) |
| Comparative Example 8 | Bis-GMA/TEGDMA = 60/40 | | EC6(150) | CQ(0.2) | B2-2(0.3) |
| Comparative Example 9 | Bis-GMA/TEGDMA = 60/40 | | EC7(250) | CQ(0.1) | B2-1(3) |
| Comparative Example 10 | Bis-GMA/TEGDMA = 60/40 | | EC8(250) | CQ(0.3) | B2-3(1) |
| Comparative Example 11 | Bis-GMA/TEGDMA = 60/40 | | EC9(250) | CQ(0.3) | B2-4(1) |
| Comparative Example 12 | Bis-GMA/TEGDMA = 60/40 | | EC10(250) | CQ(0.3) | B2-5(1) |
| Comparative Example 13 | Bis-GMA/TEGDMA = 60/40 | | EC7(50) | CQ(0.3) | B2-5(1) |
| Comparative Example 14 | 2.6E/UDMA/TEGDMA = 50/30/20 | | EC8(20) | CQ(0.3) | B2-7(0.5) |
| Comparative Example 15 | Bis-GMA/TEGDMA = 60/40 | E4(250) | | CQ(0.2) | B2-3(3) |
| Comparative Example 16 | Bis-GMA/TEGDMA = 60/40 | E3(250) | EC3(50) | CQ(0.3) | B2-1(5) |
| Comparative Example 17 | Bis-GMA/TEGDMA = 60/40 | E4(250) | EC3(250) | CQ(0.2) | B2-2(3) |

TABLE 4

| | (C) Chemical polymerization initiator | (D) polymerization accelerator | | Others | |
|---|---|---|---|---|---|
| | (C1) Organic peroxide | Amine compound | Othe rthan amine compound | Polymerization inhibitor | Fluorescent agent UV absorber |
| Example A1 | — | MDEOA(0.6) | | MeHQ(0.005) | FA(0.005) |
| Example A2 | — | TEA(2) | | MeHQ(0.005) | FA(0.005) |
| Example A3 | — | MDEOA(0.6) | | MeHQ(0.005) | FA(0.005) |
| Example A4 | — | DBGE(0.8) | | MeHQ(0.005) | FA(0.005) |
| Example A5 | — | DBAE(2) | | MeHQ(0.005) | FA(0.005) |
| Example A6 | — | TBA(2) | | MeHQ(0.005) | FA(0.005) |
| Example A7 | — | DMAEMA(2) | | MeHQ(0.005) | FA(0.005) |
| Example A8 | — | DIAEMA(2) | | MeHQ(0.005) | FA(0.005) |
| Example A9 | — | DBGE(1) | | MeHQ(0.005) | FA(0.005) |
| Example A10 | — | DBMA(1.5) | | MeHQ(0.005) | — |
| Example A11 | — | MDEOA(1) | | MeHQ(0.005) | FA(0.005) |
| Example A12 | — | MDEOA(0.6) | | — | FA(0.005) |
| Example A13 | — | MDEOA(2) | | MeHQ(0.005) | FA(0.005) |
| Example A14 | — | TBA(2) | | MeHQ(0.005) | FA(0.005) |
| Example A15 | — | TBA(2), MDEOA(0.3) | | MeHQ(0.005) | — |
| Example A16 | — | TBA(2), DIAEMA(0.8) | | MeHQ(0.005) | FA(0.005) |
| Example A17 | — | TBA(2) | | MeHQ(0.005) | FA(0.005) |
| Example A18 | — | TIPA(1) | | — | FA(0.005) |
| Example A19 | — | TBA(4) | | MeHQ(0.005) | — |
| Example A20 | — | TIPA(0.5) | | MeHQ(0.005) | FA(0.005) |
| Example A21 | — | DIAEMA(5) | | MeHQ(0.005) | FA(0.005) |
| Example A22 | — | DIAEMA(0.5) | | MeHQ(0.005) | FA(0.005) |
| Example A23 | — | DMAEMA(0.05) | | MeHQ(0.005) | FA(0.005) |
| Example A24 | — | DMAEMA(12) | | MeHQ(0.005) | FA(0.005) |
| Example A25 | — | MDEOA(0.3), DMBE(0.3) | | MeHQ(0.005) | FA(0.005), BT(0.5) |
| Example A26 | — | MDEOA(0.3), DMBE(0.3) | | MeHQ(0.005) | FA(0.005) |
| Example A27 | — | — | SnL(1) | MeHQ(0.005) | FA(0.005) |
| Example A28 | — | MDEOA(0.8) | | — | FA(0.005) |
| Example A29 | — | DIAEMA(1) | | MeHQ(0.005) | FA(0.005) |
| Example A30 | — | MDEOA(1.2) | | MeHQ(0.005) | FA(0.005) |
| Example A31 | — | DMAEMA(1) | | MeHQ(0.005) | FA(0.005) |
| Example A32 | — | MDEOA(0.7) | | MeHQ(0.005) | FA(0.005) |
| Example A33 | — | DMAEMA(1) | | MeHQ(0.005) | FA(0.005) |
| Example A34 | — | TBA(2) | | MeHQ(0.005) | FA(0.005) |
| Example A35 | — | MDEOA(0.7) | | MeHQ(0.005) | FA(0.005) |
| Example A36 | — | DIAEMA(2) | | MeHQ(0.005) | FA(0.005) |
| Example A37 | — | TBA(3) | | MeHQ(0.005) | FA(0.005) |
| Example A38 | — | DIAEMA(1.5) | | MeHQ(0.005) | FA(0.005) |
| Example A39 | — | TBA(3) | | MeHQ(0.005) | FA(0.005) |
| Example A40 | — | MDEOA(1) | | MeHQ(0.005) | FA(0.005) |
| Example A41 | — | MDEOA(1) | | MeHQ(0.005) | FA(0.005) |
| Example A42 | — | MDEOA(0.9) | | MeHQ(0.005) | FA(0.005) |
| Example A43 | — | TBA(2) | | MeHQ(0.005) | FA(0.005) |
| Example A44 | — | TBA(2) | | MeHQ(0.005) | FA(0.005) |
| Example A45 | — | MDEOA(0.7) | | MeHQ(0.005) | FA(0.005), BT(0.5) |
| Example A46 | | TBA(3) | | MeHQ(0.005) | FA(0005) |
| Example A47 | TPE(2.0) | MDEOA(1) | | BHT(0.1) | FA(0005) |
| Example A48 | CHP(0.6) | TBA(2) | | BHT(0.1) | FA(0.005) |
| Example A49 | — | TBA(3) | | MeHQ(0.005) | FA(0.005) |
| Comparative Example 1 | — | MDEOA(1) | | MeHQ(0.005) | FA(0.005) |
| Comparative Example 2 | — | MDEOA(1) | | MeHQ(0.005) | FA(0.005) |
| Comparative Example 3 | — | MDEOA(1) | | MeHQ(0.005) | FA(0.005) |
| Comparative Example 4 | — | DMAEMA(1) | | MeHQ(0.005) | FA(0.005) |
| Comparative Example 5 | — | TBA(3) | | MeHQ(0.005) | FA(0.005) |
| Comparative Example 6 | — | DMAEMA(1) | | MeHQ(0.005) | FA(0.005) |
| Comparative Example 7 | — | DMAEMA(1) | | MeHQ(0.005) | FA(0.005) |
| Comparative Example 8 | — | TEA(3) | | MeHQ(0.005) | FA(0.005) |
| Comparative Example 9 | — | TBA(3) | | MeHQ(0.005) | FA(0005) |
| Comparative Example 10 | — | DMAEMA(1) | | MeHQ(0.005) | FA(0005) |
| Comparative Example 11 | — | MDEOA(1) | | MeHQ(0.005) | FA(0005) |

TABLE 4-continued

| | (C) Chemical polymerization initiator | (D) polymerization accelerator | | Others | |
|---|---|---|---|---|---|
| | (C1) Organic peroxide | Amine compound | Othe rthan amine compound | Polymerization inhibitor | Fluorescent agent UV absorber |
| Comparative Example 12 | — | MDEOA(1) | | MeHQ(0.005) | FA(0005) |
| Comparative Example 13 | — | DMAEMA(1) | | MeHQ(0.005) | FA(0.005) |
| Comparative Example 14 | — | MDEOA(1) | | MeHQ(0.005) | FA(0.005) |
| Comparative Example 15 | — | — | | MeHQ(0.005) | FA(0.005) |
| Comparative Example 16 | — | — | | MeHQ(0.005) | FA(0.005) |
| Comparative Example 17 | — | — | | MeHQ(0.005) | FA(0.005) |

Preparing Method of Two Packs Type Dental Curable Composition

All components shown in Tables 5 to 6 and Tables 7 to 8o other than the filler (E) were put into a wide mouthed plastic container and mixed by using a mix rotor VMRC-5 under the condition of 100 rpm for 48 hours to prepare a matrix. Then, the matrix and the filler (E) were put into a kneader, stirred uniformly, and then defoamed under vacuum to prepare a first paste and a second paste, and then the first paste and the second paste were filled into a double syringe (5 mL) manufactured by Mixpack Co., Ltd. to prepare a dental curable composition of each of Examples B1 to B28 and D1 to D39 and Comparative Examples CB1 to CB7 and CD1 to CD6.

TABLE 5

| | | | (E) Filler | | (B) Photopolymerization initiator | |
|---|---|---|---|---|---|---|
| | | (A) Polymerizable monomer | (E1) Surface-treated basic filler | Filler other than (E1) | (B1) Photo sensitizer | (B2) Photoacid generator |
| Example B1 | First paste | Bis-GMA/TEGDMA = 60/40 | E1(200) | — | CQ(0.6) | B2-1(2) |
| | Second paste | Bis-GMA/TEGDMA = 60/40 | E1(200) | — | — | — |
| Example B2 | First paste | Bis-GMA/TEGDMA = 60/40 | E3(250) | — | CQ(0.6) | B2-2(1) |
| | Second paste | Bis-GMA/TEGDMA = 60/40 | E3(250) | — | — | — |
| Example B3 | First paste | Bis-GMA/TEGDMA = 60/40 | E4(250) | — | CQ(0.2) | B2-3(1) |
| | Second paste | Bis-GMA/TEGDMA = 60/40 | E4(250) | — | — | — |
| Example B4 | First paste | Bis-GMA/TEGDMA = 60/40 | E5(250) | — | CQ(0.2) | B2-4(1) |
| | Second paste | Bis-GMA/TEGDMA = 60/40 | E5(250) | — | — | — |
| Example B5 | First paste | 2.6E/TEGDMA = 70/30 | E6(150) | — | CQ(0.15) | B2-5(2.5) |
| | Second paste | 2.6E/TEGDMA = 70/30 | E6(150) | — | — | — |
| Example B6 | First paste | Bis-GMA/TEGDMA = 60/40 | E7(250) | — | CQ(0.2) | B2-1(1) |
| | Second paste | Bis-GMA/TEGDMA = 60/40 | E7(250) | — | — | — |
| Example B7 | First paste | Bis-GMA/TEGDMA = 60/40 | E3(50) | EC1(100) | CQ(0.2) | B2-2(1) |
| | Second paste | Bis-GMA/TEGDMA = 60/40 | E3(50) | EC1(100) | — | — |
| Example B8 | First paste | Bis-GMA/TEGDMA = 60/40 | E1(50) | — | CQ(0.6) | B2-2(1) |
| | Second paste | Bis-GMA/TEGDMA = 60/40 | E1(50) | — | — | — |
| Example B9 | First paste | Bis-GMA/TEGDMA = 60/40 | E1(20) | — | CQ(1) | B2-2(1) |
| | Second paste | Bis-GMA/TEGDMA = 60/40 | E1(20) | — | — | — |
| Example B10 | First paste | Bis-GMA/TEGDMA = 60/40 | E2(5) | EC1(45) | CQ(0.1) | B2-2(1) |
| | Second paste | Bis-GMA/TEGDMA = 60/40 | E2(5) | EC1(45) | — | — |
| Example B11 | First paste | Bis-GMA/TEGDMA = 60/40 | E1(200) | — | CQ(0.01) | B2-1(6) |
| | Second paste | Bis-GMA/TEGDMA = 60/40 | E1(200) | — | — | B2-1(6) |
| Example B12 | First paste | Bis-GMA/TEGDMA = 60/40 | E2(200) | — | CQ(1.1) | B2-1(0.01) |
| | Second paste | Bis-GMA/TEGDMA = 60/40 | E2(200) | — | CQ(1.1) | — |
| Example B13 | First paste | Bis-GMA/TEGDMA = 60/40 | E1(200) | — | CQ(1) | B2-3(2) |
| | Second paste | Bis-GMA/TEGDMA = 60/40 | E1(200) | — | — | B2-3(2) |
| Example B14 | First paste | Bis-GMA/TEGDMA = 60/40 | E3(200) | — | CQ(0.15) | B2-4(3) |
| | Second paste | Bis-GMA/TEGDMA = 60/40 | E3(200) | — | — | — |
| Example B15 | First paste | Bis-GMA/TEGDMA = 60/40 | E2(200) | — | CQ(0.6) | B2-1(1.5) |
| | Second paste | Bis-GMA/TEGDMA = 60/40 | E2(200) | — | — | — |
| Example B16 | First paste | Bis-GMA/TEGDMA = 60/40 | E3(200) | — | CQ(0.3) | — |
| | Second paste | Bis-GMA/TEGDMA = 60/40 | E3(200) | — | — | B2-2(3) |
| Example B17 | First paste | 2.6E/UDMA/TEGDMA = 50/30/20 | E3(200) | — | BAPO(0.2) | B2-1(1) |
| | Second paste | 2.6E/UDMA/TEGDMA = 50/30/20 | E3(200) | — | — | — |
| Example B18 | First paste | Bis-GMA/TEGDMA = 60/40 | E3(250) | — | CQ(0.3), MAPO(0.4) | B2-2(1.0) |
| | Second paste | Bis-GMA/TEGDMA = 60/40 | E3(250) | — | | — |

TABLE 5-continued

| | | (A) Polymerizable monomer | (E) Filler (E1) Surface-treated basic filler | (E) Filler other than (E1) | (B) Photopolymerization initiator (B1) Photo sensitizer | (B) Photopolymerization initiator (B2) Photoacid generator |
|---|---|---|---|---|---|---|
| Example | First paste | Bis-GMA/TEGDMA = 60/40 | E3(250) | — | — | B2-11(0.8) |
| B19 | Second paste | Bis-GMA/TEGDMA = 60/40 | E3(250) | — | CQ(0.3) | — |
| Example | First paste | Bis-GMA/TEGDMA = 60/40 | E4(250) | — | — | B2-12(0.8) |
| B20 | Second paste | Bis-GMA/TEGDMA = 60/40 | E4(250) | — | CQ(0.2) | — |
| Example | First paste | Bis-GMA/TEGDMA = 60/40 | E4(250) | — | CQ(0.2) | B2-14(0.5) |
| B21 | Second paste | Bis-GMA/TEGDMA = 60/40 | E4(250) | — | — | — |
| Example | First paste | Bis-GMA/TEGDMA = 60/40 | E9(300) | — | — | B2-1(1.0) |
| B22 | Second paste | Bis-GMA/TEGDMA = 60/40 | E9(300) | — | CQ(0.6) | — |
| Example | First paste | Bis-GMA/TEGDMA = 60/40 | E8(200) | — | CQ(0.1) | — |
| B23 | Second paste | Bis-GMA/TEGDMA = 60/40 | E8(200) | — | — | B2-4(3) |
| Example | First paste | Bis-GMA/TEGDMA = 60/40 | E10(200) | — | CQ(0.1) | — |
| B24 | Second paste | Bis-GMA/TEGDMA = 60/40 | E10(200) | — | — | B2-4(3) |
| Example | First paste | Bis-GMA/TEGDMA = 60/40 | E11(300) | — | — | B2-1(2.0) |
| B25 | Second paste | Bis-GMA/TEGDMA = 60/40 | E11(300) | — | CQ(0.3) | — |
| Example | First paste | 2.6E/UDMA/TEGDMA = 70/10/20 | E13(300) | — | — | B2-1(1.0) |
| B26 | Second paste | MDP/HEMA/BisGMA/TEGDMA = 10/20/50/10 | — | EC1(300) | CQ(0.2) | — |
| Example | First paste | 2.6E/TEGDMA = 50/50 | E14(450) | — | CQ(0.1) | — |
| B27 | Second paste | 2.6E/TEGDMA = 50/50 | E14(450) | — | — | B2-1(3) |
| Example | First paste | 2.6E/UDMA/TEGDMA = 70/10/20 | E15(300) | — | CQ(0.1) | — |
| B28 | Second paste | MDP/Bis-GMA/TEGDMA = 10/50/40 | — | EC1(300) | — | B2-4(3) |
| Comparative | First paste | Bis-GMA/TEGDMA = 60/40 | E1(200) | — | — | B2-1(5) |
| Example CB1 | Second paste | Bis-GMA/TEGDMA = 60/40 | E1(200) | — | — | — |
| Comparative | First paste | Bis-GMA/TEGDMA = 60/40 | E2(200) | — | CQ(0.1) | — |
| Example CB2 | Second paste | Bis-GMA/TEGDMA = 60/40 | E2(200) | — | — | — |
| Comparative | First paste | Bis-GMA/TEGDMA = 60/40 | — | EC3(200) | CQ(0.1) | B2-2(1.0) |
| Example CB3 | Second paste | Bis-GMA/TEGDMA = 60/40 | — | EC3(200) | — | — |
| Comparative | First paste | 2.6E/UDMA/TEGDMA = 70/10/20 | — | EC2(200) | CQ(0.3) | B2-1(1.5) |
| Example CB4 | Second paste | MDP/Bis-GMA/TEGDMA = 10/50/40 | — | EC3(200) | — | — |
| Comparative | First paste | 2.6E/UDMA/TEGDMA = 70/10/20 | — | EC5(150) | CQ(0.2) | B2-2(1.0) |
| Example CB5 | Second paste | MDP/Bis-GMA/TEGDMA = 10/50/40 | — | EC5(150) | — | — |
| Comparative | First paste | Bis-GMA/TEGDMA = 60/40 | — | EC7(200) | CQ(0.3) | B2-1(1.0) |
| Example CB6 | Second paste | Bis-GMA/TEGDMA = 60/40 | — | EC7(200) | — | — |
| Comparative | First paste | Bis-GMA/TEGDMA = 60/40 | E4(250) | — | CQ(0.2) | — |
| Example CB7 | Second paste | Bis-GMA/TEGDMA = 60/40 | E4(250) | — | — | B2-3(3) |

TABLE 6

| | | (C) Chemical polymerization initiator (C1) Organic peroxide | (D) polymerization accelerator Amine compound | (D) polymerization accelerator Other than amine compound | Others Polymerization inhibitor | Others Fluorescent agent |
|---|---|---|---|---|---|---|
| Example | First paste | CHP(2) | — | — | BHT(0.1) | — |
| B1 | Second paste | — | MDEOA(1) | BTU(1), VOA(0.01) | — | — |
| Example | First paste | — | MDEOA(1) | PTU(1), VOA(0.01) | MeHQ(0.005) | FA(0.005) |
| B2 | Second paste | CHP(2) | — | — | BHT(0.1) | — |
| Example | First paste | — | DBGE(2) | DEPT(1.5) | MeHQ(0.02) | FA(0.005) |
| B3 | Second paste | BPO(2) | — | — | BHT(0.15) | — |
| Example | First paste | BPO(2) | — | — | BHT(0.15) | FA(0.005) |
| B4 | Second paste | — | DBAE(2) | DEPT(1.5) | BHT(0.01) | BT(0.5) |
| Example | First paste | — | TBA(2) | DHPT(1.5) | MeHQ(0.005) | BT(0.5) |
| B5 | Second paste | BPO(1.5) | — | — | BHT(0.01) | FA(0.005) |
| Example | First paste | BPO(1.5) | — | — | BHT(0.01) | FA(0.005) |
| B6 | Second paste | — | DMAEMA(2) | DHPT(1.5) | MeHQ(0.005) | BT(0.5) |
| Example | First paste | — | DBGE(2) | DEPT(1.5), KPS(1) | MeHQ(0.005) | — |
| B7 | Second paste | BPO(1.5) | — | — | BHT(0.01) | BT(0.5) |
| Example | First paste | TMBH(3) | — | — | BHT(0.1) | FA(0.005) |
| B8 | Second paste | — | MDEOA(1) | PTU(2), CAA(0.01) | MeHQ(0.005) | — |
| Example | First paste | — | MDEOA(2) | PTU(2), VOA(0.01) | MeHQ(0.005) | FA(0.005) |
| B9 | Second paste | TMBH(3) | — | — | BHT(0.1) | — |
| Example | First paste | — | — | BTU(1), TMBA(1) | MeHQ(0.005) | FA(0.005) |
| B10 | Second paste | TMBH(3) | TBA(2) | — | BHT(0.2) | — |
| Example | First paste | TMBH(3) | — | — | BHT(0.1) | — |
| B11 | Second paste | — | DIAEMA(10) | PTU(2), CAA(0.1) | MeHQ(0.005) | — |
| Example | First paste | TPE(3) | — | — | BHT(0.1) | FA(0.005) |
| B12 | Second paste | — | TIPA(2) | VOA(.1), CAA(0.1) | MeHQ(0.005) | — |

TABLE 6-continued

| | | (C) Chemical polymerization initiator | (D) polymerization accelerator | | Others | |
|---|---|---|---|---|---|---|
| | | (C1) Organic peroxide | Amine compound | Other than amine compound | Polymerization inhibitor | Fluorescent agent |
| Example B13 | First paste | — | DIAEMA(10) | BTU(2) | MeHQ(0.005) | FA(0.005) |
| | Second paste | TMBH(3) | — | — | BHT(0.1) | — |
| Example B14 | First paste | — | TBA(2) | BTU(2) | MeHQ(0.005) | FA(0.005) |
| | Second paste | TMBH(3) | — | — | BHT(0.1) | — |
| Example B15 | First paste | BPO(1.5) | — | — | MeHQ(0.005) | FA(0.005) |
| | Second paste | — | DMAEMA(0.1) | — | — | — |
| Example B16 | First paste | — | DMAEMA(22) | VOA(0.1), CAA(0.1) | BHT(0.1) | FA(0.005) |
| | Second paste | TPE(3) | — | — | MeHQ(0.005) | — |
| Example B17 | First paste | CHP(3.5) | — | — | BHT(0.1) | FA(0.005) |
| | Second paste | — | MDEOA(0.8) | BTU(2) | MeHQ(0.005) | — |
| Example B18 | First paste | — | DIAEMA(1) | BTU(2), PTSA(1) | MeHQ(0.005) | FA(0.005) |
| | Second paste | TMBH(4) | — | — | BHT(0.1) | — |
| Example B19 | First paste | TMBH(4) | — | — | MeHQ(0.005) | — |
| | Second paste | — | MDEOA(1.2) | BTU(2), TMBA(0.8) | MeHQ(0.005) | FA(0.005) |
| Example B20 | First paste | TPE(1),TMBH(2) | — | — | BHT(0.1) | FA(0.005) |
| | Second paste | — | DMAEMA(1) | BTU(2), PTSA(1) | MeHQ(0.005) | — |
| Example B21 | First paste | — | TBA(2) | PTU(2), CAA(0.1) | MeHQ(0.005) | FA(0.005) |
| | Second paste | TMBH(4) | — | — | BHT(0.1) | — |
| Example B22 | First paste | — | DIAEMA(1.5) | DHPT(2) | MeHQ(0.005) | FA(0.005) |
| | Second paste | BPO(1.5) | — | — | BHT(0.1) | BT(0.5) |
| Example B23 | First paste | — | TBA(3) | DHPT(2) | MeHQ(0.005) | FA(0.005) |
| | Second paste | BPO(1.5) | — | — | BHT(0.1) | BT(0.5) |
| Example B24 | First paste | BPO(1.5) | TBA(3) | — | BHT(0.1) | FA(0.005) |
| | Second paste | — | — | DHPT(2) | — | BT(0.5) |
| Example B25 | First paste | — | MDEOA(1) | DEPT(1.5) | MeHQ(0.005) | FA(0.005) |
| | Second paste | BPO(1.5) | — | — | BHT(0.1) | BT(0.5) |
| Example B26 | First paste | TMBH(4) | TBA(2) | — | MeHQ(0.005) | FA(0.005) |
| | Second paste | — | — | BTU(1), VOA(0.01) | — | — |
| Example B27 | First paste | — | TBA(2) | BTU(1), VOA(0.01) | MeHQ(0.005) | FA(0.005) |
| | Second paste | TMBH(4) | — | — | BHT(0.1) | — |
| Example B28 | First paste | TMBH(3.5) | TBA(2) | — | MeHQ(0.005) | FA(0.005) |
| | Second paste | — | — | PTU(2), CAA(0.1) | BHT(0.1) | — |
| Comparative Example CB1 | First paste | — | TBA(1) | PTU(2), CAA(0.1) | MeHQ(0.005) | FA(0.005) |
| | Second paste | TMBH(2.5) | — | — | BHT(0.1) | BT(0.5) |
| Comparative Example CB2 | First paste | — | TBA(2) | PTU(2), CAA(0.1) | MeHQ(0.005) | FA(0.005) |
| | Second paste | TMBH(2.5) | — | — | BHT(0.1) | — |
| Comparative Example CB3 | First paste | — | TEA(1) | PTU(2), CAA(0.1) | MeHQ(0.005) | FA(0.005) |
| | Second paste | TMBH(2.5) | — | — | BHT(0.1) | — |
| Comparative Example CB4 | First paste | — | MDEOA(1) | DHPT(2) | MeHQ(0.005) | FA(0.005) |
| | Second paste | BPO(1.5) | — | — | BHT(0.1) | BT(0.5) |
| Comparative Example CB5 | First paste | — | DIAEMA(0.6) | DHPT(2) | MeHQ(0.005) | FA(0.005) |
| | Second paste | BPO(1.5) | — | — | BHT(0.1) | BT(0.5) |
| Comparative Example CB6 | First paste | — | DIAEMA(1) | DHPT(2) | MeHQ(0.005) | FA(0.005) |
| | Second paste | BPO(1.5) | — | — | BHT(0.1) | BT(0.5) |
| Comparative Example CB7 | First paste | — | — | DHPT(2), VOA(0.05) | MeHQ(0.005) | FA(0.005) |
| | Second paste | TPE(3) | — | — | BHT(0.1) | BT(0.5) |

TABLE 7

| | | | (E) Filler | | (B) Photopolymerization initiator | |
|---|---|---|---|---|---|---|
| | | (A) Polymerizable monomer | (E1) Surface-treated basic filler | Filler other than (E1) | (B1) Photo sensitizer | (B2) Photoacid |
| Example D1 | First paste | Bis-GMA/TEGDMA = 60/40 | E1(250) | — | CQ(0.6) | — |
| | Second paste | Bis-GMA/TEGDMA = 60/40 | E1(250) | — | — | — |
| Example D2 | First paste | Bis-GMA/TEGDMA = 60/40 | E3(250) | — | — | — |
| | Second paste | Bis-GMA/TEGDMA = 60/40 | E3(250) | — | CQ(0.3) | — |
| Example D3 | First paste | Bis-GMA/TEGDMA = 60/40 | E4(250) | — | — | — |
| | Second paste | Bis-GMA/TEGDMA = 60/40 | E4(250) | — | CQ(1) | — |
| Example D4 | First paste | Bis-GMA/TEGDMA = 60/40 | E5(250) | — | CQ(0.2) | — |
| | Second paste | Bis-GMA/TEGDMA = 60/40 | E5(250) | — | — | — |
| Example D5 | First paste | Bis-GMA/NPG/UDMA = 40/40/20 | E6(250) | — | CQ(0.6) | — |
| | Second paste | Bis-GMA/NPG/UDMA = 40/40/20 | E6(250) | — | — | — |
| Example D6 | First paste | Bis-GMA/TEGDMA = 60/40 | E7(250) | — | — | — |
| | Second paste | Bis-GMA/TEGDMA = 60/40 | E7(250) | — | CQ(0.1) | — |

TABLE 7-continued

| | | (A) Polymerizable monomer | (E) Filler<br>(E1)<br>Surface-treated basic filler | <br>Filler other than (E1) | (B) Photopolymerization initiator<br>(B1)<br>Photo sensitizer | <br><br>(B2)<br>Photoacid |
|---|---|---|---|---|---|---|
| Example | First paste | Bis-GMA/TEGDMA = 60/40 | E1(20) | — | — | — |
| D7 | Second paste | Bis-GMA/TEGDMA = 60/40 | E1(20) | — | CQ(0.8) | — |
| Example | First paste | Bis-GMA/TEGDMA = 60/40 | E2(10) | EC1(80) | CQ(0.15) | — |
| D8 | Second paste | Bis-GMA/TEGDMA = 60/40 | E2(10) | EC1(80) | — | — |
| Example | First paste | Bis-GMA/TEGDMA = 60/40 | E2(5) | EC1(45) | — | B2-2(1) |
| D9 | Second paste | Bis-GMA/TEGDMA = 60/40 | E2(5) | EC1(45) | CQ(0.6) | — |
| Example | First paste | Bis-GMA/NPG/UDMA = 40/40/20 | E4(250) | — | BAPO(0.4) | — |
| D10 | Second paste | Bis-GMA/NPG/UDMA = 40/40/20 | E4(250) | — | — | — |
| Example | First paste | Bis-GMA/TEGDMA = 60/40 | E8(250) | — | — | — |
| D11 | Second paste | Bis-GMA/TEGDMA = 60/40 | E8(250) | — | CQ(1.2) | B2-4(0.5) |
| Example | First paste | Bis-GMA/TEGDMA = 60/40 | E9(250) | — | CQ(0.2) | |
| D12 | Second paste | Bis-GMA/TEGDMA = 60/40 | E9(250) | — | — | — |
| Example | First paste | Bis-GMA/TEGDMA = 60/40 | E10(250) | — | — | — |
| D13 | Second paste | Bis-GMA/TEGDMA = 60/40 | E10(250) | — | CQ(0.4) | — |
| Example | First paste | 2.6E/UDMA/TEGDMA = 50/30/20 | E11(400) | — | CQ(0.3) | — |
| D14 | Second paste | 2.6E/UDMA/TEGDMA = 50/30/20 | E11(400) | — | — | — |
| Example | First paste | Bis-GMA/TEGDMA = 60/40 | E12(300) | — | — | — |
| D15 | Second paste | Bis-GMA/TEGDMA = 60/40 | E12(300) | — | CQ(0.3) | — |
| Example | First paste | Bis-GMA/TEGDMA = 60/40 | E13(300) | — | | — |
| D16 | Second paste | Bis-GMA/TEGDMA = 60/40 | E13(300) | — | CQ(0.6) | B2-1(1) |
| Example | First paste | Bis-GMA/NPG/UDMA = 40/40/20 | E14(300) | — | CQ(0.1) | — |
| D17 | Second paste | Bis-GMA/NPG/UDMA = 40/40/20 | E14(300) | — | — | — |
| Example | First paste | Bis-GMA/NPG/UDMA = 40/40/20 | E15(100) | EC1(150) | — | — |
| D18 | Second paste | Bis-GMA/NPG/UDMA = 40/40/20 | — | EC1(250) | CQ(0.6) | — |
| Example | First paste | Bis-GMA/TEGDMA = 60/40 | E6(250) | — | CQ(1) | — |
| D19 | Second paste | Bis-GMA/TEGDMA = 60/40 | E6(250) | — | CQ(0.3) | — |
| Example | First paste | Bis-GMA/TEGDMA = 60/40 | E6(250) | — | — | — |
| D20 | Second paste | Bis-GMA/TEGDMA = 60/40 | E6(250) | — | — | — |
| Example | First paste | Bis-GMA/TEGDMA = 60/40 | E6(250) | — | CQ(0.4) | — |
| D21 | Second paste | Bis-GMA/TEGDMA = 60/40 | E6(250) | — | | — |
| Example | First paste | Bis-GMA/TEGDMA = 60/40 | E6(250) | — | | — |
| D22 | Second paste | Bis-GMA/TEGDMA = 60/40 | E6(250) | — | CQ(1) | — |
| Example | First paste | UDMA/HEMA/TEGDMA = 70/10/20 | E1(150) | — | | — |
| D23 | Second paste | MDP/HEMA/UDMA/ TEGDMA = 15/10/65/10 | — | EC1(150) | CQ(0.2) | — |
| Example | First paste | UDMA/TEGDMA = 70/30 | E1(30) | EC1(120) | CQ(0.2) | — |
| D24 | Second paste | MDP/AET/UDMA/ TEGDMA = 45/20/10/25 | — | EC1(150) | — | — |
| Example | First paste | UDMA/TEGDMA = 70/30 | E1(10) | EC1(90) | CQ(0.2) | — |
| D25 | Second paste | MDP/UDMA/TEGDMA = 20/60/20 | — | EC1(100) | — | — |
| Example | First paste | UDMA/TEGDMA = 70/30 | E1(100), E3(50) | — | — | — |
| D26 | Second paste | MDP/MET/UDMA/ TEGDMA = 10/5/60/25 | — | EC1(150) | CQ(0.2) | — |
| Example | First paste | MDP/UDMA/TEGDMA = 1/70/29 | E 12(100), E3(50) | — | — | — |
| D27 | Second paste | UDMA/TEGDMA = 70/30 | — | EC1(150) | CQ(0.3) | — |
| Example | First paste | UDMA/TEGDMA = 70/30 | E13(100), E3(50) | — | — | — |
| D28 | Second paste | MHPA/MET/UDMA/ TEGDMA = 2/2/70/26 | E8(20) | EC1(130) | CQ(0.6) | — |
| Example | First paste | UDMA/TEGDMA = 70/30 | E11(100), E3(50) | — | CQ(1) | — |
| D29 | Second paste | MHPA/META/UDMA/ TEGDMA = 10/5/60/25 | — | EC1(150) | — | — |
| Example | First paste | UDMA/TEGDMA = 70/30 | E1(100), E3(50) | — | — | — |
| D30 | Second paste | MHPA/MDP/UDMA/ GDMA = 5/5/70/20 | — | EC1(150) | CQ(0.5) | — |
| Example | First paste | UDMA/TEGDMA = 70/30 | E14(100), E3(50) | — | — | — |
| D31 | Second paste | MHPA/META/Bis-GMA/ TEGDMA = 10/5/60/25 | — | EC1(150) | CQ(0.2) | — |
| Example | First paste | UDMA/TEGDMA = 70/30 | E1(100), E3(50) | — | CQ(0.2) | — |
| D32 | Second paste | MHPA/META/Bis-GMA/ TEGDMA = 2/2/70/26 | — | EC1(150) | — | — |
| Example | First paste | UDMA/TEGDMA = 70/30 | E1(150), E3(50) | — | CQ(0.1) | — |
| D33 | Second paste | MHPA/META/Bis-GMA/ TEGDMA = 10/5/60/25 | E8(10) | EC1(190) | — | — |
| Example | First paste | UDMA/TEGDMA = 70/30 | E10(220) | — | CQ(0.1) | B2-4(2) |
| D34 | Second paste | MHPA/MDP/UDMA/ GDMA = 5/5/70/20 | — | EC1(220) | — | — |
| Example | First paste | UDMA/TEGDMA = 70/30 | E1(100), E3(50) | — | — | — |
| D35 | Second paste | META/HEMA/UDMA/ TEGDMA = 15/20/60/15 | — | EC1(150) | CQ(0.2) | B2-4(2) |
| Example | First paste | 2.6E/TEGDMA = 80/20 | E1(100), E3(50) | — | — | — |
| D36 | Second paste | MET/HEMA/UDMA/ TEGDMA = 15/20/60/15 | — | EC1(150) | CQ(0.2) | — |

TABLE 7-continued

| | | (A) Polymerizable monomer | (E) Filler (E1) Surface-treated basic filler | (E) Filler Filler other than (E1) | (B) Photopolymerization initiator (B1) Photo sensitizer | (B) Photopolymerization initiator (B2) Photoacid |
|---|---|---|---|---|---|---|
| Example | First paste | UDMA/HEMA = 70/30 | E6(200) | — | — | — |
| D37 | Second paste | MDP/2.6E/TEGDMA = 15/70/15 | E6(5) | EC1(195) | CQ(0.6) | |
| Example D38 | First paste | UDMA/MPTMS/ TEGDMA = 70/10/20 | E1(100), E3(50) | — | — | — |
| | Second paste | MDP/MET/UDMA/ TEGDMA = 10/5/60/25 | — | EC1(150) | CQ(0.2) | B2-3(2) |
| Example D39 | First paste | UDMA/MPTMS/MDDT/ TEGDMA = 70/10/3/17 | E1(100), E3(50) | — | — | — |
| | Second paste | MDP/MET/UDMA/ TEGDMA = 10/5/60/25 | — | EC1(150) | CQ(0.2) | B2-3(2) |
| Comparative | First paste | Bis-GMA/TEGDMA = 60/40 | E1(250) | — | — | — |
| Example CD1 | Second paste | Bis-GMA/TEGDMA = 60/40 | E1(250) | — | — | — |
| Comparative | First paste | Bis-GMA/TEGDMA = 60/40 | E1(250) | — | — | — |
| Examole CD2 | Second paste | Bis-GMA/TEGDMA = 60/40 | E1(250) | — | — | — |
| Comparative | First paste | Bis-GMA/TEGDMA = 60/40 | — | EC4(150) | — | — |
| Example CD3 | Second paste | Bis-GMA/TEGDMA = 60/40 | — | EC4(150) | CQ(0.3) | — |
| Comparative Example CD4 | First paste | Bis-GMA/MOTMS/ TEGDMA = 65/20/15 | — | EC3(200) | CQ(0.1) | — |
| | Second paste | MDP/HEMA/Bis-GMA/ TEGDMA = 10/15/60/15 | — | EC3(200) | — | — |
| Comparative Example CD5 | First paste | Bis-GMA/MPTMS/ TEGDMA = 65/20/15 | — | EC4(150) | — | — |
| | Second paste | MHPA/HEMA/Bis-GMA/ TEGDMA = 10/15/60/15 | — | EC1(150) | — | — |
| Comparative | First paste | UDMA/TEGDMA/ | — | EC10(250) | CQ(0.3) | — |
| Example CD6 | Second paste | GDMA = 60/20/20 | | | | |
| | | MDP/MET/UDMA/ TEGDMA = 10/15/60/15 | — | EC1(250) | — | B2-2(1) |

TABLE 8

| | | (C) Chemical polymerization initiator (C1) Organic peroxide | (D) polymerization accelerator Amine compound | (D) polymerization accelerator Othe rthan amine compound | Others Polymerization inhibitor | Others Fluorescent agent |
|---|---|---|---|---|---|---|
| Example | First paste | CHP(2) | — | — | BHT(0.1) | FA(0.01) |
| D1 | Second paste | — | DMBE(0.6) | BTU(1), VOA(0.01) | — | BT(0.5) |
| Example | First paste | — | — | PTU(1), CAA(0.1) | — | FA(0.01) |
| D2 | Second paste | CHP(3) | DMBE(0.3) | — | BHT(0.1) | BT(0.5) |
| Example | First paste | TMBH(3) | — | — | BHT(0.1) | FA(0.01) |
| D3 | Second paste | — | — | BTU(1) | — | — |
| Example | First paste | BPO(1.5) | — | — | BHT(0.1) | FA(0.01) |
| D4 | Second paste | — | DMBE(0.6) | DEPT(1) | — | BT(0.5) |
| Example | First paste | BPO(1.5) | — | — | BHT(0.1) | BT(0.5) |
| D5 | Second paste | — | DMBE(0.1) | DHPT(1.5) | — | FA(0.005) |
| Example | First paste | CHP(1) | — | — | BHT(0.1) | FA(0.005) |
| D6 | Second paste | — | DMBE(0.6) | BTU(1) | — | BT(0.5) |
| Example | First paste | CHP(3) | DMBE(0.1) | — | BHT(0.1) | FA(0.005) |
| D7 | Second paste | — | — | BTU(1) | — | BT(0.5) |
| Example | First paste | TMBH(4) | — | — | BHT(0.1) | FA(0.005) |
| D8 | Second paste | — | DMBE(0.6) | BTU(3) | — | BT(0.5) |
| Example | First paste | CHP(1) | — | — | BHT(0.1) | FA(0.005) |
| D9 | Second paste | — | — | BTU(1), CAA(0.1) | — | — |
| Example | First paste | — | — | BTU(1), CAA(0.2) | — | FA(0.005) |
| D10 | Second paste | CHP(3) | | — | BHT(0.1) | BT(0.5) |
| Example | First paste | CHP(3) | — | — | BHT(0.1) | FA(0.005) |
| D11 | Second paste | — | | BTU(1), TMBA(1) | — | BT(0.5) |
| Example | First paste | TMBH(2), TPE(2) | | | BHT(0.1) | FA(0.005) |
| D12 | Second paste | | — | BTU(1), | — | BT(0.5) |
| Example | First paste | CHP(3) | DMBE(0.2) | | BHT(0.1) | FA(0.005) |
| D13 | Second paste | — | | BTU(1.5), TMBA(1) | — | BT(0.5) |
| Example | First paste | CHP(2) | — | — | BHT(0.1) | FA(0.005) |
| D14 | Second paste | — | DMBE(0.6) | PTU(0.5), VOA(0.03) | — | BT(0.5) |

TABLE 8-continued

| | | (C) Chemical polymerization initiator | (D) polymerization accelerator | | Others | |
|---|---|---|---|---|---|---|
| | | (C1) Organic peroxide | Amine compound | Othe rthan amine compound | Polymerization inhibitor | Fluorescent agent |
| Example | First paste | TMBH(4) | — | — | BHT(0.1) | FA(0.005) |
| D15 | Second paste | — | DMBE(0.6) | BTU(0.5), CAA(0.1) | — | BT(0.5) |
| Example | First paste | CHP(3) | — | — | BHT(0.1) | FA(0.005) |
| D16 | Second paste | — | — | PTU(2) | — | BT(0.5) |
| Example | First paste | CHP(3) | — | — | BHT(0.1) | FA(0.005) |
| D17 | Second paste | — | DMBE(0.6) | BTU(2) | — | BT(0.5) |
| Example | First paste | CHP(2.5) | — | — | BHT(0.1) | FA(0.005) |
| D18 | Second paste | — | — | PTU(1), CAA(0.1) | — | — |
| Example | First paste | CHP(0.1) | DMBE(1) | — | — | BT(1) |
| D19 | Second paste | — | DIAEMA(12) | BTU(5), PTSA(3) | — | BT(0.5) |
| Example | First paste | CHP(11) | — | — | BHT(0.5) | — |
| D20 | Second paste | — | — | BTU(0.1) | — | BT(0.5) |
| Example | First paste | CHP(3) | — | — | BHT(0.1) | — |
| D21 | Second paste | — | — | PTU(1.2), CAA(0.1) | — | — |
| Example | First paste | CHP(1) | — | — | BHT(0.1) | — |
| D22 | Second paste | — | — | BTU(5) | — | — |
| Example | First paste | TMBH(4) | DMBE(0.6) | — | BHT(0.1) | FA(0.005) |
| D23 | Second paste | — | — | BTU(0.5), VOA(0.03) | — | — |
| Example | First paste | TMBH(4) | DMBE(0.6) | — | — | FA(0.005) |
| D24 | Second paste | — | — | PTU(0.5), VOA(0.03) | BHT(0.1) | BT(0.5) |
| Example | First paste | CHP(3) | DMBE(0.6) | — | MeHQ(0.005) | FA(0.005) |
| D25 | Second paste | — | — | BTU(1) | BHT(0.1) | BT(0.5) |
| Example | First paste | CHP(2) | DMBE(0.6) | — | BHT(0.1) | FA(0.005) |
| D26 | Second paste | — | — | — | — | BT(0.5) |
| Example | First paste | TMBH(4) | — | — | MeH0(0.005) | FA(0.005) |
| D27 | Second paste | — | DMBE(0.6) | PTU(0.5), VOA(0.03) | BHT(0.1) | BT(0.5) |
| Example | First paste | — | DMBE(0.6) | DHPT(2), TMBA(0.5) | MeHQ(0.005) | FA(0.005) |
| D28 | Second paste | BPO(1.2) | — | — | BHT(0.1) | BT(0.5) |
| Example | First paste | TMBH(3) | — | — | BHT(0.1) | FA(0.005) |
| D29 | Second paste | — | — | BTU(2) | — | — |
| Example | First paste | CHP(3) | DMBE(0.6) | | BHT(0.1) | FA(0.005) |
| D30 | Second paste | — | — | BTU(0.5), VOA(0.05) | — | BT(0.5) |
| Example | First paste | TMBH(4) | — | — | BHT(0.1) | FA(0.005) |
| D31 | Second paste | — | DMBE(0.6) | BTU(0.3), VOA(0.1) | — | BT(0.5) |
| Example | First paste | — | — | PTU(0.3), VOA(0.1) | MeHQ(0.005) | FA(0.005) |
| D32 | Second paste | CHP(3) | DMBE(0.6) | — | MeHQ(0.1) | BT(0.5) |
| Example | First paste | | TBA(3) | — | MeHQ(0.005) | FA(0.005) |
| D33 | Second paste | TMBH(4) | | — | BHT(0.1) | — |
| Example | First paste | — | TBA(3) | BTU(1), CAA(0.2) | MeHQ(0.005) | FA(0.005) |
| D34 | Second paste | — | — | — | — | — |
| Example | First paste | TMBH(4) | — | — | MeHQ(0.1) | FA(0.005) |
| D35 | Second paste | — | — | BTU(1.0) | — | — |
| Example | First paste | CHP(3) | — | — | BHT(0.1) | FA(0.005) |
| D36 | Second paste | — | DMBE(0.6) | PTU(1), CAA(0.2) | — | BT(0.5) |
| Example | First paste | | DMBE(0.6) | DEPT(1), TMBA(1) | MeHQ(0.005) | FA(0.005) |
| D37 | Second paste | BPO(1.2) | — | — | BHT(0.1) | BT(0.5) |
| Example | First paste | TMBH(3) | — | — | BHT(0.1) | FA(0.005) |
| D38 | Second paste | — | TBA(3) | PTU(0.3), VOA(0.04) | — | — |
| Example | First paste | — | TBA(2) | BTU(0.3), VOA(0.04) | MeHQ(0.005) | FA(0.005) |
| D39 | Second paste | CHP(3) | — | — | BHT(0.1) | — |
| Comparative | First paste | — | — | — | BHT(0.1) | — |
| Example CD1 | Second paste | — | — | PTU(4), VOA(0.1) | — | — |
| Comparative | First paste | TMBH(2), TPE(5) | — | — | BHT(0.1) | — |
| Example CD2 | Second paste | — | — | — | — | — |
| Comparative | First paste | CHP(2.5) | DMBE(0.3) | — | BHT(0.1) | — |
| Example CD3 | Second paste | — | — | PTU(0.3), VOA(0.04) | | BT(0.5) |
| Comparative | First paste | TMBH(3) | — | — | MeHQ(0.005) | FA(0.005) |
| Example CD4 | Second paste | — | — | BTU(2) | — | — |
| Comparative | First paste | TMBH(3) | — | — | BHT(0.1) | — |
| Example CD5 | Second paste | — | — | BTU(1), VOA(0.04) | MeHQ(0.005) | — |
| Comparative | First paste | CHP(3) | — | — | BHT(0.1) | FA(0.005) |
| Example CD6 | Second paste | — | — | PTU(1), VOA(0.04) | MeHQ(0.005) | — |

Acceleration Test Condition

One pack type dental curable composition or two packs type dental curable composition filled in each container was left to stand in a storage room set at 40° C. (Yamato Scientific Co., Ltd.) and stored for 6 months.

Evaluation 1-1: Flexural Strength (Photopolymerization)

The dental curable composition was filled into a stainless steel mold, and the cover glasses were placed on both sides to press with a glass kneading plate. Thereafter, light was irradiated for 10 seconds to 5 locations by using the photopolymerization irradiator (Blue Shot manufactured by SHOFU INC.) to cure the composition. After curing, the cured product was removed from the mold, and light was irradiated to the backside in the same manner again to use as a test specimen (25×2×2 mm rectangular shape). The test specimen was immersed in water at 37° C. for 24 hours, and thereafter flexural test was performed. For the composition containing the chemical polymerization initiator, measurement was performed within 2 hours after the end of light irradiation. The flexural test was conducted at a distance between supporting points of 20 mm and at a crosshead speed of 1 mm/min using an Instron universal testing machine (manufactured by Instron). Evaluation criteria were as follows.

Excellent flexural strength: 100 MPa or more

Sufficient flexural strength: 90 MPa or more and less than 100 MPa

Slightly inferior flexural strength: 80 MPa or more and less than 90 MPa

Insufficient: less than 80 MPa

In the case of containing less than 100 parts by mass of the (E) filler with respect to 100 parts by mass of the (A) polymerizable monomer, evaluation criteria for flexural strength of the one pack type dental curable composition and the two packs type dental curable composition were as follows.

Excellent flexural strength: 80 MPa or more

Sufficient flexural strength: 70 MPa or more and less than 80 MPa

Slightly inferior flexural strength: 60 MPa or more and less than 70 MPa

Insufficient: less than 60 MPa

Evaluation 1-2: Flexural Strength (Chemical Polymerization)

The dental curable composition was filled into a stainless steel mold, and the cover glasses were placed on both sides to press with a glass kneading plate to stand in a thermostatic chamber set at 37° C. for 1 hour. After taken out the cured product from the mold, the test specimen was immersed in water at 37° C. for 24 hours, and thereafter flexural test was performed. The flexural test was conducted at a distance between supporting points of 20 mm and at a crosshead speed of 1 mm/min using an Instron universal testing machine (manufactured by Instron). Evaluation criteria were as follows.

Excellent flexural strength: 100 MPa or more

Sufficient flexural strength: 90 MPa or more and less than 100 MPa

Slightly inferior flexural strength: 80 MPa or more and less than 90 MPa

Insufficient: less than 80 MPa

In the case of containing less than 100 parts by mass of the (E) filler with respect to 100 parts by mass of the (A) polymerizable monomer, evaluation criteria were as follows.

Excellent flexural strength: 80 MPa or more

Sufficient flexural strength: 70 MPa or more and less than 80 MPa

Slightly inferior flexural strength: 60 MPa or more and less than 70 MPa

Insufficient: less than 60 MPa

Evaluation 2: Flexural Strength of Acceleration Tested Composition Before Curing After standing in a thermostatic chamber set at 40° C. (Yamato Scientific Co., Ltd.) for 6 months, flexural strength of the dental curable composition was measured according to <Evaluation 1-1: Flexural strength (photopolymerization)> or <Evaluation 1-2: Flexural strength (Chemical polymerization)>. Comparison with the flexural strength of the composition before storage was performed using formula (3). When the change from before storage in a thermostatic chamber set at 40° C. was −5% or more, it was determined to have high storage stability. When the change from before storage in a thermostatic chamber set at 40° C. was less than −5% to −10%, it was determined that the storage stability was sufficient. When the change from before storage in a thermostatic chamber set at 40° C. was less than −10% to −15%, it was determined that the storage stability was slightly poor. When the change from before storage in a thermostatic chamber set at 40° C. was less than −20%, it was determined that the storage stability was extremely poor and insufficient.

((flexural strength after storage (MPa)−flexural strength before storage (MPa))/(flexural strength before storage (MPa))×100[%] [Formula (3)]

Evaluation 3: Flexural Strength of Acceleration Tested Composition after Curing

After standing in a thermostatic chamber set at 40° C. (Yamato Scientific Co., Ltd.) for 6 months, flexural strength of the test specimen prepared according to <Evaluation 1-1: Flexural strength (photopolymerization)> or <Evaluation 1-2: Flexural strength (Chemical polymerization)> was measured. Comparison with the flexural strength of the composition before storage in the thermostatic chamber set at 40° C. was performed using formula (4). When the change from before storage was −10% or more, it was determined to have high storage stability. When the change from before storage was less than −10% to −20%, it was determined that the storage stability was sufficient. When the change from before storage was less than −20% to −35%, it was determined that the storage stability was slightly poor. When the change from before storage was less than −30%, it was determined that the storage stability was extremely poor and insufficient.

((flexural strength after storage (MPa)−flexural strength before storage (MPa))/(flexural strength before storage (MPa))×100[%] [Formula (4)]

Evaluation 4: Acid Neutralizing Ability

Each prepared dental curable composition was fully filled into a stainless mold (15φ×1 mm: disk shape). Thereafter, a cover glass was placed on upper side to apply pressure with glass plate. Subsequently, light irradiation was performed for 1 minute using a dental light curing unit (Blue Shot, manufactured by SHOFU Inc.) via the cover glass to prepare a cured product. The cured product was taken out from the mold, the cover glass was removed and the surface was polished with water-resistant abrasive paper #600. After removing the polishing dust, it was allowed to stand in a PP container containing 5 mL of an aqueous lactic acid solution adjusted to have pH value of 4.0, and was still allowed in a thermostatic chamber set at 37° C. for 48 hours. After 48 hours, the cured product was removed from the PP container, and the pH value was measured using a pH meter (electrode: 9618S-10D, main body: D-74, manufactured by Horiba, Ltd.). Evaluation criteria were as follows.

D (insufficient): pH value was less than 4.5.

C (certain acid neutralization ability): pH value was 4.5 or more and less than 5.0.

B (sufficient acid neutralization ability: pH value was 5.0 or more and less than 5.5.

A (excellent acid neutralization ability): pH value was 5.5 or more.

When the dental curable composition has an acid-neutralizing ability, it can be expected to neutralize surrounding acid even in the oral cavity, therefore an effect such as inhibition of demineralization of tooth substance can be expected.

Evaluation 5: Color Stability after Irradiation Stability

Each prepared dental curable composition was filled into a mold (15p×1 mm: disk shape) made of stainless steel. Thereafter, a cover glass was placed on upper side of the stainless mold to apply pressure with glass plate. Subsequently, light irradiation was performed for 1 minute using a photopolymerization irradiator (Grip Light II, manufactured by SHOFU INC.) via the cover glass to prepare a cured material. The cured material was taken out of the mold, the cover glass was removed and the test specimen was measured for color tone. Color measurement was performed by placing the test specimen on the background of a standard white plate (D65/10°, X=81.07, Y=86.15, Z=93.38) and using a spectrocolorimeter (manufactured by BYK-Chemie GmbH) under predetermined condition (light source: C, viewing angle: 2°, measurement area: 11 mm). Then, after exposing the test specimen to light for 24 hours with a xenon lamp light exposure tester (Suntest CPS+), the color tone of the test specimen was measured again, and the difference in discoloration was represented by ΔE calculated from the following formula.

$$\Delta E = ((\Delta L^*)^2 + (\Delta a^*)^2 + (\Delta b^*)^2)^{1/2}$$
$$\Delta L^* = L1^* - L2^*$$
$$\Delta a^* = a1^* - a2^*$$
$$\Delta b^* = b1^* - b2^*$$

In the formula, L1* is the brightness index before light exposure, L2* is the brightness index after light exposure, a1* and b1* are the color quality index before light exposure, and a2* and b2* are the color quality index after light exposure. Evaluation criteria were as follows.

Good: ΔE was less than 5
Applicable: ΔE was 5 or more and less than 8

-continued

Poor: ΔE was 8 or more and less than 10
Unavailable: ΔE was more than 10

Evaluation 6: Adhesion Strength to Tooth Substance

A test specimen of an epoxy resin embedded bovine anterior incisor was polished with water-resistant abrasive paper #600 to carve out an enamel plane and a dentin plane. Thereafter, a tape with a hole having a diameter of 4 mm was affixed to the adherend surface to prescribe an adhesion area. The adherend surface of the stainless rod (φ4.5 mm) was sandblasted (0.2 MPa, 1 second) with alumina (50 μm), then was washed with water and dried, and applied with a metal adhesive primer (METAL LINK, manufactured by SHOFU INC.). The adherend surface of the stainless rod was applied with appropriate amount of the dental curable composition of Examples or Comparative Example, and the test specimen of an epoxy resin embedded bovine anterior incisor carving out an enamel plane and a dentin plane and the stainless rod were bonded so as to fit in the frame of the double-sided tape with a hole. A load of 200 N was applied from the vertical direction of the stainless rod, and excess cement was wiped off with a cloth. Thereafter, light irradiation was performed for 10 seconds with the dental polymerization LED light irradiator (Blue Shot manufactured by SHOFU Inc.). After removing the load, the prepared adhesive test piece was immersed in water at 37° C. for 24 hours, an Instron universal tester (manufactured by Instron) was used to measure the shear adhesive strength at a crosshead speed of 1 mm/min. Evaluation criteria were as follows.

Excellent adhesive strength: adhesive strength was 10 MPa or more.

Low adhesive strength: adhesive strength was less than 5 MPa.

The adhesive strength to tooth substance was tested only for Examples D23 to D39 and Comparative Examples CD1, CD2, and CD3 to CD6. In Examples D23 to D39, a polymerizable monomer having an acidic group was compounded for the purpose of imparting adhesive property to tooth substance.

Excellent adhesive strength: adhesive strength was 10 MPa or more.

Low adhesive strength: adhesive strength was less than 5 MPa.

The adhesive strength to tooth substance was tested only for Examples D23 to D39 and Comparative Examples CD1, CD2, and CD3 to CD6. In Examples D23 to D39, a polymerizable monomer having an acidic group was compounded for the purpose of imparting adhesive property to tooth substance.

TABLE 9

| | Composition before storage (photo polymerization) Flexural strength | Storage composition before curing | Storage composition after curing | Color stability after irradiation | Acid neutralizing |
|---|---|---|---|---|---|
| | | Change rate of Flexural strength after acceleration teste | | | |
| | (MPa) | (%) | (%) | ΔE | ability |
| Example A1 | 133 | 0.8% | −7.9% | 2.9 | B |
| Example A2 | 121 | 0.8% | −4.2% | 2.0 | B |
| Example A3 | 136 | 1.0% | −6.0% | 2.7 | A |
| Example A4 | 99 | −1.1% | −4.4% | 2.5 | A |
| Example A5 | 98 | −0.9% | −5.9% | 2.4 | B |
| Example A6 | 121 | −3.2% | −4.6% | 2.9 | A |

TABLE 9-continued

| | Composition before storage (photo polymerization) Flexural strength | Storage composition before curing | Storage composition after curing | Color stability after irradiation | Acid neutralizing |
|---|---|---|---|---|---|
| | | Change rate of Flexural strength after acceleration teste | | | |
| | (MPa) | (%) | (%) | ΔE | ability |
| Example A7 | 128 | −6.5% | −9.2% | 2.6 | A |
| Example A8 | 127 | −2.9% | −6.5% | 2.3 | B |
| Example A9 | 123 | −2.1% | −9.3% | 1.7 | B |
| Example A10 | 127 | 1.5% | −7.9% | 2.7 | A |
| Example A11 | 90 | −4.2% | −7.8% | 2.6 | A |
| Example A12 | 101 | −4.6% | −7.4% | 2.9 | B |
| Example A13 | 88 | −1.5% | −9.4% | 2.8 | B |
| Example A14 | 86 | −3.3% | −11.3% | 2.4 | B |
| Example A15 | 87 | −8.0% | −6.1% | 2.4 | B |
| Example A16 | 84 | −3.0% | −21.3% | 2.8 | C |
| Example A17 | 143 | −2.1% | −5.7% | 1.9 | B |
| Example A18 | 149 | −4.5% | −7.0% | 2.9 | B |
| Example A19 | 84 | −0.4% | −3.2% | 2.8 | B |
| Example A20 | 83 | −1.4% | −2.9% | 5.2 | B |
| Example A21 | 110 | 0.0% | −21.9% | 5.8 | B |
| Example A22 | 107 | −1.1% | −8.9% | 2.1 | A |
| Example A23 | 88 | −4.0% | −4.7% | 2.3 | B |
| Example A24 | 126 | −15.5% | −9.1% | 3.5 | A |
| Example A25 | 107 | −4.4% | −8.5% | 4.7 | A |
| Example A26 | 94 | −0.3% | −7.3% | 9.1 | A |
| Example A27 | 94 | −2.3% | −9.6% | 2.0 | A |
| Example A28 | 85 | 1.8% | −5.9% | 1.7 | A |
| Example A29 | 126 | −0.7% | −9.4% | 2.0 | A |
| Example A30 | 101 | 1.9% | −5.4% | 5.8 | A |
| Example A31 | 96 | 0.4% | −6.5% | 9.3 | A |
| Example A32 | 107 | 0.2% | −7.1% | 9.5 | A |
| Example A33 | 99 | −3.1% | −7.3% | 9.6 | A |
| Example A34 | 116 | −2.6% | −6.2% | 2.7 | A |
| Example A35 | 117 | −7.2% | −6.2% | 5.1 | A |
| Example A36 | 117 | −3.6% | −11.4% | 2.7 | B |
| Example A37 | 125 | −0.6% | −11.1% | 2.5 | C |
| Example A38 | 120 | −2.8% | −5.9% | 2.0 | B |
| Example A39 | 137 | −2.9% | −6.9% | 2.4 | B |
| Example A40 | 145 | 1.3% | −5.4% | 1.8 | B |
| Example A41 | 143 | −0.3% | −8.6% | 2.3 | B |
| Example A42 | 138 | −4.7% | −6.6% | 2.9 | B |
| Example A43 | 140 | −1.2% | −7.7% | 1.8 | B |
| Example A44 | 147 | 1.1% | −4.0% | 1.6 | A |
| Example A45 | 131 | 1.5% | −5.2% | 2.6 | A |
| Example A46 | 132 | 0.2% | −12.3% | 2.1 | C |
| Example A47 | 143 | −2.1% | −4.9% | 2.2 | B |
| Example A48 | 140 | −1.3% | −4.1% | 2.1 | B |
| Example A49 | 115 | −9.1% | −4.4% | 2.9 | B |
| Comparative Example 1 | Uncured | Uncured | Uncured | Uncured | Uncured |
| Comparative Example 2 | 33 | −3% | −4.8% | 3.1 | B |
| Comparative Example 3 | 139 | 0% | −31% | 2.5 | D |
| Comparative Example 4 | 119 | −3% | −40% | 2.6 | D |
| Comparative Example 5 | 131 | 1% | −32% | 2.6 | D |
| Comparative Example 6 | 93 | −46% | −9.8% | 2.7 | B |
| Comparative Example 7 | 92 | −41% | −7.6% | 2.8 | B |
| Comparative Example 8 | 125 | −4% | −36% | 2.6 | D |
| Comparative Example 9 | 129 | −30% | −5.4% | 2.1 | B |
| Comparative Example 10 | 102 | −22% | −6.5% | 2.9 | A |
| Comparative Example 11 | 92 | −2% | −36% | 2.1 | D |
| Comparative Example 12 | 120 | −46% | −5.3% | 2.6 | A |
| Comparative Example 13 | 112 | −24% | −8.4% | 1.9 | B |
| Comparative Example 14 | 109 | −28% | −6.7% | 2.6 | B |

TABLE 9-continued

| | Composition before storage (photo polymerization) Flexural strength | Storage composition before curing | Storage composition after curing | Color stability after irradiation | Acid neutralizing |
|---|---|---|---|---|---|
| | | Change rate of Flexural strength after acceleration teste | | | |
| | (MPa) | (%) | (%) | ΔE | ability |
| Comparative Example 15 | 37 | −2% | −5.8% | 2.0 | A |
| Comparative Example 16 | 30 | 1% | −7.6% | 2.2 | A |
| Comparative Example 17 | 37 | −1% | −4.3% | 1.9 | A |

TABLE 10

| | Composition before storage (photo polymerization) Flexural strength | Storage composition before curing | Storage composition after curing | Color stability after irradiation | Acid neutralizing |
|---|---|---|---|---|---|
| | | Change rate of Flexural strength after acceleration teste | | | |
| | (MPa) | (%) | (%) | ΔE | ability |
| Example B1 | 103 | −0.8% | −4.4% | 2.6 | B |
| Example B2 | 108 | −2.4% | −0.3% | 3.0 | A |
| Example B3 | 93 | 0.6% | −4.0% | 1.7 | A |
| Example B4 | 94 | −1.2% | −2.7% | 2.9 | B |
| Example B5 | 102 | −2.2% | −1.1% | 1.9 | A |
| Example B6 | 108 | −8.8% | −2.2% | 2.2 | A |
| Example B7 | 112 | −2.1% | 0.0% | 1.7 | A |
| Example B8 | 100 | −1.5% | −0.5% | 1.7 | B |
| Example B9 | 89 | −0.6% | −1.7% | 2.6 | B |
| Example B10 | 88 | 1.0% | −20.3% | 1.7 | C |
| Example B11 | 89 | −2.5% | −10.2% | 5.7 | B |
| Example B12 | 86 | 1.4% | −2.8% | 5.5 | B |
| Example B13 | 102 | −3.4% | −3.6% | 2.6 | B |
| Example B14 | 103 | −2.6% | −4.2% | 2.4 | A |
| Example B15 | 85 | −4.8% | −4.9% | 1.6 | B |
| Example B16 | 109 | −13.1% | −3.9% | 1.6 | A |
| Example B17 | 83 | −3.0% | −4.1% | 1.6 | A |
| Example B18 | 114 | −4.0% | −3.5% | 1.6 | A |
| Example B19 | 107 | −1.7% | −2.3% | 5.6 | A |
| Example B20 | 90 | −1.4% | −2.1% | 9.3 | A |
| Example B21 | 93 | −4.1% | −1.2% | 9.5 | A |
| Example B22 | 145 | 0.2% | −4.3% | 1.7 | B |
| Example B23 | 107 | 0.8% | −12.3% | 2.2 | C |
| Example B24 | 104 | 1.2% | −2.5% | 2.4 | B |
| Example B25 | 135 | 5.6% | −4.4% | 1.7 | B |
| Example B26 | 141 | −4.4% | −2.8% | 2.0 | B |

TABLE 10-continued

| | Composition before storage (photo polymerization) Flexural strength | Storage composition before curing | Storage composition after curing | Color stability after irradiation | Acid neutralizing |
|---|---|---|---|---|---|
| | | Change rate of Flexural strength after acceleration teste | | | |
| | (MPa) | (%) | (%) | ΔE | ability |
| Example B27 | 139 | −3.4% | −4.5% | 2.9 | B |
| Example B28 | 137 | 0.8% | −3.3% | 2.1 | A |
| Comparative Example CB1 | Uncured | Uncured | Uncured | Uncured | Uncured |
| Comparative Example CB2 | 56 | 1% | 0.0% | 2.8 | B |
| Comparative Example CB3 | 105 | −3% | −34% | 2.8 | D |
| Comparative Example CB4 | 101 | 2% | −35% | 2.2 | D |
| Comparative Example CB5 | 97 | −48% | −4.3% | 2.8 | B |
| Comparative Example CB6 | 104 | −27% | −2.7% | 2.6 | B |
| Comparative Example CB7 | 49 | −3% | −0.5% | 3.0 | A |

TABLE 11

| | Composition before storage (photo polymerization) Flexural strength | Storage composition before curing | Storage composition after curing | Color stability after irradiation | Acid neutralizing | Adhesion strength to tooth substance |
|---|---|---|---|---|---|---|
| | | Change rate of Flexural strength after acceleration teste | | | | |
| | (MPa) | (%) | (%) | ΔE | ability | (MPa) |
| Example D1 | 106 | −3.3% | −1.5% | 2.6 | B | |
| Example D2 | 102 | −1.5% | −0.8% | 2.4 | A | |
| Example D3 | 73 | −3.7% | −4.8% | 2.5 | A | |
| Example D4 | 72 | 0.7% | −2.0% | 2.1 | B | |
| Example D5 | 102 | −1.1% | −3.0% | 2.8 | A | |
| Example D6 | 106 | −8.5% | −2.5% | 1.9 | A | |
| Example D7 | 83 | −1.8% | −1.0% | 2.1 | B | |
| Example D8 | 81 | −4.0% | 0.0% | 2.6 | B | |
| Example D9 | 85 | −0.6% | −25.1% | 2.0 | C | |
| Example D10 | 73 | −1.2% | −1.1% | 2.2 | A | |
| Example D11 | 104 | −1.8% | −14.5% | 4.3 | C | |
| Example D12 | 109 | −3.8% | −3.6% | 2.3 | B | |
| Example D13 | 110 | −0.9% | −4.0% | 2.0 | B | |
| Example D14 | 110 | −2.1% | −0.3% | 2.1 | B | |
| Example D15 | 105 | −4.3% | −1.9% | 2.1 | B | |
| Example D16 | 106 | 1.6% | −1.5% | 1.9 | B | |
| Example D17 | 102 | −2.1% | −0.9% | 1.8 | B | |
| Example D18 | 107 | −1.9% | −0.9% | 2.9 | A | |
| Example D19 | 66 | −8.4% | −4.5% | 2.4 | A | |
| Example D20 | 63 | −3.1% | −0.4% | 3.0 | A | |

TABLE 11-continued

| | Composition before storage (photo polymerization) Flexural strength | Storage composition before curing | Storage composition after curing | Color stability after irradiation | Acid neutralizing | Adhesion strength to tooth substance |
|---|---|---|---|---|---|---|
| | | Change rate of Flexural strength after acceleration teste | | | | |
| | (MPa) | (%) | (%) | ΔE | ability | (MPa) |
| Example D21 | 101 | −2.0% | −3.3% | 2.5 | A | |
| Example D22 | 108 | −4.5% | −1.0% | 2.0 | A | |
| Example D23 | 105 | 0.7% | −2.8% | 5.3 | B | 11.1 |
| Example D24 | 102 | −19.6% | −22.0% | 2.9 | B | 15.7 |
| Example D25 | 109 | −1.6% | −20.8% | 1.7 | C | 10.9 |
| Example D26 | 101 | −1.0% | −2.7% | 2.0 | A | 12.1 |
| Example D27 | 108 | −4.5% | −5.0% | 2.5 | A | 5.3 |
| Example D28 | 104 | −4.5% | 0.0% | 2.1 | A | 10.1 |
| Example D29 | 100 | 0.5% | −3.8% | 1.8 | A | 11.2 |
| Example D30 | 104 | 1.8% | −0.9% | 1.6 | A | 13.2 |
| Example D31 | 107 | −2.0% | −1.0% | 2.6 | A | 10.9 |
| Example D32 | 104 | −4.1% | −1.2% | 2.6 | A | 11.2 |
| Example D33 | 121 | −5.0% | −10.1% | 1.8 | A | 10.7 |
| Example D34 | 126 | −0.1% | −3.1% | 1.8 | B | 11.8 |
| Example D35 | 106 | 0.4% | −2.7% | 1.6 | A | 14.9 |
| Example D36 | 105 | 0.2% | −2.4% | 2.0 | A | 13.4 |
| Example D37 | 103 | −2.5% | −1.3% | 2.4 | A | 12.3 |
| Example D38 | 106 | −3.5% | −2.4% | 2.3 | A | 11.3 |
| Example D39 | 110 | −1.0% | −0.3% | 1.6 | A | 13.8 |
| Comparative Example CD1 | Uncured | Uncured | Uncured | Uncured | Uncured | Uncured |
| Comparative Example CD2 | Uncured | Uncured | Uncured | Uncured | Uncured | Uncured |
| Comparative Example CD3 | 100 | −26% | −4.1% | 3.4 | B | |
| Comparative Example CD4 | 102 | −1.8% | −33% | 3.1 | D | 13.1 |
| Comparative Example CD5 | 103 | −30% | −2.9% | 2.5 | B | 13.1 |
| Comparative Example CD6 | 108 | −45% | −0.7% | 1.7 | A | 13.7 |

It was confirmed that the compositions described in Examples had sufficient flexural strength, storage stability and acid neutralizing ability.

In Example A3, Example A4 and Example B14 and the like containing filler E3, E4, E6 and E15 treated with an acidic polymer as the (E1) surface-treated basic filler treated with an acidic polymer, there was a tendency that good acid-neutralizing ability was exhibited. In Example A1 and Example A2 and the like containing filler E1, E2, E3, E6, E7, E8, E9, E11, E12, E13, E14 and E15 treated with a silane coupling agent, there was a tendency that good flexural strength was exhibited. In Examples A4 and B3 containing only filler not treated with a silane coupling agent, there was a tendency that the flexural strength was slightly low. In Example A5 and the like containing filler E5 not treated with a silane coupling agent and not treated with an acidic polymer, there was a tendency that the flexural strength was slightly low and acid-neutralizing ability was slightly low.

In Examples A15, B6 and D6 containing only filler E7 having high basicity among the (E1) surface-treated basic filler, the storage stability of the composition before curing was slightly inferior. In Examples A37, A46, B23 and D11 containing only filler E8 heat treated at a temperature of 450° C., there was a tendency that the storage stability of the composition after curing was slightly low and acid-neutralizing ability was slightly low. In Example A39, Example B24, Example D13 and Example D34 which contain filler E10 heat treated at a temperature of 400° C., there was a tendency that the storage stability of the composition after curing was slightly low although it was gently compared to Example containing only filler E8. On the other hand, in Example D33 containing filler E1 and filler E3 while containing filler E8, good acid neutralizing ability was exhibited. In Example A49 containing filler E16 in which the heat treatment temperature was as low as 90° C., the storage stability of the composition before curing was slightly low. In Examples A16, B10, D9 and D25 in which the amount of the (E1) surface-treated basic filler was small, there was a tendency that the storage stability of the composition after curing was low and acid neutralizing ability was low.

In Examples A19 and B11 in which the compounding amount of the photoacid generator was small, there was a tendency that the flexural strength was slightly low. In Examples A20 and B12 in which the compounding amount of the photoacid generator was large, there was a tendency that the color stability after irradiation was slightly lowered. In Example D19 in which the compounding amount of the organic peroxide was small, there was a tendency that the flexural strength was slightly low. In Examples A23, B15 and D20 in which the compounding amount of the polymerization accelerator was small, there was a tendency that the flexural strength was slightly low. In Examples A24 and B16 in which the compounding amount of the polymerization accelerator was large, there was a tendency that the storage stability of the composition before curing was slightly inferior.

In Examples A20 and B12 in which the compounding amount of the photoacid generator was small, there was a tendency that the flexural strength was slightly low. In Examples A21 and B11 in which the compounding amount of the photoacid generator was large, there was a tendency that the storage stability of the composition after curing was slightly inferior. In Examples A30-33, A35 and B19-21 in which photoacid generator other than a salt of an anion having an organic group and one or more atoms of P, B, Al, S, and Ga, and an aryl iodonium cation was compounded, there was a tendency that the color stability after irradiation slightly decreased. In Example D27 containing a small amount of the polymerizable monomer having an acid group, there was a tendency that the adhesive strength to dentin was slightly low. In Example D24 containing a large amount of the polymerizable monomer having an acid group, there was a tendency that the storage stability of the composition before curing and after curing was slightly low. In Examples A28 and B17 not containing a camphorquinone based photosensitizer as the photopolymerization initiator, there was a tendency that the flexural strength was low.

In Example A26 and the like containing an aromatic amine such as DMBE and DEPT as a polymerization accelerator, there was a tendency that the color stability after irradiation decreased. In Example A25 and Example D13, because an ultraviolet absorber was added simultaneously, deterioration in color stability after irradiation was not observed.

In Comparative Examples CA1, CA2, CA15, CA16, CA17, CB1, CB2, CB7, CD1, and CD2, because a portion of the polymerization initiator or polymerization accelerator was not contained, flexural strength was low or curing did not occur.

In Comparative Examples CA3, CA4, CA5, CA8, CA11, CB5, CB6, CD4, CD5, and CD6, because the basic filler not treated with polysiloxane was contained, there was a tendency that the flexural property after storage of the paste before curing was remarkably decreased compared to before storage. In Comparative Examples CA6, CA7, CA9, CA10, CA12, CA13, CA14, CB3, CB4 and CD6, because only non-basic filler was contained, the flexural property of the cured product after storage was remarkably decreased compared to before storage.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

According to the present disclosure, it is possible to provide a dental curable composition having high storage stability and good mechanical property.

What is claimed is:

1. A dental curable composition, comprising (A) polymerizable monomer, (BC) polymerization initiator, (D) polymerization accelerator and (E) filler, wherein, the (BC) polymerization initiator comprises (B) photopolymerization initiator and optionally (C) chemical polymerization initiator, the (B) photopolymerization initiator comprises (B1) photosensitizer and (B2) photoacid generator, the (B2) photoacid generator comprises an aryl iodonium salt, the aryl iodonium salt is a salt of an anion having an organic group and one or more atoms selected from the group consisting of P, B, Al, S and Ga, and an aryl iodonium cation, the (C) chemical polymerization initiator comprises (C1) organic peroxide, the (E) filler comprises (E1) surface-treated basic filler, the (E1) surface-treated basic filler is treated with (F1) surface treatment agent represented by the formula (1) and/or condensate thereof:

[Formula (1)]

$MX_n$ wherein, M is a metal atom selected from Si, Ti, Zr, and Al, X is H, OH or a hydrolyzable group, and may be the same or different from each other, In the case that M is Si, Ti or Zr, n is 4, In the case that M is Al, n is 3, and a composition range of the (E1) surface-treated basic filler satisfies $SiO_2$: 15 to 35% by mass, $Al_2O_3$: 15 to 30% by mass, SrO: 20 to 45% by mass, $P_2O_5$: 0 to 15% by mass, F: 5 to 15% by mass, $Na_2O$: 0 to 10% by mass, $B_2O_3$: 0 to 20% by mass and CaO: 0 to 10% by mass.

2. The dental curable composition according to claim 1, wherein the (F1) surface treatment agent represented by the formula (1) and/or condensate thereof is a partial condensate of 2 to 100 molecules of tetraalkoxysilane or a polysiloxane in which all or part of alkoxy groups of a partial condensate of 2 to 100 molecules of tetraalkoxysilane is substituted with OH group.

3. The dental curable composition according to claim 1, wherein the (E1) surface-treated basic filler is surface-treated by a wet method and heating under a heat treatment condition at a temperature of 130° C. or higher and 400° C.

or lower for an hour or longer and by using the (F1) surface treatment agent represented by the formula (1) and/or condensate thereof.

4. The dental curable composition according to claim 1, wherein the (E1) surface-treated basic filler is surface-treated with a silane coupling agent having a polymerizable group and/or an acidic polymer in addition to the surface treatment with the (F1) surface treatment agent represented by the formula (1) and/or condensate thereof.

5. The dental curable composition according to claim 1, wherein a dispersion of 1.0 g of the (E1) surface-treated basic filler in a mixed solution of 40 g of distilled water and 10 g of ethanol has pH-value in a range from 7.5 to 10.0 after stirring for 1 hour.

6. The dental curable composition according to claim 1, wherein the (E1) surface-treated basic filler is one or more selected from the group consisting of a fluorosilicate glass, a fluoroaluminosilicate glass and a fluoroaluminoborosilicate glass.

7. The dental curable composition according to claim 1, wherein the aryl iodonium salt is a salt of an anion having an organic group in which at least one His substituted with F and one or more atoms selected from the group consisting of P, B, Al, S and Ga, and an aryl iodonium cation.

8. The dental curable composition according to claim 1, wherein the (D) polymerization accelerator contains aliphatic tertiary amine compound.

9. The dental curable composition according to claim 1, wherein 1 to 30 parts by mass in 100 parts by mass of the (A) polymerizable monomer contained in the dental curable composition is (A1) polymerizable monomer having an acidic group.

10. The dental curable composition according to claim 1, wherein the dental curable composition is one pack type dental curable composition, and the dental curable composition comprises, with respect to 100 parts by mass of the (A) polymerizable monomer contained in the dental curable composition, 0.02 to 1.0 parts by mass of the (B1) photosensitizer, 0.1 to 10 parts by mass of the (B2) photoacid generator, 0.2 to 10 parts by mass of the (D) polymerization accelerator, and 10 to 500 parts by mass of the (E1) surface-treated basic filler.

11. The dental curable composition according to claim 1, wherein the dental curable composition is two packs type dental curable composition, the dental curable composition consists of a first paste and a second paste, a mass ratio of the first paste and the second paste is 1:0.8 to 1.2, and with respect to 200 parts by mass of total of the (A) polymerizable monomer contained in the first paste and the second paste, a content of the (B1) photosensitizer is 0.04 to 2.0 parts by mass, a content of the (B2) photoacid generator is 0.2 to 20 parts by mass, a content of the (D) polymerization accelerator is 0.4 to 20 parts by mass, and a content of the (E1) surface-treated basic filler is 10 to 500 parts by mass.

12. The dental curable composition according to claim 1, wherein the dental curable composition is two packs type dental curable composition, the dental curable composition consists of a first paste and a second paste, a mass ratio of the first paste and the second paste is 1:0.8 to 1.2, and with respect to 200 parts by mass of total of the (A) polymerizable monomer contained in the first paste and the second paste, a content of the (C1) organic peroxide is 0.2 to 10 parts by mass, a content of the (D) polymerization accelerator is 0.4 to 20 parts by mass, and a content of the (E1) surface-treated basic filler is 10 to 400 parts by mass.

13. The dental curable composition according to claim 1, wherein the dental curable composition is two packs type dental curable composition, the dental curable composition consists of a first paste and a second paste, a mass ratio of the first paste and the second paste is 1:0.8 to 1.2, and with respect to 200 parts by mass of total of the (A) polymerizable monomer contained in the first paste and the second paste, a content of the (C1) organic peroxide is 0.2 to 10 parts by mass, a content of the (D) polymerization accelerator is 0.4 to 20 parts by mass, a content of the (E1) surface-treated basic filler is 10 to 400 parts by mass, and a content of the (A1) polymerizable monomer having an acidic group is 2 to 60 parts by mass in 200 parts by mass of total of the (A) polymerizable monomer.

14. The dental curable composition according to claim 1, wherein pH-value after immersing a cured body of the dental curable composition having a diameter of 15 mm and a thickness of 1 mm in 5 mL of a lactic acid aqueous solution having pH-value of 4.0 for 24 hours is 4.5 or more.

15. The dental curable composition according to claim 1, wherein the dental curable composition does not substantially contain water.

16. A dental curable composition, comprising (A) polymerizable monomer, (BC) polymerization initiator, (D) polymerization accelerator and (E) filler, wherein, the (BC) polymerization initiator comprises (B) photopolymerization initiator and optionally (C) chemical polymerization initiator, the (B) photopolymerization initiator comprises (B1) photosensitizer and (B2) photoacid generator, the (B2) photoacid generator comprises an aryl iodonium salt, the aryl iodonium salt is a salt of an anion having an organic group and one or more atoms selected from the group consisting of P, B, Al, S and Ga, and an aryl iodonium cation, the (C) chemical polymerization initiator comprises (C1) organic peroxide, the (E) filler comprises (E1) surface-treated basic filler, and the (E1) surface-treated basic filler is treated with (F1) surface treatment agent represented by the formula (1) and/or condensate thereof:

[Formula (1)]

wherein, M is a metal atom selected from Si, Ti, Zr, and Al, X is H, OH or a hydrolyzable group, and may be the same or different from each other, In the case that M is Si, Ti or Zr, n is 4, In the case that M is Al, n is 3, and wherein 1 to 30 parts by mass in 100 parts by mass of the (A) polymerizable monomer contained in the dental curable composition is (A1) polymerizable monomer having an acidic group.

17. The dental curable composition according to claim 16, wherein the (F1) surface treatment agent represented by the formula (1) and/or condensate thereof is a partial condensate of 2 to 100 molecules of tetraalkoxysilane or a polysiloxane in which all or part of alkoxy groups of a partial condensate of 2 to 100 molecules of tetraalkoxysilane is substituted with OH group.

18. The dental curable composition according to claim 16, wherein the (E1) surface-treated basic filler is surface-treated with a silane coupling agent having a polymerizable group and/or an acidic polymer in addition to the surface treatment with the (F1) surface treatment agent represented by the formula (1) and/or condensate thereof.

19. The dental curable composition according to claim 16, wherein a dispersion of 1.0 g of the (E1) surface-treated basic filler in a mixed solution of 40 g of distilled water and 10 g of ethanol has pH-value in a range from 7.5 to 10.0 after stirring for 1 hour.

20. The dental curable composition according to claim 16, wherein the aryl iodonium salt is a salt of an anion having an organic group in which at least one His substituted with F and one or more atoms selected from the group consisting of P, B, Al, S and Ga, and an aryl iodonium cation.

21. The dental curable composition according to claim 16, wherein the (D) polymerization accelerator contains aliphatic tertiary amine compound.

22. The dental curable composition according to claim 16, wherein the dental curable composition is one pack type dental curable composition, and the dental curable composition comprises, with respect to 100 parts by mass of the (A) polymerizable monomer contained in the dental curable composition, 0.02 to 1.0 parts by mass of the (B1) photosensitizer, 0.1 to 10 parts by mass of the (B2) photoacid generator, 0.2 to 10 parts by mass of the (D) polymerization accelerator, and 10 to 500 parts by mass of the (E1) surface-treated basic filler.

23. The dental curable composition according to claim 16, wherein the dental curable composition is two packs type dental curable composition, the dental curable composition consists of a first paste and a second paste, a mass ratio of the first paste and the second paste is 1:0.8 to 1.2, and with respect to 200 parts by mass of total of the (A) polymerizable monomer contained in the first paste and the second paste, a content of the (B1) photosensitizer is 0.04 to 2.0 parts by mass, a content of the (B2) photoacid generator is 0.2 to 20 parts by mass, a content of the (D) polymerization accelerator is 0.4 to 20 parts by mass, and a content of the (E1) surface-treated basic filler is 10 to 500 parts by mass.

24. The dental curable composition according to claim 16, wherein the dental curable composition is two packs type dental curable composition, the dental curable composition consists of a first paste and a second paste, a mass ratio of the first paste and the second paste is 1:0.8 to 1.2, and with respect to 200 parts by mass of total of the (A) polymerizable monomer contained in the first paste and the second paste, a content of the (C1) organic peroxide is 0.2 to 10 parts by mass, a content of the (D) polymerization accelerator is 0.4 to 20 parts by mass, and a content of the (E1) surface-treated basic filler is 10 to 400 parts by mass.

25. The dental curable composition according to claim 16, wherein the dental curable composition is two packs type dental curable composition, the dental curable composition consists of a first paste and a second paste, a mass ratio of the first paste and the second paste is 1:0.8 to 1.2, and with respect to 200 parts by mass of total of the (A) polymerizable monomer contained in the first paste and the second paste, a content of the (C1) organic peroxide is 0.2 to 10 parts by mass, a content of the (D) polymerization accelerator is 0.4 to 20 parts by mass, a content of the (E1) surface-treated basic filler is 10 to 400 parts by mass, and a content of the (A1) polymerizable monomer having an acidic group is 2 to 60 parts by mass in 200 parts by mass of total of the (A) polymerizable monomer.

26. The dental curable composition according to claim 16, wherein pH-value after immersing a cured body of the dental curable composition having a diameter of 15 mm and a thickness of 1 mm in 5 mL of a lactic acid aqueous solution having pH-value of 4.0 for 24 hours is 4.5 or more.

27. The dental curable composition according to claim 16, wherein the dental curable composition does not substantially contain water.

* * * * *